United States Patent
Armour et al.

(10) Patent No.: US 9,957,549 B2
(45) Date of Patent: *May 1, 2018

(54) COMPOSITIONS AND METHODS FOR NEGATIVE SELECTION OF NON-DESIRED NUCLEIC ACID SEQUENCES

(71) Applicant: NUGEN TECHNOLOGIES, INC., San Carlos, CA (US)

(72) Inventors: Christopher Armour, Kirkland, WA (US); Doug Amorese, Los Altos, CA (US); Bin Li, Palo Alto, CA (US); Nurith Kurn, Palo Alto, CA (US)

(73) Assignee: NUGEN TECHNOLOGIES, INC., San Carlos, CA (US)

(*) Notice: Subject to any disclaimer, the term of this patent is extended or adjusted under 35 U.S.C. 154(b) by 0 days. days.

This patent is subject to a terminal disclaimer.

(21) Appl. No.: 14/390,012

(22) PCT Filed: Mar. 15, 2013

(86) PCT No.: PCT/US2013/032606
§ 371 (c)(1),
(2) Date: Oct. 1, 2014

(87) PCT Pub. No.: WO2013/191775
PCT Pub. Date: Dec. 27, 2013

(65) Prior Publication Data
US 2015/0299767 A1 Oct. 22, 2015

Related U.S. Application Data

(60) Provisional application No. 61/661,293, filed on Jun. 18, 2012.

(51) Int. Cl.
*C12Q 1/68* (2018.01)
*C12N 15/10* (2006.01)

(52) U.S. Cl.
CPC ....... *C12Q 1/6806* (2013.01); *C12N 15/1093* (2013.01); *C12N 15/1096* (2013.01); *C12Q 1/6844* (2013.01)

(58) Field of Classification Search
None
See application file for complete search history.

(56) References Cited

U.S. PATENT DOCUMENTS

| | | |
|---|---|---|
| 4,362,867 A | 12/1982 | Paddock |
| 4,458,066 A | 7/1984 | Caruthers et al. |
| 4,469,863 A | 9/1984 | Ts'o et al. |
| 4,582,877 A | 4/1986 | Fairchok et al. |
| 4,876,187 A | 10/1989 | Duck et al. |
| 4,935,357 A | 6/1990 | Szybalski |
| 4,942,124 A | 7/1990 | Church |
| 4,988,617 A | 1/1991 | Landegren et al. |
| 4,996,143 A | 2/1991 | Hartley et al. |
| 5,011,769 A | 4/1991 | Duck et al. |
| 5,034,506 A | 7/1991 | Summerton et al. |
| 5,035,996 A | 7/1991 | Hartley |
| 5,043,272 A | 8/1991 | Hartley |
| 5,082,830 A | 1/1992 | Brakel et al. |
| 5,090,591 A | 2/1992 | Long |
| 5,130,238 A | 7/1992 | Malek et al. |
| 5,169,766 A | 12/1992 | Schuster et al. |
| 5,171,534 A | 12/1992 | Smith et al. |
| 5,194,370 A | 3/1993 | Berninger et al. |
| 5,216,141 A | 6/1993 | Benner |
| 5,234,809 A | 8/1993 | Boom et al. |
| 5,235,033 A | 8/1993 | Summerton et al. |
| 5,242,794 A | 9/1993 | Whiteley et al. |
| 5,386,023 A | 1/1995 | Sanghvi et al. |
| 5,399,491 A | 3/1995 | Kucian et al. |
| 5,409,818 A | 4/1995 | Davey et al. |
| 5,418,149 A | 5/1995 | Gelfand et al. |

(Continued)

FOREIGN PATENT DOCUMENTS

| | | |
|---|---|---|
| CA | 2444926 A1 | 11/2002 |
| EP | 0365627 B1 | 5/1990 |

(Continued)

OTHER PUBLICATIONS

Alvarado, et al. Multiplexed direct genomic selection (MDiGS): a pooled BAC capture approach for highly accurate CNV and SNP/INDEL detection. Nucleic Acids Res. Jun. 2014;42(10):e82. doi: 10.1093/nar/gku218. Epub Mar. 20, 2014.

CNV detection by ion semiconductor sequencing. Life Technologies. 2014.

McClure, et al. Bovine exome sequence analysis and targeted SNP genotyping of recessive fertility defects BH1, HH2, and HH3 reveal a putative causative mutation in SMC2 for HH3. PLoS One. Mar, 25, 2014;9(3):e92769. doi: 10.1371/journal.pone.0092769. eCollection 2014.

Pabinger, et al. A survey of tools for variant analysis of next-generation genome sequencing data. Brief Bioinform. Mar. 2014;15(2):256-78. doi: 10.1093/bib/bbs086. Epub Jan. 21, 2013.

Myllykangas, et al. Efficient targeted resequencing of human germline and cancer genomes by oligonucleotide-selective sequencing. Nat Biotechnol. Oct. 23, 2011;29(11):1024-7. doi: 10.1038/nbt.1996.

(Continued)

*Primary Examiner* — Suryaprabha Chunduru
(74) *Attorney, Agent, or Firm* — Wilson Sonsini Goodrich & Rosati

(57) ABSTRACT

The present invention provides methods, compositions and kits for the generation of next generation sequencing (NGS) libraries in which non-desired nucleic acid sequences have been depleted or substantially reduced. The methods, compositions and kits provided herein are useful, for example, for the production of libraries from total RNA with reduced ribosomal RNA and for the reduction of common mRNA species in expression profiling from mixed samples where the mRNAs of interest are present at low levels. The methods of the invention can be employed for the elimination of non-desired nucleic acid sequences in a sequence-specific manner, and consequently, for the enrichment of nucleic acid sequences of interest in a nucleic acid library.

52 Claims, 9 Drawing Sheets

(56) References Cited

U.S. PATENT DOCUMENTS

| | | |
|---|---|---|
| 5,427,929 A | 6/1995 | Richards et al. |
| 5,480,784 A | 1/1996 | Kacian et al. |
| 5,573,913 A | 1/1996 | Rosemeyer et al. |
| 5,494,810 A | 2/1996 | Barany et al. |
| 5,508,169 A | 4/1996 | Deugau et al. |
| 5,508,178 A | 4/1996 | Rose et al. |
| 5,510,270 A | 4/1996 | Fodor et al. |
| 5,525,471 A | 6/1996 | Zeng |
| 5,545,522 A | 8/1996 | Van Gelder et al. |
| 5,554,516 A | 9/1996 | Kacian et al. |
| 5,554,517 A | 9/1996 | Davey et al. |
| 5,556,752 A | 9/1996 | Lockhart et al. |
| 5,565,340 A | 10/1996 | Chenchik et al. |
| 5,578,832 A | 11/1996 | Trulson et al. |
| 5,589,339 A | 12/1996 | Hampson et al. |
| 5,602,240 A | 2/1997 | De Mesmaeker et al. |
| 5,637,684 A | 6/1997 | Cook et al. |
| 5,641,658 A | 6/1997 | Adams et al. |
| 5,644,048 A | 7/1997 | Yau et al. |
| 5,665,549 A | 9/1997 | Pinkel et al. |
| 5,667,976 A | 9/1997 | Van Ness et al. |
| 5,667,979 A | 9/1997 | Berrens |
| 5,679,512 A | 10/1997 | Laney et al. |
| 5,681,726 A | 10/1997 | Huse et al. |
| 5,683,879 A | 11/1997 | Laney et al. |
| 5,688,648 A | 11/1997 | Mathies et al. |
| 5,705,628 A | 1/1998 | Hawkins |
| 5,708,154 A | 1/1998 | Smith et al. |
| 5,710,028 A | 1/1998 | Eyal et al. |
| 5,712,126 A | 1/1998 | Weissmann et al. |
| 5,716,785 A | 2/1998 | Van Gelder et al. |
| 5,726,329 A | 3/1998 | Jones et al. |
| 5,750,341 A | 5/1998 | Macevicz |
| 5,759,822 A | 6/1998 | Chenchik et al. |
| 5,763,178 A | 6/1998 | Chirikjian et al. |
| 5,789,206 A | 8/1998 | Tavtigian et al. |
| 5,824,517 A | 10/1998 | Cleuziat et al. |
| 5,824,518 A | 10/1998 | Kacian et al. |
| 5,837,832 A | 11/1998 | Chee et al. |
| 5,876,976 A | 3/1999 | Richards et al. |
| 5,882,867 A | 3/1999 | Ullman et al. |
| 5,888,779 A | 3/1999 | Kacian et al. |
| 5,888,819 A | 3/1999 | Goelet et al. |
| 5,945,313 A | 8/1999 | Hartley et al. |
| 5,952,176 A | 9/1999 | McCarthy et al. |
| 5,958,681 A | 9/1999 | Wetmur et al. |
| 5,965,409 A | 10/1999 | Pardee et al. |
| 5,969,119 A | 10/1999 | Macevicz |
| 5,972,618 A | 10/1999 | Bloch |
| 6,004,744 A | 12/1999 | Goelet et al. |
| 6,004,745 A | 12/1999 | Arnold, Jr. et al. |
| 6,027,889 A | 2/2000 | Barany et al. |
| 6,027,923 A | 2/2000 | Wallace |
| 6,030,774 A | 2/2000 | Laney et al. |
| 6,037,152 A | 3/2000 | Richards et al. |
| 6,056,661 A | 5/2000 | Schmidt |
| 6,077,674 A | 6/2000 | Schuster et al. |
| 6,087,103 A | 7/2000 | Burmer |
| 6,090,553 A | 7/2000 | Matson |
| 6,090,591 A | 7/2000 | Berg et al. |
| 6,107,023 A | 8/2000 | Reyes et al. |
| 6,110,709 A | 8/2000 | Ausubel et al. |
| 6,150,112 A | 11/2000 | Weissmann et al. |
| 6,159,685 A | 12/2000 | Pinkel et al. |
| 6,160,105 A | 12/2000 | Cunningham et al. |
| 6,169,194 B1 | 1/2001 | Thompson et al. |
| 6,172,208 B1 | 1/2001 | Cook |
| 6,174,680 B1 | 1/2001 | Makrigiorgos |
| 6,190,865 B1 | 2/2001 | Jendrisak et al. |
| 6,194,211 B1 | 2/2001 | Richards et al. |
| 6,197,501 B1 | 3/2001 | Cremer et al. |
| 6,197,557 B1 | 3/2001 | Makarov et al. |
| 6,210,891 B1 | 4/2001 | Nyren et al. |
| 6,225,109 B1 | 5/2001 | Juncosa et al. |
| 6,225,451 B1 | 5/2001 | Ballinger et al. |
| 6,232,104 B1 | 5/2001 | Lishanski et al. |
| 6,251,639 B1 | 6/2001 | Kurn |
| 6,262,490 B1 | 7/2001 | Hsu et al. |
| 6,270,961 B1 | 8/2001 | Drmanac |
| 6,280,935 B1 | 8/2001 | Maceivicz |
| 6,287,766 B1 | 9/2001 | Nolan et al. |
| 6,287,825 B1 | 9/2001 | Weissman et al. |
| 6,291,170 B1 | 9/2001 | Van Gelder et al. |
| 6,306,365 B1 | 10/2001 | Ruoslahti et al. |
| 6,306,597 B1 | 10/2001 | Macevicz |
| 6,309,843 B1 | 10/2001 | Timms |
| 6,326,142 B1 | 12/2001 | Royer |
| 6,335,167 B1 | 1/2002 | Pinkel et al. |
| 6,339,147 B1 | 1/2002 | Luktanov et al. |
| 6,440,705 B1 | 8/2002 | Stanton, Jr. et al. |
| 6,449,562 B1 | 9/2002 | Chandler et al. |
| 6,582,938 B1 | 6/2003 | Su et al. |
| 6,670,461 B1 | 12/2003 | Wengel et al. |
| 6,686,156 B2 | 2/2004 | Kurn |
| 6,692,918 B2 | 2/2004 | Kurn |
| 6,770,748 B2 | 8/2004 | Imanishi et al. |
| 6,777,180 B1 | 8/2004 | Fisher et al. |
| 6,794,499 B2 | 9/2004 | Wengel et al. |
| 6,815,164 B2 | 11/2004 | Kurn |
| 6,815,167 B2 | 11/2004 | Crothers et al. |
| 6,825,011 B1 | 11/2004 | Romantchikov |
| 6,833,246 B2 | 12/2004 | Balasubramanian |
| 6,849,404 B2 | 2/2005 | Park et al. |
| 6,858,413 B2 | 2/2005 | Kurn |
| 6,913,884 B2 | 7/2005 | Stuelpnagel et al. |
| 6,917,726 B2 | 7/2005 | Levene et al. |
| 6,924,104 B2 | 8/2005 | Weissmann et al. |
| 6,946,251 B2 | 9/2005 | Kurn |
| 7,001,724 B1 | 2/2006 | Greenfield |
| 7,033,764 B2 | 4/2006 | Korlach et al. |
| 7,048,481 B2 | 5/2006 | Sugata et al. |
| 7,052,847 B2 | 5/2006 | Korlach et al. |
| 7,056,676 B2 | 6/2006 | Korlach et al. |
| 7,056,716 B2 | 6/2006 | Potter et al. |
| 7,060,441 B2 | 6/2006 | Bourget et al. |
| 7,094,536 B2 | 8/2006 | Kurn |
| 7,115,400 B1 | 10/2006 | Adessi et al. |
| 7,170,050 B2 | 1/2007 | Turner |
| 7,175,982 B1 | 2/2007 | McCarthy et al. |
| 7,176,025 B2 | 2/2007 | Kurn et al. |
| 7,189,512 B2 | 3/2007 | Porat et al. |
| 7,211,390 B2 | 5/2007 | Rothberg et al. |
| 7,232,656 B2 | 6/2007 | Balasubramanian et al. |
| 7,244,559 B2 | 7/2007 | Rothberg et al. |
| 7,244,567 B2 | 7/2007 | Chen et al. |
| 7,264,929 B2 | 9/2007 | Rothberg et al. |
| 7,273,730 B2 | 9/2007 | Du Breuil |
| 7,276,720 B2 | 10/2007 | Ulmer |
| 7,294,461 B2 | 11/2007 | Kurn |
| 7,300,755 B1 | 11/2007 | Petersdorf et al. |
| 7,302,146 B2 | 11/2007 | Turner et al. |
| 7,313,308 B2 | 12/2007 | Turner et al. |
| 7,315,019 B2 | 1/2008 | Turner et al. |
| 7,323,305 B2 | 1/2008 | Leamon et al. |
| 7,335,762 B2 | 2/2008 | Rothberg et al. |
| 7,351,557 B2 | 4/2008 | Kurn |
| 7,354,717 B2 | 4/2008 | Kurn |
| 7,361,466 B2 | 4/2008 | Korlach et al. |
| 7,361,468 B2 | 4/2008 | Liu et al. |
| 7,402,386 B2 | 7/2008 | Kurn et al. |
| 7,405,281 B2 | 7/2008 | Xu et al. |
| 7,414,117 B2 | 8/2008 | Saito et al. |
| 7,416,844 B2 | 8/2008 | Korlach et al. |
| 7,462,452 B2 | 12/2008 | Williams et al. |
| 7,462,468 B1 | 12/2008 | Williams et al. |
| 7,476,503 B2 | 1/2009 | Turner et al. |
| 7,476,504 B2 | 1/2009 | Turner |
| 7,491,498 B2 | 2/2009 | Lapidus et al. |
| 7,501,245 B2 | 3/2009 | Quake et al. |
| 7,579,153 B2 | 8/2009 | Brenner et al. |
| 7,741,463 B2 | 6/2010 | Gormley et al. |
| 7,771,934 B2 | 8/2010 | Kurn |
| 7,771,946 B2 | 8/2010 | Kurn |
| 7,803,550 B2 | 9/2010 | Makarov et al. |

(56) References Cited

U.S. PATENT DOCUMENTS

| | | | |
|---|---|---|---|
| 7,846,666 B2 | 12/2010 | Kurn et al. | |
| 7,846,733 B2 | 12/2010 | Kurn | |
| 7,867,703 B2 | 1/2011 | Sampson et al. | |
| 7,939,258 B2 | 5/2011 | Kurn et al. | |
| 7,948,015 B2 | 5/2011 | Rothberg et al. | |
| 7,985,565 B2 | 7/2011 | Mayer et al. | |
| 8,017,335 B2 | 9/2011 | Smith | |
| 8,034,568 B2 | 10/2011 | Kurn et al. | |
| 8,053,192 B2 | 11/2011 | Bignell et al. | |
| 8,071,311 B2 | 12/2011 | Kurn | |
| 8,143,001 B2 | 3/2012 | Kurn et al. | |
| 8,334,116 B2 | 12/2012 | Kurn | |
| 8,465,950 B2 | 6/2013 | Kurn et al. | |
| 8,492,095 B2 | 7/2013 | Kurn | |
| 8,512,956 B2 | 8/2013 | Kurn et al. | |
| 8,551,709 B2 | 10/2013 | Kurn et al. | |
| 8,759,036 B2 * | 6/2014 | Wang | C12P 19/28 435/91.2 |
| 8,852,867 B2 | 10/2014 | Kurn et al. | |
| 8,999,677 B1 | 4/2015 | Soldatov et al. | |
| 9,175,325 B2 | 11/2015 | Kurn et al. | |
| 9,175,336 B2 | 11/2015 | Soldatov et al. | |
| 9,181,582 B2 | 11/2015 | Kurn | |
| 9,206,418 B2 | 12/2015 | Armour | |
| 9,284,602 B2 * | 3/2016 | Zhang | C12Q 1/6832 |
| 9,650,628 B2 | 5/2017 | Amorese et al. | |
| 9,745,614 B2 | 8/2017 | Schroeder et al. | |
| 2001/0000077 A1 | 3/2001 | Engelhardt et al. | |
| 2001/0031739 A1 | 10/2001 | Dare | |
| 2001/0034048 A1 | 10/2001 | Kurn | |
| 2001/0041334 A1 | 11/2001 | Rashtchian et al. | |
| 2002/0028447 A1 | 3/2002 | Lee et al. | |
| 2002/0058270 A1 | 5/2002 | Kurn | |
| 2002/0115088 A1 | 8/2002 | Kurn | |
| 2002/0150919 A1 | 10/2002 | Weissmann et al. | |
| 2002/0155451 A1 | 10/2002 | Makrigiorgos | |
| 2002/0164628 A1 | 11/2002 | Kurn | |
| 2002/0164634 A1 | 11/2002 | Patil et al. | |
| 2002/0197639 A1 | 12/2002 | Shia et al. | |
| 2003/0017591 A1 | 1/2003 | Kurn | |
| 2003/0022207 A1 | 1/2003 | Balasubramanian et al. | |
| 2003/0082543 A1 | 5/2003 | Su et al. | |
| 2003/0087251 A1 | 5/2003 | Kurn | |
| 2003/0119150 A1 | 6/2003 | Ankenbauer et al. | |
| 2003/0143555 A1 | 7/2003 | Bourget et al. | |
| 2003/0175780 A1 | 9/2003 | Jones | |
| 2003/0180779 A1 | 9/2003 | Lofton-Day et al. | |
| 2003/0186234 A1 | 10/2003 | Kurn | |
| 2003/0207279 A1 | 11/2003 | Crothers et al. | |
| 2003/0215926 A1 | 11/2003 | Kurn et al. | |
| 2003/0224439 A1 | 12/2003 | Lafferty et al. | |
| 2003/0232348 A1 | 12/2003 | Jones et al. | |
| 2004/0002371 A1 | 1/2004 | Paquin et al. | |
| 2004/0005614 A1 | 1/2004 | Kurn et al. | |
| 2004/0023271 A1 | 2/2004 | Kurn et al. | |
| 2004/0115815 A1 | 6/2004 | Li et al. | |
| 2004/0137456 A1 | 7/2004 | Yokota et al. | |
| 2004/0161742 A1 | 8/2004 | Dean et al. | |
| 2004/0203019 A1 | 10/2004 | Kurn | |
| 2004/0203025 A1 | 10/2004 | Kurn | |
| 2004/0248153 A1 | 12/2004 | Dear et al. | |
| 2005/0003441 A1 | 1/2005 | Kurn | |
| 2005/0014192 A1 | 1/2005 | Kurn | |
| 2005/0019793 A1 | 1/2005 | Kurn et al. | |
| 2005/0059048 A1 | 3/2005 | Gunderson et al. | |
| 2005/0064456 A1 | 3/2005 | Kurn | |
| 2005/0123956 A1 | 6/2005 | Blume et al. | |
| 2005/0136417 A1 | 6/2005 | Cole et al. | |
| 2005/0142577 A1 | 6/2005 | Jones et al. | |
| 2005/0191656 A1 | 9/2005 | Drmanac et al. | |
| 2005/0191682 A1 | 9/2005 | Barone et al. | |
| 2005/0208538 A1 | 9/2005 | Kurn et al. | |
| 2006/0008824 A1 | 1/2006 | Ronaghi et al. | |
| 2006/0014182 A1 | 1/2006 | Kurn | |
| 2006/0024678 A1 | 2/2006 | Buzby | |
| 2006/0024711 A1 | 2/2006 | Lapidus et al. | |
| 2006/0035274 A1 | 2/2006 | Dong | |
| 2006/0046251 A1 | 3/2006 | Sampson et al. | |
| 2006/0051789 A1 | 3/2006 | Kazakov et al. | |
| 2006/0068415 A1 * | 3/2006 | Jones | C12Q 1/6809 435/6.18 |
| 2006/0134633 A1 | 6/2006 | Chen et al. | |
| 2006/0216724 A1 | 9/2006 | Christians et al. | |
| 2006/0263789 A1 | 11/2006 | Kincaid | |
| 2006/0281082 A1 | 12/2006 | Zhu | |
| 2006/0286566 A1 | 12/2006 | Lapidus et al. | |
| 2006/0292597 A1 | 12/2006 | Shapero et al. | |
| 2007/0031857 A1 | 2/2007 | Makarov et al. | |
| 2007/0134128 A1 | 6/2007 | Korlach | |
| 2007/0141604 A1 | 6/2007 | Gormley et al. | |
| 2007/0224613 A1 | 9/2007 | Strathmann | |
| 2007/0231823 A1 | 10/2007 | McKernan et al. | |
| 2007/0238122 A1 | 10/2007 | Allbritton et al. | |
| 2008/0038727 A1 | 2/2008 | Spier | |
| 2008/0087826 A1 | 4/2008 | Harris et al. | |
| 2008/0103058 A1 | 5/2008 | Siddiqi | |
| 2008/0160580 A1 | 7/2008 | Adessi et al. | |
| 2008/0176311 A1 | 7/2008 | Kurn | |
| 2008/0182300 A1 | 7/2008 | Kurn | |
| 2008/0194413 A1 | 8/2008 | Albert | |
| 2008/0194416 A1 | 8/2008 | Chen | |
| 2008/0206764 A1 | 8/2008 | Williams et al. | |
| 2008/0213770 A1 | 9/2008 | Williams et al. | |
| 2008/0241831 A1 * | 10/2008 | Fan | C12Q 1/6844 435/6.16 |
| 2008/0242560 A1 | 10/2008 | Gunderson et al. | |
| 2008/0286795 A1 | 11/2008 | Kawashima et al. | |
| 2009/0011959 A1 | 1/2009 | Costa et al. | |
| 2009/0024331 A1 | 1/2009 | Tomaney et al. | |
| 2009/0026082 A1 | 1/2009 | Rothberg et al. | |
| 2009/0029385 A1 | 1/2009 | Christians et al. | |
| 2009/0036663 A1 | 2/2009 | Kurn | |
| 2009/0061425 A1 | 3/2009 | Lo et al. | |
| 2009/0061439 A1 | 3/2009 | Buzby | |
| 2009/0068645 A1 | 3/2009 | Sibson | |
| 2009/0068655 A1 | 3/2009 | Williams | |
| 2009/0068709 A1 | 3/2009 | Kurn et al. | |
| 2009/0105081 A1 | 4/2009 | Rodesch et al. | |
| 2009/0117573 A1 | 5/2009 | Fu et al. | |
| 2009/0117621 A1 | 5/2009 | Boutell et al. | |
| 2009/0124514 A1 | 5/2009 | Fu et al. | |
| 2009/0127589 A1 | 5/2009 | Rothberg et al. | |
| 2009/0130721 A1 | 5/2009 | Kurn et al. | |
| 2009/0203085 A1 | 8/2009 | Kurn et al. | |
| 2009/0203531 A1 | 8/2009 | Kurn et al. | |
| 2009/0233804 A1 | 9/2009 | Kurn et al. | |
| 2009/0239232 A1 | 9/2009 | Kurn et al. | |
| 2009/0275486 A1 | 11/2009 | Kurn et al. | |
| 2009/0280538 A1 | 11/2009 | Patel et al. | |
| 2009/0298075 A1 | 12/2009 | Travers et al. | |
| 2010/0015666 A1 | 1/2010 | Brenner et al. | |
| 2010/0021973 A1 | 1/2010 | Makarov et al. | |
| 2010/0022403 A1 | 1/2010 | Kurn et al. | |
| 2010/0029511 A1 * | 2/2010 | Raymond | C12Q 1/686 506/26 |
| 2010/0105052 A1 | 4/2010 | Drmanac et al. | |
| 2010/0113296 A1 | 5/2010 | Myerson | |
| 2010/0129879 A1 | 5/2010 | Ach et al. | |
| 2010/0137143 A1 | 6/2010 | Rothberg et al. | |
| 2010/0159559 A1 | 6/2010 | Kurn et al. | |
| 2010/0167954 A1 | 7/2010 | Earnshaw et al. | |
| 2010/0173394 A1 | 7/2010 | Colston, Jr. et al. | |
| 2010/0203597 A1 | 8/2010 | Chen et al. | |
| 2010/0273219 A1 | 10/2010 | May et al. | |
| 2010/0311066 A1 | 12/2010 | Kurn | |
| 2010/0323348 A1 | 12/2010 | Hamady et al. | |
| 2011/0015096 A1 | 1/2011 | Chiu | |
| 2011/0039732 A1 | 2/2011 | Raymond et al. | |
| 2011/0104785 A1 | 5/2011 | Vaidyanathan et al. | |
| 2011/0105364 A1 | 5/2011 | Kurn | |
| 2011/0129827 A1 | 6/2011 | Causey et al. | |
| 2011/0189679 A1 | 8/2011 | Kurn et al. | |
| 2011/0224105 A1 * | 9/2011 | Kurn | C12P 19/34 506/26 |

(56) References Cited

U.S. PATENT DOCUMENTS

| | | |
|---|---|---|
| 2011/0288780 A1 | 11/2011 | Rabinowitz et al. |
| 2011/0294132 A1 | 12/2011 | Kurn et al. |
| 2011/0319290 A1 | 12/2011 | Raymond et al. |
| 2012/0003657 A1 | 1/2012 | Myllykangas et al. |
| 2012/0028310 A1 | 2/2012 | Kurn et al. |
| 2012/0045797 A1 | 2/2012 | Kurn et al. |
| 2012/0071331 A1 | 3/2012 | Casbon et al. |
| 2012/0074925 A1 | 3/2012 | Oliver |
| 2012/0102054 A1 | 4/2012 | Popescu et al. |
| 2012/0122701 A1 | 5/2012 | Ryan et al. |
| 2012/0149068 A1 | 6/2012 | Kurn et al. |
| 2012/0156728 A1 | 6/2012 | Li et al. |
| 2012/0157322 A1 | 6/2012 | Myllykangas et al. |
| 2012/0190587 A1 | 7/2012 | Kurn et al. |
| 2012/0220483 A1 | 8/2012 | Kurn et al. |
| 2012/0237943 A1 | 9/2012 | Soldatov et al. |
| 2012/0238738 A1 | 9/2012 | Hendrickson |
| 2012/0245041 A1 | 9/2012 | Brenner et al. |
| 2012/0270212 A1 | 10/2012 | Rabinowitz et al. |
| 2012/0283145 A1 | 11/2012 | Wang |
| 2012/0289426 A1 | 11/2012 | Roos et al. |
| 2012/0309002 A1 | 12/2012 | Link |
| 2013/0059738 A1 | 3/2013 | Leamon et al. |
| 2013/0231253 A1 | 9/2013 | Amorese et al. |
| 2014/0038188 A1 | 2/2014 | Kurn |
| 2014/0038236 A1 | 2/2014 | Kurn et al. |
| 2014/0065692 A1 | 3/2014 | Kurn et al. |
| 2014/0274729 A1 | 9/2014 | Kurn et al. |
| 2014/0274731 A1 | 9/2014 | Raymond et al. |
| 2014/0274738 A1 | 9/2014 | Amorese et al. |
| 2014/0303000 A1 | 10/2014 | Armour |
| 2014/0378345 A1 | 10/2014 | Hindson et al. |
| 2015/0011396 A1 | 1/2015 | Schroeder et al. |
| 2015/0017635 A1 | 1/2015 | Myllykangas et al. |
| 2015/0284769 A1 | 10/2015 | Schroeder |
| 2016/0040215 A1 | 2/2016 | Henn et al. |
| 2016/0122756 A1 | 5/2016 | Armour |
| 2016/0130576 A1 | 5/2016 | Armour |
| 2016/0153039 A1 | 6/2016 | Amorese et al. |
| 2016/0251711 A1 | 9/2016 | Amorese et al. |
| 2016/0251712 A1 | 9/2016 | Amorese et al. |
| 2016/0265042 A1 | 9/2016 | Schroeder et al. |
| 2016/0275240 A1 | 9/2016 | Huelga et al. |
| 2017/0298345 A1 | 10/2017 | Amorese et al. |

FOREIGN PATENT DOCUMENTS

| | | | |
|---|---|---|---|
| EP | 0329822 B1 | 6/1994 | |
| EP | 0667393 A2 | 8/1995 | |
| EP | 0667393 A3 | 11/1995 | |
| EP | 1071811 B1 | 3/2002 | |
| EP | 0843735 B1 | 7/2002 | |
| EP | 2272976 A1 | 1/2011 | |
| EP | 2322612 A1 | 5/2011 | |
| EP | 2451973 A1 | 5/2012 | |
| WO | WO 92/07951 A1 | 5/1992 | |
| WO | WO 93/18052 A1 | 9/1993 | |
| WO | WO 94/16090 A1 | 7/1994 | |
| WO | WO 96/40998 A1 | 12/1996 | |
| WO | WO 9640998 A1 * | 12/1996 | ........... C07K 14/415 |
| WO | WO 97/12061 A1 | 4/1997 | |
| WO | WO 97/25416 A2 | 7/1997 | |
| WO | WO 97/25416 A3 | 10/1997 | |
| WO | WO 98/06736 A1 | 2/1998 | |
| WO | WO 98/38296 A1 | 9/1998 | |
| WO | WO 98/44151 A1 | 10/1998 | |
| WO | WO 99/10540 A1 | 3/1999 | |
| WO | WO 99/11819 A1 | 3/1999 | |
| WO | WO 99/42618 A1 | 8/1999 | |
| WO | WO 00/08208 A2 | 2/2000 | |
| WO | WO 2000/09756 A1 | 2/2000 | |
| WO | WO 00/08208 A3 | 5/2000 | |
| WO | WO 00/018957 A1 | 6/2000 | |
| WO | WO 00/39345 A1 | 7/2000 | |
| WO | WO 00/52191 A1 | 9/2000 | |
| WO | WO 2000/55364 A2 | 9/2000 | |
| WO | WO 00/70039 A1 | 11/2000 | |
| WO | WO 01/20035 A2 | 3/2001 | |
| WO | WO 01/23613 A1 | 4/2001 | |
| WO | WO 01/46464 A1 | 6/2001 | |
| WO | WO 01/57248 A2 | 8/2001 | |
| WO | WO 01/64952 A2 | 9/2001 | |
| WO | WO 2000/55364 A3 | 10/2001 | |
| WO | WO 01/20035 A3 | 12/2001 | |
| WO | WO 02/00938 A2 | 1/2002 | |
| WO | WO 01/57248 A3 | 2/2002 | |
| WO | WO 02/28876 A2 | 4/2002 | |
| WO | WO 02/29117 A2 | 4/2002 | |
| WO | WO 02/36821 A2 | 5/2002 | |
| WO | WO 02/48402 A2 | 6/2002 | |
| WO | WO 02/28876 A3 | 8/2002 | |
| WO | WO 02/060318 A2 | 8/2002 | |
| WO | WO 02/072772 A2 | 9/2002 | |
| WO | WO 02/072773 A2 | 9/2002 | |
| WO | WO 02/081753 A1 | 10/2002 | |
| WO | WO 02/090584 A2 | 11/2002 | |
| WO | WO 01/64952 A3 | 12/2002 | |
| WO | WO 2003/002736 A2 | 1/2003 | |
| WO | WO 2003/012118 A1 | 2/2003 | |
| WO | WO 02/36821 A3 | 3/2003 | |
| WO | WO 03/027259 A2 | 4/2003 | |
| WO | WO 02/00938 A3 | 8/2003 | |
| WO | WO 02/29117 A3 | 8/2003 | |
| WO | WO 02/072772 A3 | 9/2003 | |
| WO | WO 02/090584 A3 | 9/2003 | |
| WO | WO 03/078645 A2 | 9/2003 | |
| WO | WO 02/060318 A3 | 10/2003 | |
| WO | WO 03/083435 A2 | 10/2003 | |
| WO | WO 02/072773 A3 | 12/2003 | |
| WO | WO 03/027259 A3 | 12/2003 | |
| WO | WO 03/106642 A2 | 12/2003 | |
| WO | WO 03/083435 A3 | 2/2004 | |
| WO | WO 03/078645 A3 | 3/2004 | |
| WO | WO 02/48402 A3 | 4/2004 | |
| WO | WO 04/011665 A2 | 9/2004 | |
| WO | WO 2004/092418 A2 | 10/2004 | |
| WO | WO 03/106642 A3 | 11/2004 | |
| WO | WO 04/011665 A3 | 7/2005 | |
| WO | WO 2005/065321 A2 | 7/2005 | |
| WO | WO 2006/081222 A2 | 8/2006 | |
| WO | WO 2006/086668 A2 | 8/2006 | |
| WO | WO 2006/081222 A3 | 2/2007 | |
| WO | WO 2007/018601 A1 | 2/2007 | |
| WO | WO 2007/019444 A2 | 2/2007 | |
| WO | WO 2007/030759 A2 | 3/2007 | |
| WO | WO 2007/052006 A1 | 5/2007 | |
| WO | WO 2007/057652 A1 | 5/2007 | |
| WO | WO 2007/030759 A3 | 6/2007 | |
| WO | WO 2007/136717 A1 | 11/2007 | |
| WO | WO 2008/005459 A2 | 1/2008 | |
| WO | WO 2008/005459 A3 | 2/2008 | |
| WO | WO 2008/015396 A2 | 2/2008 | |
| WO | WO 2008/033442 A2 | 3/2008 | |
| WO | WO 2008/115185 A2 | 9/2008 | |
| WO | WO 2008/033442 A3 | 10/2008 | |
| WO | WO 2008/115185 A3 | 12/2008 | |
| WO | WO 2009/053039 A1 | 4/2009 | |
| WO | WO 2005/065321 A3 | 5/2009 | |
| WO | WO 2009/102878 A2 | 8/2009 | |
| WO | WO 2009/102896 A2 | 8/2009 | |
| WO | WO 2009/112844 A1 | 9/2009 | |
| WO | WO 2009/117698 A2 | 9/2009 | |
| WO | WO 2009/120372 A2 | 10/2009 | |
| WO | WO 2009/120374 A2 | 10/2009 | |
| WO | WO 2009/120374 A3 | 12/2009 | |
| WO | WO 2009/120372 A3 | 1/2010 | |
| WO | WO 2010/003153 A2 | 1/2010 | |
| WO | WO 2010/030683 A1 | 3/2010 | |
| WO | WO 2010/039991 A2 | 4/2010 | |
| WO | WO 2010/063711 A1 | 6/2010 | |
| WO | WO 2010/064893 A1 | 6/2010 | |
| WO | WO 2010/085715 A1 | 7/2010 | |
| WO | WO 2010/115154 A1 | 10/2010 | |
| WO | WO 2010/129937 A2 | 11/2010 | |

(56) References Cited

FOREIGN PATENT DOCUMENTS

| | | |
|---|---|---|
| WO | WO 2011/003630 A1 | 1/2011 |
| WO | WO 2011/009941 A1 | 1/2011 |
| WO | WO 2011/019964 A1 | 2/2011 |
| WO | WO 2011/032053 A1 | 3/2011 |
| WO | WO 2011/053987 A1 | 5/2011 |
| WO | WO 2011/151777 A1 | 12/2011 |
| WO | WO 2011/156529 A2 | 12/2011 |
| WO | WO 2012/013932 A1 | 2/2012 |
| WO | WO 2012/103154 A1 | 8/2012 |
| WO | WO 2013/059740 A1 | 4/2013 |
| WO | WO 2013/112923 A1 | 8/2013 |
| WO | WO 2013/177220 A1 | 11/2013 |
| WO | WO 2013/191775 A2 | 12/2013 |
| WO | WO 2014/144092 A1 | 9/2014 |
| WO | WO 2014/150931 A1 | 9/2014 |
| WO | WO 2015/131107 A1 | 9/2015 |

OTHER PUBLICATIONS

Office action dated Apr. 16, 2014 for U.S. Appl. No. 13/239,226.
Office action dated Sep. 24, 2014 for U.S. Appl. No. 13/239,226.
Briggs, et al. Targeted retrieval and analysis of five Neandertal mtDNA genomes. Science. Jul. 17, 2009;325(5938):318-21. doi: 10.1126/science.1174462.
Karow. New Capture Method Enables MPI Team to Sequence Five Neandertal Mitochondrial Genomes. GenomeWeb. Jul. 21, 2009. https://www.genomeweb.com/sequencing/new-capture-method-enables-mpi-team-sequence-five-neandertal-mitochondrial-genom.
Xiao, et al. Sequential amplification of flanking sequences by Y-shaped adaptor dependent extension using multiple templates. Zhi Wu Sheng Li Yu Fen Zi Sheng Wu Xue Xue Bao (Journal of Plant Physiology and Molecular Biology). Feb. 2007;33(1):85-90.
Zheng, et al. Titration-free 454 sequencing using Y adapters. Nat Protoc. Aug. 18, 2011;6(9):1367-76. doi: 10.1038/nprot.2011.369.
U.S. Appl. No. 15/047,448, filed Feb. 18, 2016, Huelga et al.
Zhang, et al. Copy number variation in human health, disease, and evolution. Annu Rev Genomics Hum Genet. 2009;10:451-81. doi: 10.1146/annurevgenom.9.081307.164217.
U.S. Appl. No. 14/634,326, filed Feb. 27, 2015, Schroeder.
Ahmed. Sequencing of Low-Diversity Libraries. Feb. 28, 2012. http://cofactorgenomicas.com/sequencing-low-diversity-libraries/.
Diagnosing problems with phasing and pre-phasing on Illumina platforms. Loman Labs. Nov. 21, 2013. http://nickloman.github.io/high-throughput%20sequencing/2013/11/21/diagnosing-problems-with-phasing-and-pre-phasing-on-illumina-platforms/.
Fadrosh, et al. An improved dual-indexing approach for multiplexed 16S rRNA gene sequencing on the Illumina MiSeq platform. Microbiome. Feb. 24, 2014;2(1):6. doi: 10.1186/2049-2618-2-6.
Faircloth, et al. Not all sequence tags are created equal: designing and validating sequence identification tags robust to indels. PLoS One. 2012;7(8):e42543. doi: 10.1371/journal.pone.0042543. Epub Aug. 10, 2012.
Gu, et al. Preparation of reduced representation bisulfate sequencing libraries for genome-scale DNA methylation profiling. Nat Protoc. Apr. 2011;6(4):468-81. doi: 10.1038/nprot.2010.190. Epub Mar. 18, 2011.
Kozich, et al. Development of a dual-index sequencing strategy and curation pipeline for analyzing amplicon sequence data on the MiSeq Illumina sequencing platform. Appl Environ Microbiol. Sep. 2013;79(17):5112-20. doi: 10.1128/AEM.01043-13. Epub Jun. 21, 2013.
Krueger, et al. Large scale loss of data in low-diversity illumina sequencing libraries can be recovered by deferred cluster calling. PLoS One. Jan. 28, 2011;6(1):e16607. doi: 10.1371/journal.pone.0016607.
Krueger. Loss of data in low-diversity libraries can be recovered by deferred cluster calling. Poster Jan. 29, 2011. http://seqanswers.com/forums/showthread.php?t=9150.
Leonard. What is a reliable method for multiplexing more than 384 samples on a MiSeq run? Posted Aug. 19, 2013. http://www.researchgate.net/post/What_is_a_reliable_method_for_multiplexing_more_than_384_samples_on_aMiSeq_run2.
Nextera® Rapid Capture Enrichment Low-Plex Pooling Guidelines. Technical Note: DNA Analysis. 2014. http://www.illumina.com/content/dam/illumina-marketing/documents/products/technotes/technote-nextera-rapid-capture-low-plex-pooling-guidelines.pdf.
Office action dated Mar. 9, 2015 for CN Application No. 201380006942.4.
SEQanswers. MiSeq cluster generation problems. Posted Mar. 17, 2012. http://seqanswers.com/forums/showthread.php?t=18499.
SEQanswers. Sequencing a Low diversity library on the HiSeq. Posted Nov. 18, 2011. http://seqanswers.com/forums/showthread.php?t=18499.
Singapore written opinion dated Mar. 17, 2015 for SG Application No. 11201401628W.
Wu, et al. Phasing Amplicon Sequencing for Robust Microbial Community Analysis. 1-2630. 2014. http://www.asmonlineeducation.com/php/asm2014abstracts/data/papers/I-2630.htm.
U.S. Appl. No. 15/154,414, filed May 13, 2016, Armour et al.
Bradford, et al. A comparison of massively parallel nucleotide sequencing with oligonucleotide microarrays for global transcription profiling. BMC Genomics. May 5, 2010;11:282. doi: 10.1186/1471-2164-11-282.
Gerrish, et al. Tailed pooled suppression subtractive hybridization (PSSH) adaptors do not alter efficiency. Antonie Van Leeuwenhoek. Nov. 2010;98(4):573-9. doi: 10.1007/s10482-010-9465-x. Epub Jun. 8, 2010.
Gu, et al. Depletion of Abundant Sequences by Hybridization (DASH): using Cas9 to remove unwanted high-abundance species in sequencing libraries and molecular counting applications. Genome Biology. 2016; 17:41. DOI: 10.1186/s13059-016-0904-5.
Hurd, et al. Advantages of next-generation sequencing versus the microarray in epigenetic research. Brief Funct Genomic Proteomic. May 2009;8(3):174-83. doi: 10.1093/bfgp/elp013. Epub Jun. 17, 2009.
Office action dated Jun. 2, 2016 for U.S. Appl. No. 13/750,768.
Office action dated Jul. 21, 2016 for U.S. Appl. No. 14/634,326.
Olivarius, et al. High-throughput verification of transcriptional starting sites by Deep-RACE. Biotechniques. Feb. 2009;46(2):130-2. doi: 10.2144/000113066.
Oyola, et al. Efficient Depletion of Host DNA Contamination in Malaria Clinical Sequencing. J. Clin. Microbiol. Mar. 2013; 51(3):745-751.
Rothberg, et al. An integrated semiconductor device enabling non-optical genome sequencing. Nature. Jul. 20, 2011;475(7356):348-52. doi: 10.1038/nature10242. With supplemental information.
European search report and opinion dated Sep. 1, 2016 for EP Application No. 14764629.3.
Stewart, et al. Complete MHC Haplotype Sequencing for Common Disease Gene Mapping. Genome Res. Jun. 2004;14(6):1176-87. Epub May 12, 2004.
Amorese, et al. Improved pathogen sequencing of host-pathogen RNA-sequence. AGBT 2016. Advances in Genome Biology Technology Conference. Feb. 10, 2016. Orlando, FL. Nugen Technologies. Poster Presentation. 2 pages.
Li, et al. Targeted depletion of host reads in host-pathogen mixed RNA-seq libraries. Advances in Genome Biology Technology Conference. Feb. 11, 2016. Orlando, FL. Nugen Technologies. Poster. 1 page.
Notice of allowance dated Jan. 5, 2017 for U.S. Appl. No. 13/750,768.
Office Action dated Oct. 31, 2016 for European Application 13806978.6.
U.S. Appl. No. 13/938,059, filed Jul. 9, 2013, Schroeder et al.
U.S. Appl. No. 13/980,987, filed Jul. 22, 2013, Kurn et al.
U.S. Appl. No. 14/012,409, filed Aug. 28, 2013, Kurn et al.
AB Applied Biosystems. The solid 3 system enabling the next generation of science. Presentation. 2009.
Adamczyk, et al. Synthesis of a Chemiluminescent Acridinium Hydroxylamine (AHA) for the Direct Detection of Abasic Sites in DNA. Org. Lett. 1999; 1(5):779-781.

(56) References Cited

OTHER PUBLICATIONS

Adamczyk, et al. O-(Fluoresceinylmethyl) hydroxylamine (OFMHA): A Fluorescent Regent for Detection of Damaged Nucleic Acids. Bioorg. & Med. Chem. Lett. 1998; 8:3599-3602.

Adessi, et al., Solid phase DNA amplification: characterisation of primer attachment and ampflication mechanisms. Nucleic Acids Research. Oct. 15, 2000. 28:(20): e87.

Agilent Technologies. Agilent Technologies adds human exon kit to next-generation-sequencing target enrichment portfolio. GenomicsNews.com. Posted 2009 Sep. 23, 2009. Avaialble at http://www.genomicsnews.com/index.aspx?ID=103607&sm=Agilent%20technologies%20adds%20human%20exo. Accessed Oct. 6, 2009.

Albert, et al. Direct selection of human genomic loci by microarray hybridization. Nat Methods. Nov. 2007;4(11):903-5. Epub Oct. 14, 2007.

Anisimova, et al. Isolation, characterization and molecular cloning of duplex-specific nuclease from the hepatopancreas of the kamchatka crab. BMC Biochemistry. May 21, 2008. 9:14 doi10.1186/1471-2091-9-14.

Antson, et al. PCR-generated padlock probes detect single nucleotide variation in genomic DNA. Nucleic Acids Res. Jun. 15, 2000;28(12):E58.

Anwar, et al. A stem—loop-mediated reverse transcription real-time PCR for the selective detection and quantification of the replicative strand of an RNA virus. Anal Biochem. May 1, 2006;352(1):120-8. Epub Feb. 17, 2006.

Archer, et al. Selective and flexible depletion of problematic sequences from RNA-seq libraries at the cDNA stage. BMC Genomics. May 26, 2014;15:401. doi: 10.1186/1471-2164-15-401.

Arraystar, Inc. Arraystar Directional RNA-seq Prep Kit (dUTP Based). Cat#: A1208. Apr. 8, 2013.

Ausubel, et al., Eds. Current Protocols in Molecular Biology. John Wiley & Sons, Inc. 1987 and updates.

Baird, et al. Rapid SNP discovery and genetic mapping using sequenced RAD markers. PLoS One. 2008;3(10):e3376.

Ballestar, et al. Methyl-CpG-binding proteins. Targeting specific gene repression. Eur J Biochem 2001; 268:1-6.

Bangs Laboratories, Inc. TechNote 205 retreived at: http:www.bangslab.com/technotes/205.pdf . Visited on Jul. 16, 2003. (8 pages).

Bashiardes, et al. Direct genomic selection. Nat Methods. Jan. 2005;2(1):63-9.

Beaucage, et al. The functionalization of oligonucleotides via phosphoramidite derivative. Tetrahedron. 1993;49(10):1925-63.

Beier, et al. HT sequencing in biomedicine—new approaches in preparing samples. LABORWELT. Jan. 9, 2008.

Ben-Artzi, et al. Double-stranded RNA-dependent RNase activity associated with human immunodeficiency virus type 1 reverse transcriptase. Proc Natl Acad Sci U S A. Feb. 1, 1992;89(3):927-31.

Bentley, D. R. Whole-genome re-sequencing. Curr Opin Genet Dev. Dec. 2006;16(6):545-52. Epub Oct. 18, 2006.

Bhattacharjee, et al. Complementing next generation sequencing technologies with Agilent's SureSelect DNA capture array. Agilent. Jul. 13, 2009.

Bibikova, et al. Targeted chromosomal cleavage and mutagenesis in drophila using zinc-finger nucleases genetics. Genetics. Jul. 2002 161: 1169-1175.

Bioo Scientific. Illumina RNA-Seq Library Prep. Available at http://www.biooscientific.com/ProductsServices/NextGenSequencing/Illumina-Compatible/RNA-Seq.aspx. Accessed Jun. 16, 2014.

Bioo Scientific. NEXTflex RNA-Seq Kit. Available at http://www.biooscientific.com/ProductsServices/NextGenSequencing/Illumina-Compatible/RNA-Seq/NEXTflex%E2%84%A2RNA-SeqKit.aspx. Accessed Jun. 16, 2014.

Blow, N. Genomics: catch me if you can. Nature Methods.Jul. 2009. 6:7.539-544.

Bormann, et al. Whole methylome analysis by ultra-deep sequencing using two-base encoding. PLoS One. Feb. 22, 2010;5(2):e9320.

Borodina, et al. A strand-specific library preparation protocol for RNA sequencing. Methods Enzymol. 2011;500:79-98. doi: 10.1016/B978-0-12-385118-5.00005-0.

Boturyn, et al. A simple and Sensitive Method for in Vitro Quantitation of Abasic Sites in DNA. Chem. Res. Toxicol. 1999; 12:476-482.

Boturyn, et al. Synthesis of Fluorescent Probes for the Detection of Abasic Sites in DNA. Tetrahedron. 1997; 53(15):5485-5492.

Brill, et al. Synthesis of oligodeoxynucleoside phosphorodithioates via thioamidites. J. Am. Chem. Soc. 1989;111:2321-2322.

Broude. Stem-loop oligonucleotides: a robust tool for molecular biology and biotechnology. Trends Biotechnol. Jun. 2002;20(6):249-56.

Brown, T.A. Ed. Molecular Biology, LabFax. Bios Scientific Publishers. Academic Press. 1991; pp. 147-148.

Buchman, et al. Selective RNA amplification: a novel method using dUMP-containing primers and uracil DNA glycosylase. PCR Methods Appl. Aug. 1993;3(1):28-31.

Burrows, et al. Oxidative Nucleobase Modifications Leading to Strand Scission. Chem Rev. May 7, 1998;98(3):1109-1151.

Carey, et al. Human Apurinic/Apyrimidinic Endonuclease in Processive. Biochem. 1999; 38:16553-16560.

Carlsson, et al. Screening for genetic mutations. Nature. 1996;380(6571):207.

Chan, et al. The biophysics of DNA hybridization with immobilized oligonucleotide probes. Biophys J. Dec. 1995;69(6):2243-55.

Chen, et al. Real-time quantification of microRNAs by stem-loop RT-PCR. Nucleic Acids Res. Nov. 27, 2005;33(20):e179.

Clontech Laboratories, Inc. In-Fusion SMARTer Directional cDNA Library Construction Kit User Manual. Cat. No. 634933. Copyright 2013.

Cofactor genomics. Directional RNA Sequencing. Abailable at http://cofactorgenomics.com/directional-rna-sequencing. Accessed Jun. 4, 2014.

Combined search and examination report dated Apr. 24, 2013 for GB1305340.

Craig, et al. Identification of genetic variants using bar-coded multiplexed sequencing. Nat Methods. Oct. 2008;5(10):887-93.

Croucher, et al. A simple method for directional transcriptome sequencing using Illumina technology. Nucleic Acids Res. Dec. 2009;37(22):e148.

Dahl, et al. Multigene amplification and massively parallel sequencing for cancer mutation discovery. Proc Natl Acad Sci U S A. May 29, 2007;104(22):9387-92. Epub May 17, 2007.

Dahl, et al. Multiplex amplification enabled by selective circularization of large sets of genomic DNA fragments. Nucleic Acids Res. Apr. 28, 2005;33(8):e71.

Dempcy, et al. Synthesis of a thymidyl pentamer of deoxyribonucleic guanidine and binding studies with DNA homopolynucleotides. Proc Natl Acad Sci USA. 1995;92(13):6097-101.

Derisi, et al. Use of cDNA microarray to analyse gene expression patterns in human cancer. Nature Genetics. 1996; 14:457-460.

Dressman, et al., Transforming single DNA molecules into fluorescent magnetic particles for detection and enumeration of genetic variations. Proc Natl Sci USA. Jul. 22, 2003 100(15): 8817-8822.

Drmanac, et al. Human genome sequencing using unchained base reads on self-assembling DNA nanoarrays. Science. Jan, 1, 2010;327(5961):78-81. doi: 10.1126/science.1181498. Epub Nov. 5, 2009.

Egholm, et al. Peptide nucleic acids (PNA) oligonucleotide analogues with an achiral peptide backbone. J. Am. Chem. Soc. 1992;114:1895-1897.

Egholm, et al. PNA hybridizes to complementary oligonucleotides obeying the Watson-Crick hydrogen-bonding rules. Nature. 1993;365(6446):566-8.

Erlanger, et al. Antibodies Specific for Ribonucleosides and Ribonucleotides and Their Reaction With DNA. Proc Natl Acad Sci USA. 1964; 52:68-74.

Esteller. Cancer epigenomics: DNA methylomes and histone-modification maps. Nat Rev Genet. Apr. 2007;8(4):286-98. Epub Mar. 6, 2007.

(56) References Cited

OTHER PUBLICATIONS

European office action dated Apr. 1, 2011 for Application No. 03771533.1.
European search report and opinion dated Nov. 28, 2013 for EP Application No. 11793123.8.
European search report and search opinion dated Apr. 3, 2013 for Application No. 10808789.1.
European search report dated Oct. 18, 2007 for Application No. 3771533.1.
European search report dated Feb. 12, 2010 for Application No. 7810169.8.
European search report dated Mar. 29, 2010 for Application No. 4815722.6.
Fahy, et al., Self-sustained sequence replication (3SR): an isothermal transcription-based amplication system alternative to PCR. Genome Res. 1991. 1:25-33.
Feinberg, et al. Hypomethylation distinguishes genes of some human cancers from their normal counterparts. Nature. Jan. 6, 1983;301(5895):89-92.
Fodor, et al. Light-Directed, spatially addressable parallel chemical synthesis. 1991; 251: 767-773.
Franca, et al. Optimizing a qPCR gene expression quantification assay for S. epidermidis biofilms: a comparison between commercial kits and a customized protocol. PLoS One. 2012;7(5):e37480. doi: 10.1371/journal.pone.0037480. Epub May 21, 2012.
Frank. Barcrawl and Bartab: software tools for the design and implementation of barcoded primers for highly multiplexed DNA sequencing. BMC Bioinfotmatics. Oct. 29, 2009;10:362.
Fredriksson, et al. Multiplex amplification of all coding sequences within 10 cancer genes by Gene-Collector. Nucleic Acids Res. 2007;35(7):e47. Epub Feb. 22, 2007
Freeman, et al. Fundamentals of DNA Hybridization Arrays for Gene Expression Analysis. BioTechniques. Nov. 2000; 29:1042-1044, 1046, 1048-1055.
Freshney, R.I. ed. (1987). Animal Cell Culture. IRL Press: Oxford, pp. vii-xii (Table of Contents Only.).
Fujiwara, et al. Direct probing: covalent attachment of probe DNA to double-stranded target DNA. Nucleic Acids Res. Dec. 15, 1998;26(24):5728-33.
Fullwood, et al. Next-generation DNA sequencing of paired-end tags (PET) for transcriptome and genome analyses. Genome Research Open Access. 2009. Available at http://genome.cshlp.org/content/19/4/521.long. Accessed Oct. 6, 2009.
Gait, M.J., Ed. 1984 . Oligonucleotide Synthesis: A Practical Approach. IRL Press: Oxford, pp. vii-xii (Table of Contents).
Gertz, et al. Transposase mediated construction of RNA-seq libraries. Genome Res. Jan. 2012;22(1):134-41. doi: 10.1101/gr.127373.111. Epub Nov. 29, 2011.
Ghosh, S.S. Synthesis of 5'-Oligonucleotide Hydrazide Derivatives and Their Use in Preparation of Enzyme-Nucleic Acid Hybridization Probes. Anal. Biochem. 1989; 178:43-51.
Gnirke, et al. Solution hybrid selection with ultra-long oligonucleotides for massively parallel targeted sequencing. Nature Biotechnology. Feb. 2009; 27(2):182-9.
Gu, et al. Partitioning the c. elegans genome by nucleosome modification, occupancy, and position. Online Aug. 25, 2009. http://www.springerlink.com/content/r0gw044155823242/fulltext.pdf. Accessed Oct. 6, 2009.
Haraguchi, et al. Synthesis and characterization of oligodeoxynucleotides containing formamidopyrimidine lesions and nonhydrolyzable analogues. J Am Chem Soc. Apr. 3, 2002;124(13):3263-9.
Heimgartner, et al.Polyacrylic Polyhydrazides as Reagents for Detection of Glycoproteins. Anal. Biochem. 1989; 181:182-189.
Hodges, et al. Genome-wide in situ exon capture for selective resequencing. Nat Genet. Dec. 2007;39(12):1522-7. Epub Nov. 4, 2007.
Hodges, et al. Hybrid selection of discrete genomic intervals on custom-designed microarrays for massively parallel sequencing. Nat. Protoc. 2009; 4(6): 960-974.
Hollis, et al. Structural studies of human alkyladenine glycosylase and E. coli 3-methyladenine glycosylase.Mutat Res. 2000; 460(3-4):201-10.
Horn, et al. Solid supported hydrolysis of apurinic sites in synthetic oligonucleotides for rapid and efficient purification on reverse-phase cartridges. Nucl. Acids Res. 1988; 16:11559-11571.
Hottiger, et al. Strand displacement activity of the human immunodeficiency virus type 1 reverse transcriptase heterodimer and its individual subunits. J Biol Chem. Jan. 14, 1994;269(2):986-91.
Huber, et al. Processing of the primer for plus strand DNA synthesis by human immunodeficiency virus 1 reverse transcriptase. J Biol Chem. Jun. 25, 1990;265(18):10565-73.
Ide, et al. Synthesis and Damage Specificity of a Novel Probe for the Detection of Abasic Sites in DNA. Biochem. 1993; 32:8276-8283.
Illumina Inc. Directional mRNA-Seq Sample Preparation—Application to prepare directional (strand specific) sample from mRNA. Oct. 2010.
International Preliminary Examination Report dated Mar. 22, 2006 for PCT Patent Application No. PCT/US03/15825 filed May 19, 2003, 9pages.
International search report and written opinion dated Jan. 27, 2012 for PCT Application No. US2011/039683.
International search report and written opinion dated Feb. 12, 2013 for PCT/US2012/061218.
International search report and written opinion dated Feb. 24, 2011 for PCT Application No. US10/55137.
International search report and written opinion dated Apr. 16, 2013 for PCT Application No. US2013/023278.
International search report and written opinion dated May 10, 2012 for PCT Application No. US2012/22448.
International search report and written opinion dated Jul. 15, 2014 for PCT Application No. US2014/028356.
International search report and written opinion dated Jul. 29, 2014 for PCT Application No. US2014/24581.
International search report and written opinion dated Oct. 18, 2013 for PCT Application No. US2013/032606.
International search report and written opinion dated Dec. 3, 2010 for PCT Application No. US10-45384.
International search report dated Jan. 2, 2008 for PCT Application No. US2007/15409.
International search report dated Jun. 14, 2005 for PCT Application No. US 2003/015825.
International search report dated Jul. 9, 2008 for PCT Application No. US2004/043710.
Jenkins, et al. The biosynthesis of carbocyclic nucleosides. Chem. Soc. Rev. 1995;169-176.
Jones, et al. The epigenomics of cancer. Cell. Feb. 23, 2007;128(4):683-92.
Kaboev, et al. PCR hot start using primers with the structure of molecular beacons (hairpin-like structure). Nucleic Acids Res. Nov. 1, 2000;28(21):E94.
Karata, et al. Construction of a circular single-stranded DNA template containing a defined lesion. DNA Repair (Amst). Jul. 4, 2009;8(7):852-6.
Kawarada, et al. Antibodies Specific for Methylated DNA Elicited in Rabbits Recognize only a Single Strand Region of DNA Containing 7-Methylguanine. Tohuku. J Exp Med. 1986; 149:151-161.
Khrapko, et al. A method for DNA sequencing by hybridization with oligonucleotide matrix. DNA Sequence—J. DNA Sequencing and Mapping. 1991; 1:375-388.
Kiedrowski, et al. Parabolic growth of a self-replicating hexadeoxynucleotide bearing a 3'-5'-phosphoamidate linkage. Angew. Chem. Intl. Ed. English 1991;30:423-426.
Kim, et al. Evidence for thiol-dependent production of oxygen radicals by 4-methyl-5-pyrazinyl-3H-1,2-dithiole-3-thione (oltipraz) and 3H-1,2-dithiole-3-thione: possible relevance to the anticarcinogenic properties of 1,2-dithiole-3-thiones. Chem Res Toxicol. Mar. 1997;10(3):296-301.
Koshkin, et al. LNA (Locked Nucleic Acid): An RNA mimic forming exceedingly stable LNA:LNA duplexes. J. Am. Chem. Soc. 1998; 120:13252-3.
Kow, et al. Detection of Abasic Sites and Oxidative DNA Base Damage Using an ELISA-like Assay. Methods. 2000; 22:164-169.

(56) References Cited

OTHER PUBLICATIONS

Krishnakumar, et al. A comprehensive assay for targeted multiplex amplification of human DNA sequences. Proc Natl Acad Sci U S A. Jul. 8, 2008;105(27):9296-301. doi: 10.1073/pnas.0803240105. Epub Jul. 2, 2008.
Krueger, et al. Bismark: a flexible aligner and methylation caller for Bisulfite-Seq applications. Bioinformatics. Jun. 1, 2011;27(11):1571-2. doi: 10.1093/bioinformatics/btr167. Epub Apr. 14, 2011.
Kubo, et al. A Novel Sensitive, and Specific Assay for Abasic Sites, the Most Commonly Produced DNA Lesion. Biochem. 1992; 31:3703-3708.
Kumar, et al. A High-Throughput Method for Illumina RNA-Seq Library Preparation. Front Plant Sci. Aug. 28, 2012;3:202. doi: 10.3389/fpls.2012.00202. eCollection 2012.
Kurn. Method for generation of double stranded cDNA from RNA targets useful for global amplification, sequencing or other quantification of short RNA in a sample. Mar. 21, 2010. 1-5.
Laird. Principles and challenges of genomewide DNA methylation analysis. Nat Rev Genet. Mar. 2010;11(3):191-203. doi: 10.1038/nrg2732.
Lao, et al. Real time PCR profiling of 330 human micro-RNAs. Biotechnol J. Jan. 2007;2(1):33-5.
LC Sciences. Targeted sequencing—sample enrichment service. 2009. Available at www.lcsciences.com/products/genomics/targeted_sequencing/targeted_sequencing.html . Accessed Oct. 6, 2009.
LC Sciences. Technology—Massively parallel oligonucleotide and peptide synthesis on a micrchip based on the uParaflo microfluidic technology. Available at www.lcsciences.com/support/technology/technology.html. Accessed Oct. 6, 2009.
LC Sciences. Oligonucleotide mixture. OligoMix. 2009. Available at www.lcsciences.com/products/genomics/oligomix/oligomix_detail.html. Accessed Oct. 6, 2009.
Leamon, et al., a Massively parallel Pico TiterPlate based platform for discrete picoliter-scale polymerase chain reactions [abstract]. Electrophoresis. Nov. 24, 2006(21) 3769-77.
Lefrancois, et al. Efficient yeast ChIP-Seq using multiplex short-read DNA sequencing. BMC Genomics. Jan. 21, 2009;10:37.
Lennon, et al. A scalable, fully automated process for construction of sequence-ready barcoded libraries for 454. Genome Biol. 2010;11(2):R15.
Letsinger, et al. Cationic oligonucletides. J. Am Chem. Soc. 1988; 110:4470-4471.
Letsinger, et al. Effects of pendant groups at phosphorus on binding properties of d-ApA analogues. Nucleic Acids Res. 1986;14(8):3487-99.
Letsinger, et al. Phosphoramidate analogs of oligonucleotides. J Org Chem. 1970;35(11):3800-3.
Levin, et al. Comprehensive comparative analysis of strand-specific RNA sequencing methods. Nat Methods. Sep. 2010;7(9):709-15. doi: 10.1038/nmeth.1491. Epub Aug. 15, 2010.
Lhomme, et al. Abasic DNA Structure reactivity and recognition. Biopolymers. 1999; 52(2): 65-83.
Lindahl, T. An N-Glycosidase from *Escherichia coli* That Releases Free Uracil from DNA Containing Deaminated Cytosine Residues. Proc Natl. Acad. Sci. USA 1974; 71(9):3649-3653.
Lizardi, et al., Mutation detection and single-molecule counting using isothermal rolling-circle amplification. Nature Genetics. 1998 Jul. 1998.19:(3):225-32.
Lockhart, et al. Expression monitoring by hybridization to high-density oligonucleotide arrays. Nature Biotechnology. 1996; 14:1675-1680.
Mag, et al. Synthesis and selective cleavage of an oligodeoxynucleotide containing a bridged internucleotide 5'-phosphorothioate linkage. Nucleic Acids Res. 1991;19(7):1437-41.
Makrigiogos, G. Fluorescent Labeling of Abasic Sites: A Novel Methodology to Detect Closely-Spaced Damage Sites in DNA. Int. J. Radiat. Biol. 1998; 74(1):99-109.

Marchuk, et al. Construction of T-vectors, a rapid and general system for direct cloning of unmodified PCR products. Nucleic Acids Res. Mar. 11, 1991; 19(5): 1154.
Mardis, E. New strategies and emerging technologies for massively parallel sequencing: applications in medical research. Online Apr. 17, 2009. Genome Med. 2009: 1(4); 40. Available at www.ncbinlm.nih.gov/pmc/aricles/PMC2684661/?tool=pubmed. Accessed Oct. 22, 2009.
Mardis. Next-Generation DNA Sequencing Methods. The Annual Review of Genomics and Human Genetics. 2008; 9:387-402.
Margulies, et al. Genome sequencing in microfabricated high-density picolitre reactors [abstract]. Nature. Sep. 15, 2005; 437 (7057): 376-80. Epub Jul. 31, 2005.
Maskos, et al. Oligonucleotide hybridisations on glass supports: a novel linker for oligonucleotide synthesis and hybridization properties of oligonucleotides synthesised in Situ. Nucl. Acids. Res. 20(7):1679-1684.
Maulik, et al. Novel Non-isotopic Detection of MutY Enzyme-recognized Mismatches in DNA Via Ultrasensitive Detection of Aldehydes. Nucl. Acids. Res. 1999: 27(5):1316-1322.
McCarthy, et al. Inducible repair of O-alkylated DNA pyrimidines in *Escherichia coli*. EMBO J. 1984; 3(3):545-50.
McHugh, et al. Novel Regents for Chemical Cleavage at Abasic Sites and UV Photoproducts in DNA. Nucl. Acids. Res. 23(10): 1664-1670.
Meier, et al. Peptide nuclieic acids (PNAs)—Unusual properties of nonionic oligonucleotide analogues. Chem. Int. Ed. Engl. 1992;31:1008-1010.
Meissner, et al. Reduced representation bisulfite sequencing for comparative high-resolution DNA methylation analysis. Nucleic Acids Res. Oct. 13, 2005;33(18):5868-77. Print 2005.
Metzker, M. Sequencing technologies—the next generation. Nat Rev Genet. Jan. 2010;11(1):31-46. Epub Dec. 8, 2009.
Meuzelaar, et al. MegaPlex PCR: a strategy for multiplex amplification. Nat Methods. Oct. 2007;4(10):835-7. Epub Sep. 16, 2007.
Meyer, et al. Parallel tagged sequencing on the 454 platform. Nat Protoc. 2008;3(2):267-78. doi: 10.1038/nprot.2007.520.
Meyer, et al. Targeted high-throughput sequencing of tagged nucleic acid samples. Nucleic Acids Res. 2007;35(15):e97.
Mitchell, et al. Circulating microRNAS as stable blood-based markers for cancer detection. Proc Natl Acad Sci U S A. Jul. 29, 2008;105(30):10513-8. Epub Jul. 28, 2008.
Mitra, et al. Oxidative DNA cleavage by the antitumor antibiotic leinamycin and simple 1,2-dithiolan-3-one 1-oxides: Evidence for thiol-dependent conversion of molecular oxygen to DNA-cleaving oxygen radicals mediated by polysulfides. Journal of the American Chemical Society. 1997; vol. 119(48):11691-11692.
Mitra, et al., In situ localized amplification and contact replication of many individual DNA moecules. Nucleic Acids Research. 1999. 27:(24); e34.
Mizugaki, et al. Preparation of a monoclonal antibody specific for 5-methyl-2'-deoxycytidine and its application for the detection of DNA methylation levels in human peripheral blood cells. Biol Pharm Bull. 1996; 19(12):1537-1540.
Molecular Probe Handbook Section 3.2 obtained from website at: http://www.probes.com/handbook/print/0302.html (Copyright© 1996-2003 by Molecular Probes, Inc.) Visited on Aug. 13, 2003. (18 pages).
Mullis, K.B et al., Eds. (1994). PCR: Polymerase Chain Reaction. Birkhauser: Boston, pp. xv-xvii (Table of Contents).
Nakamura, et al. Highly Sensitive Apurinic/Apyrimidinic site Assay Can Detect Spontaneous and Chemically Induced Depurination Under Physiological Conditions. Cancer Res. 1998; 58:222-225.
Nayak, et al. Functional architecture of T7 RNA polymerase transcription complexes. J. Mol Biol. Aug. 10, 2007; 371(2): 490-500.
Nedderman, et al. Cloning and expression of human G/T mismatch-specific thymine-DNA glycosylase. J Biol Chem. 1996; 271(22):12767-74.
New England BioLabs Inc. NEBNext® Ultra™ Directional RNA Library Prep Kit for Illumina®. Available at https://www.neb.com/products/e7420-nebnext-ultra-directional-rna-library-prep-kit-for-illumina. Accessed Jun. 4, 2014.

(56) References Cited

OTHER PUBLICATIONS

Neylon, et al. Chemical and biochemical strategies for the randomization of protein encoding DNA sequences: library construction methods for directed evolution. Nucleic Acids Res. Feb. 27, 2004;32(4):1448-59. Print 2004.
Ng, et al. Targeted capture and massively parallel sequencing of 12 human exomes. Nature. Sep. 10, 2009. 461, 272-276. http://www.nature.com/nature/journal/v461/n7261/full/nature08250.html. Accessed Oct. 6, 2009.
Nikolaev, et al. Detection of genomic variation by selection of a 9Mb DNA region and high throughput sequencing. PLoS One. Aug. 17, 2009. 4(8): e6659.
Nucleic Acid): An RNA mimic forming exceedingly stable LNA:LNA duplexes. J. Am. Chem. Soc. 1998; 120:13252-3.
Nugen, Inc. Ovation Biotin RNA Amplification and Labeling System User Guite. Catalog #2300-12. Published 2004.
Nugen, Inc. Technical Report #1. The Ovation Biotin System Validation for Use with Affymetrix GeneChip Arrays. Published 2004.
O'Shannessy, et al. Immobilization of Glycoconjugates by Their Oligosaccharides: Use of Hydrazido-Derivatized Matrices. Anal. Biochem. 1990; 191:1-8.
Ochman, et al. Genetic applications of an inverse polymerase chain reaction. Genetics. Nov. 1988;120(3):621-3.
Office action dated Jan. 16, 2013 for U.S. Appl. No. 12/938,112.
Office action dated Feb. 5, 2014 for U.S. Appl. No. 13/750,768.
Office action dated Feb. 8, 2012 for EP Application No. 07810169.8.
Office action dated Feb. 17, 2011 for U.S. Appl. No. 12/305,633.
Office action dated Feb. 28, 2013 for U.S. Appl. No. 13/156,294.
Office action dated Mar. 1, 2010 for U.S. Appl. No. 10/441,663.
Office action dated Mar. 7, 2007 for U.S. Appl. No. 10/441,663.
Office action dated May 16, 2011 for U.S. Appl. No. 11/948,784.
Office action dated May 25, 2006 for U.S. Appl. No. 10/441,663.
Office action dated Jun. 6, 2012 for U.S. Appl. No. 10/441,663.
Office action dated Jun. 19, 2013 for U.S. Appl. No. 12/855,611.
Office action dated Jun. 27, 2013 for U.S. Appl. No. 12/938,112.
Office action dated Jun. 30, 2008 for U.S. Appl. No. 11/026,280.
Office action dated Jul. 5, 2007 for U.S. Appl. No. 10/441,663.
Office action dated Jul. 8, 2011 for U.S. Appl. No. 10/441,663.
Office action dated Jul. 13, 2007 for U.S. Appl. No. 11/026,280.
Office action dated Jul. 15, 2008 for U.S. Appl. No. 10/441,663.
Office action dated Aug. 18, 2010 for U.S. Appl. No. 12/305,633.
Office action dated Sep. 5, 2013 for U.S. Appl. No. 13/156,294.
Office action dated Sep. 9, 2010 for U.S. Appl. No. 10/441,663.
Office action dated Sep. 18, 2006 for U.S. Appl. No. 10/441,663.
Office action dated Sep. 24, 2009 for U.S. Appl. No. 10/441,663.
Office action dated Sep. 25, 2014 for U.S. Appl. No. 13/750,768.
Office action dated Oct. 9, 2013 for U.S. Appl. No. 12/938,112.
Office action dated Oct. 14, 2010 for U.S. Appl. No. 11/948,784.
Office action dated Nov. 7, 2012 for U.S. Appl. No. 13/411,170.
Office action dated Nov. 13, 2012 for U.S. Appl. No. 12/855,611.
Office action dated Dec. 5, 2008 for U.S. Appl. No. 10/441,663.
Office action dated Dec. 17, 2007 for U.S. Appl. No. 10/441,663.
Okou, et al. Microarray-based genomic selection for high-throughput resequencing. Nat Methods. Nov. 2007;4(11):907-9. Epub Oct. 14, 2007.
Olson, M. Enrichment of super-sized resequencing targets from the human genome. Nat Methods. Nov. 2007;4(11):891-2.
Openwetware. Directional-RNAseq Prep. Available at http://openwetware.org/wiki/Directional-RNAseq_Prep. Accessed Jun. 4, 2014.
Pang, et al. Use of modified nucleotides and uracil-DNA glycosylase (UNG) for the control of contamination in the PCR-based amplification of RNA. Molecular and Cellular Probes. 1992; 6:251-256.
Parameswaran, et al. A pyrosequencing-tailored nucleotide barcode design unveils opportunities for large-scale sample multiplexing. Nucleic Acids Res. 2007;35(19):e130.
Parkhomchuk, et al. Transcriptome analysis by strand-specific sequencing of complementary DNA. Nucleic Acids Res. Oct. 2009;37(18):e123.
Pauwels, et al. Biological activity of new 2-5A analogues. Chemica Scripta. 1986;26:141-9.
Pease, et al. A rapid, directional RNA-seq library preparation workflow for Illumina [reg] sequencing. Nature Methods. 2012; 9, No. 3.
Pease, et al. Light-generated oligonucleotide arrays for rapid DNA sequence analysis. Proc. Natl. Acad. Sci. USA 1994; 91:5022-5026.
Pease, et al. Rapid, directional RNA-seq library preparation kits for formalin-fixed paraffin-embedded RNA. Nature Methods. 2012; 9: Published online Sep. 27, 2012.
Pei, et al. Site-specific cleavage of duplex DNA by semisynthetic nuclease via triple-helix formation. Pro. Natl. Acad. Sci. USA. Dec. 1990 87: 9858-9862.
Peng, et al. Kamchatka crab duplex-specific nuclease-mediated transcriptome subtraction method for identifying long cDNAs of differentially expressed genes. Analytical Biochemistry. Jan. 15, 2008. 372:2, 148-155. (abstract).
Pierce, et al. Linear-after-the-exponential polymerase chain reaction and allied technologies. Real-time detection strategies for rapid, reliable diagnosis from single cells. Methods Mol Med. 2007;132:65-85.
Pollack, et al. Genome-wide analysis of DNA copy-number changes using cDNA microarrays. Nature Genet. 1999; 23:41-46.
Porreca, et al. Multiplex amplification of large sets of human exons. Nat Methods. Nov. 2007;4(11):931-6. Epub Oct. 14, 2007.
Prashar, et al. Analysis of differential gene expression by display of 3' end restriction fragments of cDNAs. Proc Natl Acad Sci U S A. Jan. 23, 1996;93(2):659-63.
Proudnikov, et al. Chemical methods of DNA and RNA fluorescent labeling. Nucleic Acids Res. Nov. 15, 1996;24(22):4535-42.
Ramsahoye, et al. Non-CpG methylation is prevalent in embryonic stem cells and may be mediated by DNA methyltransferase 3a. Proc Natl Acad Sci U S A. May 9, 2000;97(10):5237-42.
Ranasinghe, et al. Fluorescence based strategies for genetic analysis. Chem Commun (Camb). Nov. 28, 2005;(44):5487-502. Epub Sep. 30, 2005.
Rawls, R. Optimistic about antisense. Promising clinical results and chemical strategies for further improvements delight antisense drug researchers. C & E News. Jun. 2, 1997; 35-59.
Riley, et al. A novel, rapid method for the isolation of terminal sequences from yeast artificial chromosome (YAC) clones. Nucleic Acids Res. May 25, 1990;18(10):2887-90.
Roberts, R. Restriction enzymes at NEB: over 30 years of innovation, the discovery, cloning and engineering of these essential reagents. NEB Expression. Winter. 2008. vol. 2.4. Available at www.neb.com/nebecomm/tech_reference/restriction _enzymes/feature_article_innovation.asp. Accessed Aug. 16, 2010.
Robertson. DNA methylation and human disease. Nat Rev Genet. Aug. 2005;6(8):597-610.
Roche Company. 454 life sciences, applications—sequence capture targeted region. http://www.454.com/applications/sequence-capture-targeted-region.asp. Accessed Oct. 6, 2009.
Saiki, et al. Analysis of enzymatically amplified beta-globin and HLA-DQ alpha DNA with allele-specific oligonucleotide probes. Nature. Nov. 13-19, 1986;324(6093):163-6.
Sambrook, J. et al., Eds. (1989). Molecular Cloning: A Laboratory Manual. 2nd Edition, Cold Spring Harbor Laboratory Press, pp. xi-xxxviii (Table of Contents).
Sanders, et al. Targeting individual subunits of the FokI restriction endonuclease to specific DNA strands, Nucleic Acids Research. Apr. 2009. Nucleic Acids Res. 37:(7):2105-15.
Sanghvi, et al. ed. Chapters 2 and 3, ASC Symposium Series 580—Carbohydrates Modifications in Antisense Research. American Chemical Society. Washington, DC. 1994.
Sanghvi, et al. ed. Chapters 6 and 7, ASC Symposium Series 580—Carbohydrates Modifications in Antisense Research. American Chemical Society. Washington, DC. 1994.
Sano, et al. Detection of heavy methylation in human repetitive DNA subsets by a monoclonal antibody against 5-methylcytosine. Biochim Biophys Acta. 1988; 951(1):157-65.

(56) References Cited

OTHER PUBLICATIONS

Sartori, et al. A novel uracil-DNA glycosylase with broad substrate specificity and an unusual active site. EMBO J. 2002; 21(12):3182-91.
Sawai, et al. Synthesis and properties of oligoadenylic acids containing 2'-5' phosphoramide linkage. Chem. Lett. 1984; 805-808.
Schena, et al. Parallel human genome analysis: microarray-based espression monitoring of 1000 genes. Proc Natl. Acad. Sci. USA Biochemistry. 1996; 93:10614-10619.
Schena, et al. Quantitative monitoring of gene expression patterns with a complementary DNA microarray. Science. 1995; 270:467-470.
Schmid, et al. Chic and chec: genomic mapping of chromatin proteins. Molecular Cell. 2004. 16, No. 1, pp. 147-157. (abstract).
Shalon, et al. Parallel human genome analysis: microarray system for analyzing complex DNA samples using two-color fluorescent probe hybridization. Genome Res. 1996; 6:639-645.
Shida, et al. Cleavage of Single-and double-Stranded DNAs Containing an Abasic Residue by *Escherichia coli* Exonuclease III (AP Endonuclease VI) Nucl. Acids. Res. 1996; 24(22):4572-4576.
Slupphaug, et al. Low incorporation of dUMP by some thermostable DNA polymerases may limit their use in PCR amplifications. Anal. Biochem. 1993; 211:164-169.
Sohail, et al. Human activation-induced cytidine deaminase causes transcription-dependent, strand-biased C to U deaminations. Nucleic Acids Res. 2003; 31(12):2990-4.
Soni, et al. Progress toward ultrafast DNA sequencing using solid-state nanopores. Clin Chem. Nov. 2007;53(11):1996-2001. Epub Sep. 21, 2007.
Sprinzl, et al. Enzymatic incorporation of ATP and CTP analogues into the 3' end of tRNA. Eur J Biochem. Dec. 1977;81(3):579-89.
Srivastava, et al. Mammalian Abasic Site Base Excision Repair. Identification of the Reaction Sequence and Rate-Determining Steps. J. Biol. Chem. 1998;273(33):21203-21209.
Stemmer, et al. Single-step assembly of a gene and entire plasmid from large numbers of oligodeoxyribonucleotides. Gene. Oct. 16, 1995;164(1):49-53.
Stephpens, et al. Automating sequence-based detection and genotyping of SNPs from diploid samples. Nat Genet. Mar. 2006;38(3):375-81. Epub Feb. 19, 2006.
Steullet, et al. Clevage of Abasic Sites in DNA by Intercalator-amines. Bioorganic and Medicinal Chem. 1999; 7:2531-2540.
Stratagene catalog, Gene Characterizatin Kits. 1988 p. 39.
Sugiyama, et al. Chemistry of thermal degradation of abasic sites in DNA. Mechanistic investigation on thermal DNA stand clevage of alkylated DNA. Chem. Res. Toxicol. 1994; 1:673-683.
Summerer, D. Enabling technologies of genomic-scale sequence enrichment for targeted high-throughput sequencing. Genomics. Dec. 2009;94(6):363-8. (abstract).
Summerer, et al. Microarray-based muticycle-enrichment of genomic subsets for targeted next-generation sequencing. Accepted Jun. 18, 2009. Available at www.ncbi.nlm.nih.gov/pubmed/19638418. Accessed Oct. 6, 2009.
Timblin, et al. Application for PCR technology to subtractive cDNA cloning: identification of genes expressed specifically in murine plasmacytoma cells. Nucleic Acids Res. Mar. 25, 1990;18(6):1587-93.
Tong, et al. Detection of restriction enzyme-digested target DNA by PCR amplification using a stem-loop primer: application to the detection of hypomethylated fetal DNA in maternal plasma. Clin Chem. Nov. 2007;53(11):1906-14. Epub Sep. 27, 2007.
Turner, et al. Methods for genomic partitioning. Annu Rev Genomics Hum Genet. 2009;10:263-84. doi: 10.1146/annurev-genom-082908-150112.
Vairapandi, et al. Partial purification and characterization of human 5-methylcytosine-DNA glycosylase. Oncogene. 1996; 13(5):933-8.
Vairapandi, et al. Human DNA-demethylating activity: a glycosylase associated with RNA and PCNA. J Cell Biochem. 2000; 79(2):249-60.
Varkonyi-Gasic, et al. Protocol: a highly sensitive RT-PCR method for detection and quantification of microRNAs. Plant Methods. Oct. 12, 2007;3:12.
Varley, et al. Nested Patch PCR enables highly multiplexed mutation discovery in candidate genes. Genome Res. Nov. 2008;18(11):1844-50. doi: 10.1101/gr.078204.108. Epub Oct. 10, 2008.
Vincent, et al. Helicase-dependent isothermal DNA amplification. EMBO Rep. Aug. 2004;5(8):795-800. Epub Jul. 9, 2004.
Vos, et al. AFLP: a new technique for DNA fingerprinting. Nucleic Acids Res. Nov. 11, 1995;23(21):4407-14.
Walker, et al., Strand displacement amplification-an isothermal, in vitro DNA amplifcation technique. Nucleic Acids Resarch. 1991. 20(7): 1691-1696.
Westburg. Fast, Directional RNA-Seq Library Prep. Abailable at http://www.westburg.eu/lp/ma-seq-library-preparation. Accessed on Jun. 4, 2014.
Westin, et al., Anchored multiplex amplification on a microelectronic chip array. Nature Biotechnology. Feb. 18, 2000(2):199-204.
Wikipedia. ABI solid sequencing. Http://en.wikipedia.org/wiki/ABI_Solid_Sequencing. Last modified Oct. 4, 2009 Accessed Oct. 22, 2009.
Wikipedia. DNA sequencing. Alailable at http://en.wikipedia.org/wiki/Next-generation_sequencing. Last modified Oct. 8, 2009. Accessed Oct. 22, 2009.
Wilchek, et al. Labeling Glycoconjugates with Hydrazide Reagents. Methods Enzymol. 1987; 138:429-442.
Wolffe, et al. DNA demethylation. Proc Natl Acad Sci USA. 1999; 96(11):5894-6.
Young, et al. A new strategy for genome assembly using short sequence reads and reduced representation libraries. Genome Res. Feb. 2010;20(2):249-56. doi: 10.1101/gr.097956.109.
Zalipsky, S. Functionalized Poly(ethylene glycol) for Preparation of Biologically Relevant Congugates. Bioconjugate Chem. 1995; 6:150-165.
Zang, et al. DNA alkylation by leinamycin can be triggered by cyanide and phosphines. Bioorg Med Chem Lett. Jun. 18, 2001;11(12):1511-5.
Zhang, et al. Multiplex sequencing on the SOLID platform with 10, 16, or 96 barcodes. 2009 Life technologies. www3.appliedbiosystems.com/cms/groups/mcb_marketing/documents/generaldocuments/cms_065528.pdf.
Zhu, et al. Overexpression of 5-methylcytosine DNA glycosylase in human embryonic kidney cells EcR293 demethylates the promoter of a hormone-regulated reporter gene. Proc Natl Acad Sci USA. 2001; 98(9):5031-6.
Zhu, et al. 5-Methylcytosine DNA glycosylase activity is also present in the human MBD4 (G/T mismatch glycosylase) and in a related avian sequence. Nucleic Acids Res. 2000; 28(21):4157-65.
Zhulidov, et al. Simple cDNA normalization using kamchatka crab duplex=specific nuclease. Nucleic Acids Research.Online Feb. 18, 2004. 32:3 e37.
Ziller, et al. Genomic distribution and inter-sample variation of non-CpG methylation across human cell types. PLoS Genet. Dec. 2011;7(12):e1002389. doi: 10.1371/journal.pgen.1002389. Epub Dec. 8, 2011.
Notice of Allowance dated Apr. 17, 2017 for U.S. Appl. No. 14/634,326.
Office Action dated Mar. 3, 2017 for U.S. Appl. No. 15/154,414.
U.S. Appl. No. 14/990,339, filed Jan. 7, 2016, Amorese et al.
U.S. Appl. No. 14/991,340, filed Jan. 8, 2016, Schroeder et al.
U.S. Appl. No. 14/995,882, filed Jan. 14, 2016, Armour.
U.S. Appl. No. 14/778,564, filed Sep. 15, 2015, Amorese et al.
U.S. Appl. No. 14/836,936, filed Aug. 15, 2015, Amorese et al.
U.S. Appl. No. 14/877,075, filed Oct. 7, 2015, Kurn.
U.S. Appl. No. 14/920,254, filed Oct. 22, 2015, Armour.
Beaucage et al. Deoxynucleoside Phosphoramidites—A New Class of Key Intermediates for Deoxypolynucleotide Synthesis. Tetrahedron Letters. 1981;22(20):1859-1862.
Brown, et al. Chemical synthesis and cloning of a tyrosine tRNA gene. Methods Enzymol. 1979;68:109-51.

(56) References Cited

OTHER PUBLICATIONS

Gundmundsson, et al. Genome-wide association and replication studies identify four variants associated with prostate cancer susceptibility. Nat Genet. Oct. 2009;41(10):1122-6. doi: 10.1038/ng. 448. Epub Sep. 20, 2009.
Narang, et al. Improved phosphotriester method for the synthesis of gene fragments. Methods Enzymol. 1979;68:90-8.
Out, et al. Deep sequencing to reveal new variants in pooled DNA samples. Hum Mutat. Dec. 2009;30(12):1703-12. doi: 10.1002/humu.21122.
Turner, et al. Massively parallel exon capture and library-free resequencing across 16 genomes. Nat Methods. May 2009;6(5):315-6. doi: 10.1038/nmeth.f.248. Epub Apr. 6, 2009.
Voelkerding, et al. Next-generation sequencing: from basic research to diagnostics. Clin Chem. Apr. 2009;55(4):641-58. doi: 10.1373/clinchem.2008.112789. Epub Feb. 26, 2009.
Froussard. A random-PCR method (rPCR) to construct whole cDNA library from low amounts of RNA. Nucleic Acids Res. Jun. 11, 1992;20(11):2900.
Office action dated Oct. 30, 2015 for U.S. Appl. No. 13/750,768.
Office action dated Nov. 4, 2015 for U.S. Appl. No. 14/030,761.
Tucker, et al. Massively parallel sequencing: the next big thing in genetic medicine. Am J Hum Genet. Aug. 2009;85(2):142-54. doi: 10.1016/j.ajhg.2009.06.022.
Vater, et al. Short bioactive Spiegelmers to migraine-associated calcitonin gene-related peptide rapidly identified by a novel approach: tailored-SELEX. Nucleic Acids Res. Nov. 1, 2003;31(21):e130.
Zhong, et al. High-throughput illumina strand-specific RNA sequencing library preparation. Cold Spring Harb. Protoc.; 2011; 940-949. doi:10.1101/pdb.prot5652.
Callow, et al. Selective DNA amplification from complex genomes using universal double-sided adapters. Nucleic Acids Res. Jan. 28, 2004;32(2):e21.
European search report and opinion dated Jul. 23, 2015 for EP Application No. 13740653.
Tewhey, et al. Microdroplet-based PCR enrichment for large-scale targeted sequencing. Nat Biotechnol. Nov. 2009;27(11):1025-31. doi: 10.1038/nbt.1583. Epub Nov. 1, 2009.
Levesque-Sergerie, et al. Detection limits of several commercial reverse transcriptase enzymes: impact on the low- and high-abundance transcript levels assessed by quantitative RT-PCR. BMC Mol Biol. Oct. 22, 2007;8:93.
Office action dated Apr. 4, 2016 for U.S. Appl. No. 14/995,882.
Bower, et al. Targeted rapid amplification of cDNA ends (T-RACE)—an improved RACE reaction through degradation of non-target sequences. Nucleic Acids Res. Nov. 2010;38(21):e194. doi: 10.1093/nar/gkq816. Epub Sep. 15, 2010.
Chen, et al. BisQC: an operational pipeline for multiplexed bisulfite sequencing. BMC Genomics. Apr. 16, 2014;15:290. doi: 10.1186/1471-2164-15-290.
Chenchik, et al. Full-length cDNA cloning and determination of mRNA 5' and 3' ends by amplification of adaptor-ligated cDNA. Biotechniques. Sep. 1996;21(3):526-34.
European search report and opinion dated May 22, 2015 for EP Application No. 12842163.3.
International search report and written opinion dated Jun. 18, 2015 for PCT/US2015/018112.
Singapore exam report dated Apr. 7, 2015 for SG Application No. 11201404243W.
Bodi, et al. Comparison of Commercially Available Target Enrichment Methods for Next-Generation Sequencing. J Biomol Tech. Jul. 2013; 24(2): 73-86.
European search report and opinion dated Jan. 29, 2016 for EP Application No. 13806978.
International search report and written opinion dated Feb. 5, 2016 for PCT/US2015/047053.
Ovation® Target Enrichment System. User guide. Nugen. 2016. 45 pages.
Watson, et al. Cloning and assembly of PCR products using modified primers and DNA repair enzymes. Biotechniques. Nov. 1997;23(5):858-62, 864.
Office action dated Apr. 3, 2015 for CN Application No. 2012800608251.
Ganova-Raeva, et al. Primer Extension Enrichment Reaction (PEER): a new subtraction method for identification of genetic differences between biological specimens. Nucleic Acids Research. 2006; 34(11):e76.
Notice of allowance dated Jul. 28, 2015 for U.S. Appl. No. 13/643,056.
Office action dated Jul. 9, 2015 for U.S. Appl. No. 14/211,261.
Office action dated Jul. 15, 2015 for U.S. Appl. No. 13/750,768.
Office action dated Jul. 15, 2015 for U.S. Appl. No. 13/938,059.
Shendure, et al. Accurate multiplex polony sequencing of an evolved bacterial genome. Science. Sep. 9, 2005;309(5741):1728-32. Epub Aug. 4, 2005.
Shendure, et al. Accurate multiplex polony sequencing of an evolved bacterial genome. Science. Sep. 9, 2005;309(5741):1728-32. Epub Aug. 4, 2005. Supplemental Materials. 41 pages.
Jang, et al., Spectra of BRCA1 and BRCA2 mutations in Korean patients with breast cancer: the importance of whole-gene sequencing. Journal of Human Genetics. vol. 57. pp. 212-215. Jan. 5, 2012.
Notice of Allowance dated Jun. 21, 2017 for U.S. Appl. No. 14/634,326.
Notice of Allowance dated Jul. 25, 2017 for U.S. Appl. No. 14/778,564.
Office Action dated Aug. 7, 2017 for U.S. Appl. No. 14/920,254.
Office Action dated Aug. 18, 2017 for U.S. Appl. No. 15/471,785.
Office Action dated Aug. 22, 2017 for U.S. Appl. No. 14/836,936.
Office Action dated Aug. 30, 2017 for U.S. Appl. No. 14/990,339.
Office Action dated Dec. 15, 2017 for U.S. Appl. No. 14/991,340, 14 pages.

* cited by examiner

Figure 1. rRNA depletion from a nucleic acid library using insert-dependent adaptor cleavage (InDA-C).
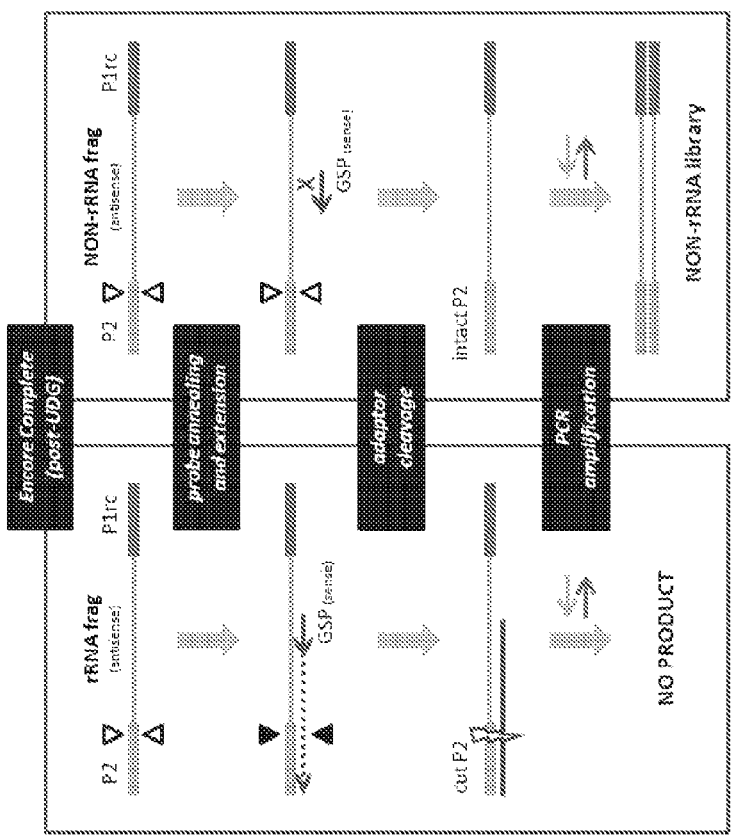

Figure 2. Summary of results - Example 1.

| library | probe | BspQ1 | total number of reads | % of reads mapping to reference | % of mapped reads in ORFs | % of mapped reads in rRNA | % of rRNA reads mapping to sense strand | % of rRNA reads mapping to antisense strand |
|---|---|---|---|---|---|---|---|---|
| ctrl | - | - | 27,161,879 | 99.3 | 1.0 | 99.0 | 99.7 | 0.3 |
| test1 | - | - | 7,510,963 | 97.3 | 5.6 | 92.9 | 99.1 | 0.9 |
| test2 | + | - | 8,679,815 | 97.5 | 5.6 | 92.9 | 99.1 | 0.9 |
| test3 | - | + | 9,331,682 | 97.4 | 5.2 | 93.4 | 99.2 | 0.8 |
| test4 | + | + | 9,355,578 | 95.1 | 11.7 | 86.1 | 98.1 | 1.9 |

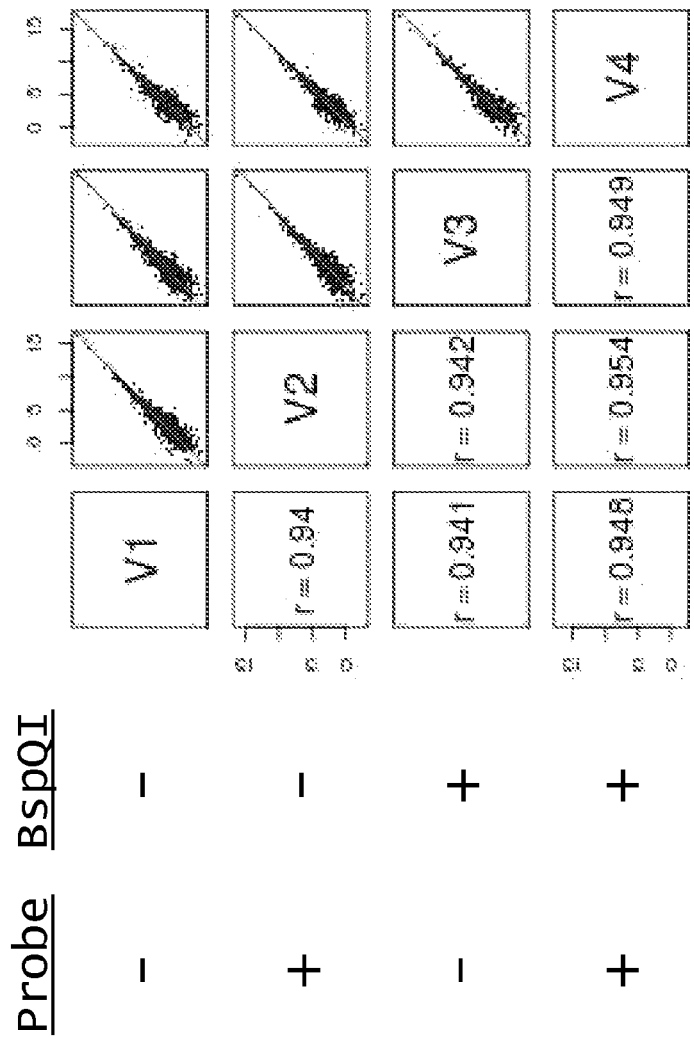
Figure 3. Comparison of expression profiles from the test libraries 1-4 in Example 1. InDA-C does not perturb transcript abundance.

Figure 5: Directional Library Construction

Figure 6: InDA-C with Single cell, cDNA double hydrolysis

Figure 7: InDA-C with Single cell, 3 base code in second strand primer

SEQUENCE LISTING

```
<160> NUMBER OF SEQ ID NOS: 5

<210> SEQ ID NO 1
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1
tacactcutt cccuacacga cgaucttccg auct                               34

<210> SEQ ID NO 2
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
aatgatacgg cgaccaccga agataagaag aatgacgtca agtgcgatcg caggatagat    60

<210> SEQ ID NO 3
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
caagcagaag acggcatacg agatgtgact ggagttcaga cgtgtgctct tccgatct      58

<210> SEQ ID NO 4
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 4
aatgatacgg cgaccaccga                                                    20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
caagcagaag acggcatacg                                                    20
```

COMPOSITIONS AND METHODS FOR NEGATIVE SELECTION OF NON-DESIRED NUCLEIC ACID SEQUENCES

CROSS REFERENCE

This application is a National Stage of International Application No. PCT/US2013/032606, filed Mar. 15, 2013, which claims the priority benefit of provisional patent application U.S. Ser. No. 61/661,293, filed Jun. 18, 2012, all of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Apr. 2, 2015, is named 25115-759.831_SL.txt and is 1,668 bytes in size.

BACKGROUND OF THE INVENTION

Next generation sequencing (NGS) libraries are collections of DNA fragments whose nucleotide sequences will be determined. The sources of DNA for insertion into these libraries are typically genomic DNA that has been fragmented to a desired length, or copies of the transcriptome from a given cell population. Transcriptome libraries are generated by making a cDNA copy of an RNA population, creating a complement to each DNA strand, thereby generating double-stranded DNA, and then ligating the double-stranded DNAs to library-specific adaptors. The cDNA can be synthesized by using random primers, sequence-specific primers or primers containing oligo dT tails to prime a population of transcripts that are polyadenylated. Frequently, these fragment populations contain DNA that is not of interest to a particular study, and in some cases, these non-desired DNA sequences represent a very significant percentage of the overall DNA population. For example, in whole transcriptome studies, ribosomal RNA (rRNA) sequences comprise the majority (60-90%) of all fragments in a typical cDNA library, absent steps to remove rRNA from the samples. In another example, gene expression profiling from peripheral blood is primarily concerned with mRNA from peripheral blood mononuclear cells (PBMCs), which make up less than 0.1% of the whole blood sample. Reduction of globin RNA from red blood cells, which make up majority of the cells in the blood sample, is desirable in such assays.

In the case of rRNA removal or depletion, three general methods have been described: 1) removal of rRNA from the starting population; 2) differential priming using oligo dT primers (i.e. priming polyadenylated transcripts only); and 3) differential priming where primers complementary to rRNA sequences are specifically eliminated (or under-represented) in a primer pool (Not-So-Random or NSR primer approach; see Armour et al., 2009). Priming a total RNA population with primers that only recognize poly(A)-sequences is problematic for two reasons. First, it cannot be used with prokaryotic organisms because prokaryotic mRNAs do not contain poly(A)-sequences at their 3' ends. Second, even with eukaryotic RNA samples, many biologically important elements, such as regulatory transcripts, are not polyadenylated and are therefore lost from the library with oligo dT priming. While NSR priming strategies can be effective when designed to specific organisms, NSR priming can cause distortions in the sample populations when a less optimized set of primers is employed across a broader range of sample types.

There is a need for improved methods for removal of specific non-desired DNA fragments from NGS libraries. Such methods would ideally enable starting with an unbiased template population and eliminating non-desired DNA fragments in a sequence-specific manner after the NGS library has been generated. The invention described herein fulfills this need.

SUMMARY OF THE INVENTION

The present invention provides novel methods, compositions and kits for construction of NGS libraries in which non-desired nucleic acid sequences have been depleted or substantially reduced. Specifically, an important aspect of this invention is the methods and compositions that allow for elimination or reduction of non-desired DNA sequences in a sequence-specific manner after the generation of a NGS library in which all sequences of the starting nucleic acid sequence population (for example, a transcriptome) are represented in an undistorted, unbiased manner. The methods of the invention can be employed for the elimination of non-desired nucleic acid sequences, such as ribosomal RNA, from a nucleic acid library, and consequently, for the enrichment of nucleic acid sequences of interest in the library.

In one aspect, the invention provides a method for the selective removal of non-desired nucleic acid sequences in a sequence-specific manner from a nucleic acid library with single-stranded DNA templates. In some embodiments, the method comprises: a) annealing a sequence-specific oligonucleotide primer or a set of sequence-specific oligonucleotide primers to the single-stranded DNA templates with adaptors of fixed orientation attached at each end, wherein the sequence-specific oligonucleotides are designed to be complementary to the non-desired nucleic acid sequences or regions adjacent to the non-desired nucleic acid sequences, and wherein one of the two adaptor sequences contains a recognition sequence for a restriction endonuclease specific for double-stranded DNA; b) extending the sequence-specific primers with a DNA polymerase beyond the adaptor-DNA template junction, thereby creating double-stranded DNA fragments where the oligonucleotide primers are complementary to the single-stranded DNA templates; c) treating the population of DNA fragments (both single-stranded and double-stranded) with a restriction endonuclease specific for double-stranded DNA, thereby cleaving only double-stranded DNA fragments at the adaptor restriction endonuclease site and thus removing adaptor from one end of the fragments containing the non-desired nucleic acid sequences; and d) performing PCR using primers specific to each adaptor whereby exponential amplification only occurs when fragments have both PCR priming sites on the same template, thereby amplifying the desired nucleic acid sequences only.

In another aspect, the invention provides a method for the construction of a nucleic acid library from a sample of interest while retaining an unbiased nucleic acid template population in which all sequences of the starting nucleic acid sequence population are represented.

In some embodiments, the invention provides a method for the construction of a directional (i.e. strand-specific) nucleic acid library, the method comprising: a) reverse transcribing an RNA sample; b) generating double-stranded cDNA from a reverse transcribed RNA sample, wherein during the second strand cDNA synthesis at least one modified nucleotide is incorporated into the second strand of cDNA along the length of the strand; c) performing end repair on the double-stranded cDNA; d) ligating adaptors to the double-stranded cDNA, wherein one of the two adaptors has the modified nucleotide incorporated into the ligation strand of the adaptor; e) performing gap repair; f) selectively removing the second strand of cDNA by a suitable degrading agent; and g) removing the degradation products from the sample, thereby resulting in a library of single-stranded DNA templates with adaptors of fixed orientation attached to each end.

In a preferred embodiment, the modified nucleotide incorporated into the second strand of cDNA is deoxyuridine triphosphate (dUTP), and the degrading agent is the nuclease Uracil-N-Glycosylase (UNG).

In other embodiments, the nucleic acid library being constructed is not strand-specific.

In some embodiments, the nucleic acid sample of interest comprises total RNA. In some embodiments, the nucleic acid sample of interest is primed using a random primer population. In other embodiments, the nucleic acid sample of interest is primed using a partially selective primer population.

In various aspects the invention relates to methods for depleting undesired nucleic acids from a pool of nucleic acids. Libraries may be prepared with the remaining nucleic acids. Nucleic acid depletion and library generation may be performed in a strand specific manner. According to a first aspect, the invention relates to a method for depleting or reducing specific non-desired nucleic acid sequences from a nucleic acid library, the method comprising: (a) generating a nucleic acid library comprising single-stranded DNA fragments with adaptors of fixed orientation attached to each end of each DNA fragment; (b) annealing sequence-specific oligonucleotide probes to the single-stranded DNA fragments with adaptors of fixed orientation attached at each end, wherein the sequence-specific oligonucleotide probes are designed to be complementary to the non-desired nucleic acid sequences, and wherein at least one of the two adaptors comprises a recognition sequence for a restriction endonuclease specific for double-stranded DNA; (c) extending the sequence-specific oligonucleotide probes with a DNA polymerase, thereby creating double-stranded DNA fragments comprising at least a portion of the non-desired nucleic acid sequences; (d) treating the population of DNA fragments comprising double-stranded and single-stranded DNA with a restriction endonuclease specific for double-stranded DNA, thereby cleaving double-stranded DNA fragments at the restriction endonuclease site; and (e) performing PCR with a set of primers specific to the adaptor sequences, thereby amplifying the DNA fragments comprising the desired nucleic acid sequences. In some embodiments, the method further comprises an additional step of sequencing the amplified products. In some embodiments, the nucleic acid library originates from a population of sorted cells. In some embodiments, the nucleic acid library originates from a single cell. In some embodiments, the method further comprises sorting cells into a multiwell plate, microarray, microfluidic device, or slide and thereby generating the population of sorted cells. In some embodiments, the sorting is performed according to a cell surface marker. In some embodiments, the sorting is performed according to optical properties of the cells. In some embodiments, the sorting is performed according to cell size. In some embodiments, the non-desired nucleic acid sequences comprise bacterial ribosomal RNA, mitochondrial DNA, human globin mRNA, human cytoplasmic rRNA, human mitochondrial rRNA, grape cytoplasmic rRNA, grape mitochondrial rRNA, or grape chloroplast rRNA. In some embodiments, the restriction endonuclease of step d. is BspQI. In some embodiments, the DNA polymerase comprises a hot start polymerase. In some embodiments, the DNA polymerase is MyTaq polymerase. In some embodiments, step (a) comprises i. reverse transcribing a RNA sample; ii. generating double-stranded cDNA from the reverse transcribed RNA sample, wherein at least one of the four dNTPs dATP, dCTP, dGTP or dTTP is replaced by a non-canonical dNTP during second strand synthesis and incorporated into the second strand; iii. performing end repair on the double-stranded cDNA; iv. ligating adaptors to a 5' end of the double-stranded cDNA, wherein one of the adaptor strands has the non-canonical nucleotide incorporated into a ligation strand of the adaptor; v. performing gap repair; and iv. selectively removing the second strand by a cleavage agent. In some embodiments, the non-canonical nucleotide comprises uridine or inosine. In some embodiments, step vi comprises cleaving a base portion of the one or more non-canonical nucleotides, thereby forming an abasic site. In some embodiments, the cleavage agent comprises a glycosylase. In some embodiments, the glycosylase is UNG or UDG. In some embodiments, the cleavage agent comprises a primary amine. In some embodiments, the cleavage agent comprises a polyamine. In some embodiments, the polyamine is DMED. In some embodiments, the cleavage agent comprises a glycosylase and a polyamine. In some embodiments, the cleavage agent comprises endonuclease V.

In a second aspect, the invention relates to a method of adapter ligation to a pool of nucleic acids, comprising: (a) ligating a nucleic acid comprising a first nucleic acid strand comprising a 5' phosphate, a second nucleic acid strand comprising a 5' phosphate and one or more non-canonical nucleotides, with at least a first adapter comprising a first adapter strand lacking a 5' phosphate and a second adapter strand lacking a 5' phosphate and one or more non-canonical nucleotides; (b) performing a 3' extension reaction; and (c) performing a cleavage reaction with an agent comprising one or more cleavage reagents, thereby cleaving at least one nucleic acid strand comprising one or more non-canonical nucleotides; wherein one of the one or more cleavage agents is specific for nucleic acid strands comprising the one or more non-canonical nucleotides. In some embodiments, the method comprises ligating the nucleic acid with a second adapter comprising a third adapter strand lacking a 5' phosphate and a fourth adapter strand lacking a 5' phosphate and one or more non-canonical nucleotides, wherein the first and the second adapters are different. In some embodiments, the nucleic acid is ligated with a first or second adapter at each end. In some embodiments, the non-canonical nucleotide is selected from uracil and inosine. In some embodiments, step c comprises cleaving a base portion of the one or more non-canonical nucleotides, thereby forming an abasic site. In some embodiments, the one or more cleavage reagents comprises a glycosylase. In some embodiments, the glycosylase is UNG or UDG. In some embodiments, the one or more cleavage reagents comprises a primary amine. In some embodiments, the one or more cleavage reagents comprises a polyamine. In some embodiments, the polyamine is DMED. In some embodiments, the one or more cleavage reagents comprises a glycosylase and a polyamine. In some embodiments, the one or more cleavage reagents comprises endonuclease V. In some embodiments, the method further comprises performing an amplification reaction comprising a first primer and second primer, wherein the first primer is hybridizable to the first adapter strand and the second primer is hybridizable to the fourth adapter strand, thereby generating amplified products. In some embodiments, the first adapter comprises a recognition sequence for a restriction endonuclease specific for double-stranded DNA. In some embodiments, the method further comprises (d) hybridizing a probe to a sequence on the first nucleic acid strand, (e) extending the probe with a DNA polymerase, thereby producing a partial duplex nucleic acid, and (f) treating the partial duplex nucleic acid with a restriction endonuclease specific for double-stranded DNA, thereby cleaving double-stranded DNA fragments at the recognition sequence. In some embodiments, the method further comprises performing PCR with a set of primers specific to the adaptor sequences, thereby amplifying at least a second nucleic acid in the pool of nucleic acids. In some embodiments, the second nucleic acid lacks the sequence in step d. In some embodiments, the method further comprises sequencing a portion of the second nucleic acid. In some embodiments, the nucleic acid is generated by i. performing a first strand synthesis on an RNA, thereby forming a first strand synthesis product; and ii. performing a second strand synthesis on the first strand in the presence of a non-canonical nucleotide, thereby forming a second strand synthesis product. In some embodiments, the method further comprises selectively cleaving the RNA. In some embodiments, selectively cleaving the RNA comprises treatment with RNAse H. In some embodiments, the method further comprises iii. fragmenting the first and second strand synthesis products, thereby generating fragmented first and second strand synthesis products; iv. performing end repair; and v. performing 5' phosphorylation. In some embodiments, the pool of nucleic acids originates from a population of sorted cells. In some embodiments, the pool of nucleic acids originates from a single cell. In some embodiments, the method further comprises sorting cells into a multiwell plate, microarray, microfluidic device, or slide and thereby generating the population of sorted cells. In some embodiments, the sorting is performed according to a cell surface marker. In some embodiments, the sorting is performed according to optical properties of the cells. In some embodiments, the sorting is performed according to cell size. In some embodiments, the pool of nucleic acids comprises bacterial ribosomal RNA, mitochondrial DNA, human globin mRNA, human cytoplasmic rRNA, human mitochondrial rRNA, grape cytoplasmic rRNA, grape mitochondrial rRNA, or grape chloroplast rRNA. In some embodiments, the restriction endonuclease is BspQI. In some embodiments, the 3' extension reaction is performed using a hot start polymerase. In some embodiments, the 3' extension reaction is performed using MyTaq polymerase.

In a third aspect, the invention relates to a method of adapter ligation to create a strand retained library of nucleic acids comprising desired and undesired nucleic acids, comprising: (a) mixing pool of templates comprising an undesired nucleic acid comprising one or more non-canonical nucleotides and a desired nucleic acid comprising one or more non-canonical nucleotides with a plurality of partial duplex primers each comprising a 3' overhang, (b) annealing to the templates the plurality of partial duplex primers; (c) performing primer extension reaction along the templates, thereby forming double-stranded nucleic acids each comprising a primer extension product, (d) ligating an adapter to at least one 5' end of the primer extension products; and (e) cleaving the templates from the double-stranded nucleic acids with a cleavage agent that is specific for nucleic acids comprising the one or more nucleotides. In some embodiments, the plurality of partial duplex primers comprise at least two partial duplex primers with dissimilar 3' overhang sequences. In some embodiments, the plurality of partial duplex primers comprise a shared sequence within a double-stranded portion. In some embodiments, the method further comprises a step comprising performing a primer extension reaction along the adapter. In some embodiments, step e comprises cleaving a base portion of the one or more non-canonical nucleotides, thereby forming an abasic site. In some embodiments, the cleavage agent comprises a glycosylase. In some embodiments, the glycosylase is UNG or UDG. In some embodiments, the cleavage agent comprises a primary amine. In some embodiments, the cleavage agent comprises a polyamine. In some embodiments, the polyamine is DMED. In some embodiments, the cleavage agents comprises a glycosylase and a polyamine. In some embodiments, the cleavage agent comprises endonuclease V. In some embodiments, the one or more non-canonical nucleotides comprise uracil or inosine. In some embodiments, the one or more non-canonical nucleotides comprise uracil and inosine. In some embodiments, the pool of templates is generated by i. performing a first strand synthesis on an RNA in the presence of the one or more non-canonical nucleotides, thereby forming a first strand synthesis product and ii. performing a fragmentation reaction. In some embodiments, the method further comprises selectively cleaving the RNA. In some embodiments, selectively cleaving the RNA comprises treatment with RNAse H. In some embodiments, the fragmentation reaction comprises utilizing a cleavage agent targeting the one or more non-canonical nucleotides. In some embodiments, fragmentation reaction comprises cleaving a base portion of the one or more non-canonical nucleotides, thereby forming an abasic site. In some embodiments, the cleavage agent comprises a glycosylase. In some embodiments, the glycosylase is UNG or UDG. In some embodiments, the cleavage agent comprises a primary amine. In some embodiments, the cleavage agent comprises a polyamine. In some embodiments, the polyamine is DMED. In some embodiments, the cleavage agents comprises a glycosylase and a polyamine. In some embodiments, the cleavage agent comprises endonuclease V. In some embodiments, the adapter comprises a recognition sequence for a restriction endonuclease specific for double-stranded DNA. In some embodiments, the method further comprises (f), hybridizing a probe to a sequence of the primer extension product; (g) extending the probe with a DNA polymerase, thereby producing a partial duplex nucleic acid, and (h) treating the partial duplex nucleic acid with a restriction endonuclease specific for double-stranded DNA, thereby cleaving double-stranded DNA fragments at the recognition sequence. In some embodiments, the method further comprises performing PCR with a primer that is hybridizable a sequence reverse complimentary to the adapter, thereby amplifying a desired nucleic acid in the pool of templates. In some embodiments, the method further comprises sequencing a portion of the desired nucleic acid. In some embodiments, the pool of templates originates from a population of sorted cells. In some embodiments, the pool of templates originates from a single cell. In some embodiments, the method further comprises sorting cells into a multiwell plate, microarray, microfluidic device, or slide and thereby generating the population of sorted cells. In some embodiments, the sorting is performed according to a cell surface marker. In some embodiments, the sorting is performed according to optical properties of the cells. In some embodiments, the sorting is performed according to cell size. In some embodiments, the pool of templates comprises bacterial ribosomal RNA, mitochondrial DNA, human globin mRNA, human cytoplasmic rRNA, human mitochondrial rRNA, grape cytoplasmic rRNA, grape mitochondrial rRNA, or grape chloroplast rRNA. In some embodiments, the restriction endonuclease is BspQI. In some embodiments, the primer extension reaction is performed using a hot start polymerase. In some embodiments, the primer extension reaction is performed using MyTaq polymerase.

In a fourth aspect, the invention relates to a method of adapter ligation to create a strand retained library of nucleic acids with desired and undesired nucleic acids, comprising: (a) mixing a pool of templates comprising an undesired nucleic acid and a desired nucleic acid with a plurality of partial duplex primers each comprising a 3' overhang; (b) annealing to the templates the plurality of partial duplex primers; (c) performing primer extension reaction along the templates, thereby forming double-stranded nucleic acids each comprising a primer extension product; (d) ligating an adapter to at least one 5' end of the primer extension product; and (e) cleaving the primer extension products from the double-stranded nucleic acids with a cleavage agent that is specific for nucleic acids comprising the one or more nucleotides. In some embodiments, the plurality of partial duplex primers comprise at least two partial duplex primers with dissimilar 3' overhang sequences. In some embodiments, the plurality of partial duplex primers comprise a shared sequence within a double-stranded portion. In some embodiments, the strand of the plurality of partial duplex primers with the 3' overhang lacks adenines in the shared sequence within the double-stranded portion. In some embodiments, the method further comprising a step comprising performing a primer extension reaction along the adapter. In some embodiments, the primer extension reaction is performed in the presence of one or more non-canonical nucleotides. In some embodiments, step e comprises cleaving a base portion of the one or more non-canonical nucleotides, thereby forming an abasic site. In some embodiments, the cleavage agent comprises a glycosylase. In some embodiments, the glycosylase is UNG or UDG. In some embodiments, the cleavage agent comprises a primary amine. In some embodiments, the cleavage agent comprises a polyamine. In some embodiments, the polyamine is DMED. In some embodiments, the cleavage agents comprises a glycosylase and a polyamine. In some embodiments, the cleavage agent comprises endonuclease V. In some embodiments, the one or more non-canonical nucleotides comprise uracil or inosine. In some embodiments, the pool of templates is generated by i. performing a first strand synthesis on an RNA in the presence of the one or more non-canonical nucleotides, thereby forming a first strand synthesis product; and ii. performing a fragmentation reaction. In some embodiments, the method further comprises selectively cleaving the RNA. In some embodiments, selectively cleaving the RNA comprises treatment with RNAse H. In some embodiments, the fragmentation reaction comprises utilizing a cleavage agent targeting the one or more non-canonical nucleotides. In some embodiments, the fragmentation reaction comprises cleaving a base portion of the one or more non-canonical nucleotides, thereby forming an abasic site. In some embodiments, the cleavage agent comprises a glycosylase. In some embodiments, the glycosylase is UNG or UDG. In some embodiments, the cleavage agent comprises a primary amine. In some embodiments, the cleavage agent comprises a polyamine. In some embodiments, the polyamine is DMED. In some embodiments, the cleavage agents comprises a glycosylase and a polyamine. In some embodiments, the cleavage agent comprises endonuclease V. In some embodiments, the adapter comprises a recognition sequence for a restriction endonuclease specific for double-stranded DNA. In some embodiments, the method further comprises, (f) hybridizing a probe to a sequence of the undesired nucleic acid; (g) extending the probe with a DNA polymerase, thereby producing a partial duplex nucleic acid, and (h) treating the partial duplex nucleic acid with a restriction endonuclease specific for double-stranded DNA, thereby cleaving double-stranded DNA fragments at the recognition sequence. In some embodiments, the method further comprises performing PCR with a set of primers that are hybridizable to a sequence reverse complimentary to the adapter and the shared sequence of the partial duplex primers opposite the 3' overhang, thereby amplifying a desired nucleic acid in the pool of templates. In some embodiments, the method further comprises sequencing a portion of the desired nucleic acid. In some embodiments, the pool of templates originates from a population of sorted cells. In some embodiments, the pool of templates originates from a single cell. In some embodiments, the method further comprises sorting cells into a multiwell plate, microarray, microfluidic device, or slide and thereby generating the population of sorted cells. In some embodiments, the sorting is performed according to a cell surface marker. In some embodiments, the sorting is performed according to optical properties of the cells. In some embodiments, the sorting is performed according to cell size. In some embodiments, the pool of templates comprises bacterial ribosomal RNA, mitochondrial DNA, human globin mRNA, human cytoplasmic rRNA, human mitochondrial rRNA, grape cytoplasmic rRNA, grape mitochondrial rRNA, or grape chloroplast rRNA. In some embodiments, the restriction endonuclease is BspQI. In some embodiments, the primer extension reaction is performed using a hot start polymerase. In some embodiments, the primer extension reaction is performed using MyTaq polymerase.

According to any of the aspects, the invention relates to partially, substantially, or completely depleting undesired sequences, wherein at least 2, 5, 10, 15, 20, 25, 30, 35, 40, 45, 50, 55, 60, 65, 70, 75, 80, 85, 90, 95, 98, 99, 99.5, 99.8, 99.9, 99.99 percent or more of some or all of the undesired sequences is depleted and, optionally, partially substantially, or completely retaining desired sequences, wherein less than 98, 95, 90, 85, 80, 75, 70, 65, 60, 55, 50, 45, 40, 35, 30, 25, 20, 15, 10, 5, 2, 1, 0.5, 0.2, 0.1, 0.05, 0.01 percent or less of some or all of the desired sequences is depleted. In some embodiments, the methods in any of the aspects deplete some or all of the undesired sequences completely. In some embodiments, the methods in any of the aspects retain some or all of the desired sequences completely. In any of the aspects, the methods described herein may decrease the abundance ratio between an undesired and a desired nucleic acid sequence, between some undesired and some desired nucleic acid sequences, or between all undesired and all desired nucleic acid sequences by 1.1, 1.2, 1.5, 2, 3, 4, 5, 6, 7, 8, 9, 10, 15, 20, 25, 30, 35, 40, 50, 60, 75, 100, 200, 500, 1000, 5000, 10000, 100000, 1000000 fold or more.

In various aspects, the invention relates to kits. In a first aspect, the invention relates to a kit comprising a restriction endonuclease, a first adapter comprising one or more non-canonical nucleotides on one strand and lacking 5' phosphates, a second adapter lacking said one or more non-canonical nucleotides and lacking 5' phosphates, a ligase, a polymerase, a cleavage agent, a library of probes, a set of primers specific to the adaptor sequences; wherein the second adapter comprises a recognition sequence for the restriction endonuclease.

In a second aspect, the invention relates to a kit comprising a restriction endonuclease, a first adapter lacking 5' phosphates, a plurality of partial duplex primers each comprising a 3' overhang and comprising a shared sequence within a double-stranded portion, a ligase, a polymerase, a cleavage agent, a library of probes capable of acting as a primer for a primer extension reaction; and a primer that is hybridizable a sequence reverse complimentary to the adapter; wherein the first adapter comprises a recognition sequence for the restriction endonuclease; and wherein the plurality of partial duplex primers comprise at least two partial duplex primers with dissimilar 3' overhang sequences.

In a third aspect, the invention relates to a kit comprising a restriction endonuclease, a first adapter lacking 5' phosphates, a plurality of partial duplex primers each comprising a 3' overhang, comprising a shared sequence within a double-stranded portion, and the strand of the plurality of partial duplex primers with the 3' overhang lacking adenines in the shared sequence within the double-stranded portion, a ligase, a polymerase, a cleavage agent, a library of probes capable of acting as a primer for a primer extension reaction; and a set of primers that are hybridizable to a sequence reverse complimentary to the adapter and the shared sequence of the partial duplex primers opposite the 3' overhang; wherein the first adapter comprises a recognition sequence for the restriction endonuclease; and wherein the plurality of partial duplex primers comprise at least two partial duplex primers with dissimilar 3' overhang sequences.

In any of the aspects: The restriction endonuclease may be BspQI. In some embodiments, the polymerase is a hot start polymerase, e.g. MyTaq. In some embodiments, the kit further comprises one or more non-canonical nucleotides. In some embodiments, the one or more non-canonical nucleotides comprise uracil or inosine. In some embodiments, the cleavage agent comprises a glycosylase. In some embodiments, the glycosylase is UNG or UDG. In some embodiments, the cleavage agent comprises a primary amine. In some embodiments, the cleavage agent comprises a polyamine. In some embodiments, the polyamine is DMED. In some embodiments, the cleavage agent comprises a glycosylase and a polyamine. In some embodiments, the cleavage agent comprises endonuclease V.

Kits for performing any of the methods described herein are another feature of the invention. Such kits may include reagents, enzymes and platforms for selective enrichment, amplification, and sequencing of nucleic acids. In one embodiment, a kit is provided comprising: a) an adaptor or several adaptors, b) one or more of oligonucleotide primers, and c) reagents for amplification. In another embodiment, the kit further comprises a sequence and dsDNA-specific nucleic acid modifying enzyme, such as a restriction enzyme. In yet another embodiment, the kit further comprises reagents for sequencing. A kit will preferably include instructions for employing the kit components as well as the use of any other reagent not included in the kit.

In any of the aspects, the methods, compositions and kits of the invention relate to primer probes that are capable of acting as primers targeting sequences on undesired nucleic acids.

In any of the aspects, the invention relates to a set of primer probes that are generated by, compiling undesired nucleic acid sequences, optionally compiling desired nucleic acid sequences, choosing one or more strands in each undesired nucleic acid sequence, computationally fragmenting each undesired nucleic acid sequence to stretches of a selected length, for example 40-200, 50-180, 60-150, 70-120, 80-110, 90-100 bases long, selecting a target melting temperature range, for example 40-90, 45-85, 50-80, 55-75, 60-70, 55-65° C. etc., for amplification primers, optionally selecting a target length range, for example 10-80, 11-70, 12-65, 13-60, 14-55, 15-50, 16-45, 17-40, 18-35, 19-30, 10-30, 11-28, 12-26, 13-24, 14-22, 15-20, 10-20, 11-19, 12-18, 13-17, 14-16 nucleotides long, etc., for amplification primers, designing qualified amplification primers targeting a portion in the one or more strands in each undesired nucleic acid sequence, with a predicted melting temperature within the target temperature range and, optionally, with a length within the target length range, optionally determining whether one or more of the designed amplification primers are hybridizable to one or more of the desired nucleic acid sequences and optionally removing any such designed amplification primers from a list of qualified amplification primers, and synthesizing oligonucleotides from the list of qualified amplification primers. Those of skill in the art appreciate that the target melting temperature range and the target length range may fall within any range bounded by any of these values (e.g., 45-55° C. or 1-12 nucleotides long etc.). In some embodiments, the oligonucleotide synthesis is performed using standard phosphoramidite chemistries known in the art. In some embodiments, the synthesized oligonucleotides are pooled.

In any of the aspects the set of primer probes targeting undesired nucleic acid sequences may comprise between 50-10000, 55-5000, 60-1000, 70-500, 80-250, 90-200, 100-180, 110-170, 120-180, 130-170, 140-160, 100-150, 250-1000 distinct oligonucleotides. Thus, a composition of the invention comprises, consists essentially of, or consists of, a set of at least 50, 100, 150, 200, 250 different oligonucleotides wherein said oligonucleotides selectively hybridize to mitochondrial RNA, mitochondrial DNA, human rRNA, mitochondrial rRNA, bacterial ribosomal RNA, mitochondrial DNA, human globin mRNA, human cytoplasmic rRNA, human mitochondrial rRNA, grape cytoplasmic rRNA, grape mitochondrial rRNA, or grape chloroplast rRNA. Such composition can be isolated in a vial (e.g., a reagent). Each of the oligonucleotides can have the properties (e.g., size and Tm) described herein. Those of skill in the art appreciate that the target melting temperature range and the target length range may fall within any range bounded by any of these values (e.g., 60-70, 160-200, or 150-250 etc.).

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following description that sets forth illustrative embodiments, in which the principles of the invention are utilized, and the accompanying drawings of which:

FIG. 1 depicts the elimination of non-desired nucleic acid sequences from a nucleic acid library of single-stranded DNA fragments using insert-dependent adaptor cleavage (InDA-C). The gene-specific primer (GSP) anneals to its complementary sequence only, creating a population of double-stranded or partially double-stranded molecules following polymerase-based extension. Subsequent treatment with an adaptor-specific restriction endonuclease cleaves only fragments which were activated by the GSP extension reaction, thereby removing one of the PCR priming sites from the non-desired fragments. PCR amplification produces a library that is enriched for the nucleic acid sequences of interest.

FIG. 2 depicts a summary of the results from an experiment depleting bacterial rRNA fragments from strand-specific whole transcriptome cDNA libraries, as outlined in Example 1.

FIG. 3 depicts a comparison of the expression profiles from the four test libraries described in Example 1.

DETAILED DESCRIPTION OF THE INVENTION

General

Figure 4:
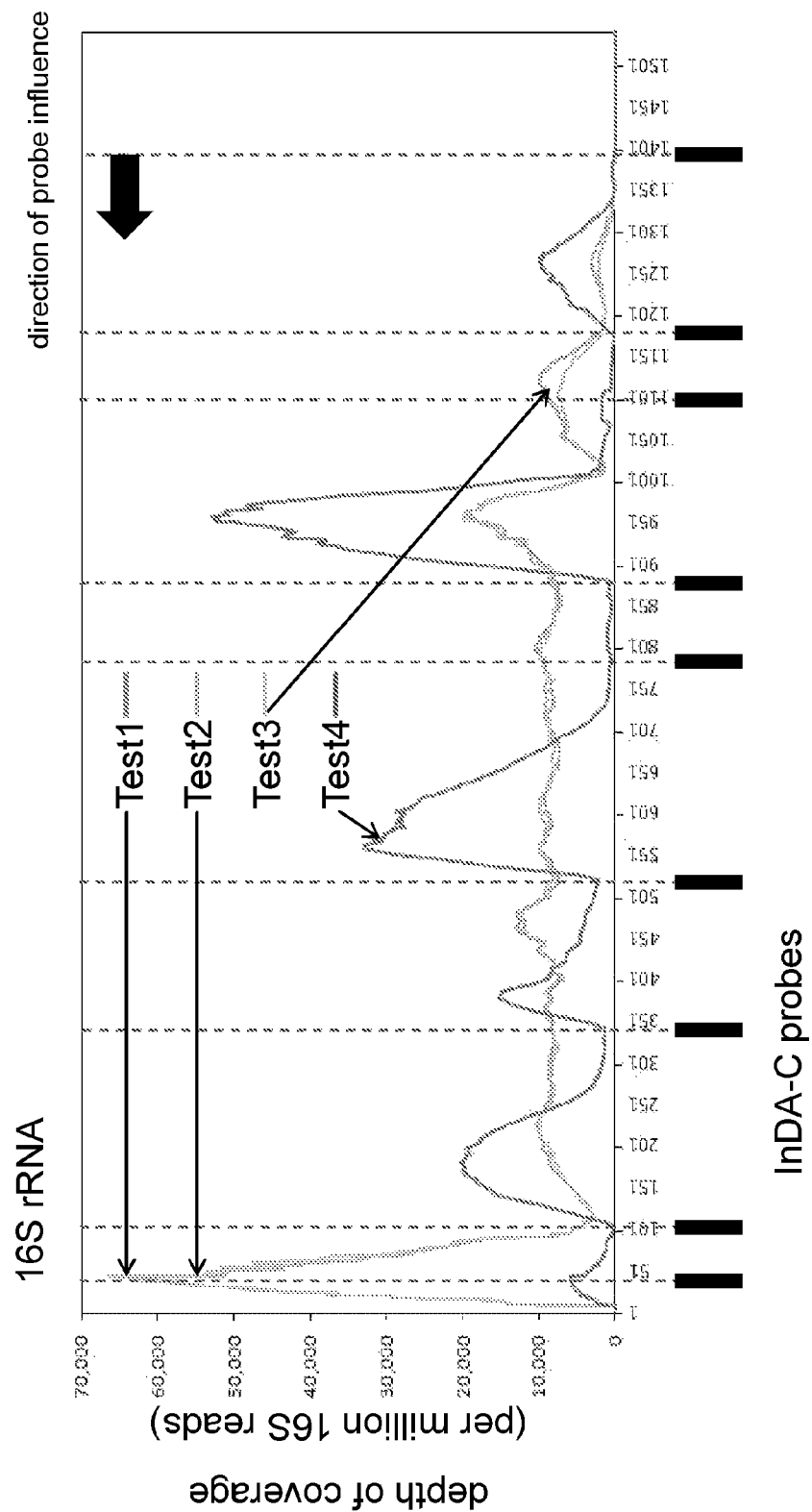
FIG. 4 depicts targeted depletion of 16S rRNA sites by universal prokaryotic InDA-C probes in Example 1.

The methods of the invention can be used for the generation of next generation sequencing (NGS) libraries in which non-desired nucleic acid sequences have been depleted or substantially reduced. Such methods are useful, for example, for the production of sequencing libraries with reduced ribosomal RNA representation, and for the enrichment of nucleic acid sequences of interest in a nucleic acid library. Altogether, the methods of the present invention provide an improvement over the existing methods for creating NGS libraries which are depleted from non-desired nucleic acid sequences because the elimination of non-desired nucleic acid sequences occurs after the generation of the nucleic acid library, thereby enabling starting with a non-distorted, unbiased nucleic acid template population.

The methods and compositions of the invention can be used for directional library construction. The methods of the invention can further be used to generate adaptor ligated single stranded DNA samples, wherein the orientation of the adaptor is fixed.

As used herein, unless otherwise indicated, some inventive embodiments herein contemplate numerical ranges. A variety of aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range as if explicitly written out. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. When ranges are present, the ranges include the range endpoints.

Reference will now be made in detail to exemplary embodiments of the invention. While the disclosed methods and compositions will be described in conjunction with the exemplary embodiments, it will be understood that these exemplary embodiments are not intended to limit the invention. On the contrary, the invention is intended to encompass alternatives, modifications and equivalents, which may be included in the spirit and scope of the invention.

Unless otherwise specified, terms and symbols of genetics, molecular biology, biochemistry and nucleic acid used herein follow those of standard treatises and texts in the field, e.g. Kornberg and Baker, *DNA Replication*, Second Edition (W.H. Freeman, New York, 1992); Lehninger, *Biochemistry*, Second Edition (Worth Publishers, New York, 1975); Strachan and Read, Human *Molecular Genetics*, Second Edition (Wiley-Liss, New York, 1999); Eckstein, editor, *Oligonucleotide and Analogs: A Practical Approach* (Oxford University Press, New York, 1991); Gait, editor, *Oligonucleotide Synthesis: A Practical Approach* (IRL Press, Oxford, 1984); and the like.

Oligonucleotides of the Invention

As used within the invention, the term "oligonucleotide" refers to a polynucleotide chain, typically less than 200 residues long, most typically between 15 and 100 nucleotides long, but also intended to encompass longer polynucleotide chains. Oligonucleotides may be single- or double-stranded. The terms "oligonucleotide probe" or "probe", as used in this invention, refer to an oligonucleotide capable of hybridizing to a complementary nucleotide sequence. As used in this invention, the term "oligonucleotide" may be used interchangeably with the terms "primer", "adaptor" and "probe".

As used herein, the terms "hybridization"/"hybridizing" and "annealing" are used interchangeably and refer to the pairing of complementary nucleic acids.

The term "primer", as used herein, refers to an oligonucleotide, generally with a free 3' hydroxyl group that is capable of hybridizing with a template (such as a target polynucleotide, target DNA, target RNA or a primer extension product) and is also capable of promoting polymerization of a polynucleotide complementary to the template. A primer may contain a non-hybridizing sequence that constitutes a tail of the primer. A primer may still be hybridizing to a target even though its sequences are not fully complementary to the target.

The primers of the invention are generally oligonucleotides that are employed in an extension reaction by a polymerase along a polynucleotide template, such as in PCR or cDNA synthesis, for example. The oligonucleotide primer is often a synthetic polynucleotide that is single stranded, containing a sequence at its 3'-end that is capable of hybridizing with a sequence of the target polynucleotide. Normally, the 3' region of the primer that hybridizes with the target nucleic acid has at least 80%, preferably 90%, more preferably 95%, most preferably 100%, complementarity to a sequence or primer binding site.

"Complementary", as used herein, refers to complementarity to all or only to a portion of a sequence. The number of nucleotides in the hybridizable sequence of a specific oligonucleotide primer should be such that stringency conditions used to hybridize the oligonucleotide primer will prevent excessive random non-specific hybridization. Usually, the number of nucleotides in the hybridizing portion of the oligonucleotide primer will be at least as great as the defined sequence on the target polynucleotide that the oligonucleotide primer hybridizes to, namely, at least 5, at least 6, at least 7, at least 8, at least 9, at least 10, at least 11, at least 12, at least 13, at least 14, at least 15, at least about 20, and generally from about 6 to about 10 or 6 to about 12 of 12 to about 200 nucleotides, usually about 10 to about 50 nucleotides. In general, the target polynucleotide is larger than the oligonucleotide primer or primers as described previously.

Complementary may generally refer to the capacity for precise pairing between two nucleotides. I.e., if a nucleotide at a given position of a nucleic acid is capable of hydrogen bonding with a nucleotide of another nucleic acid, then the two nucleic acids are considered to be complementary to one another at that position. A "complement" may be an exactly or partially complementary sequence. Complementarity between two single-stranded nucleic acid molecules may be "partial," in which only some of the nucleotides bind, or it may be complete when total complementarity exists between the single-stranded molecules. The degree of complementarity between nucleic acid strands has significant effects on the efficiency and strength of hybridization between nucleic acid strands. Two sequences that are partially complementary may have, for example, at least 90% identity, or at least 95%, 96%, 97%. 98%, or 99% identity sequence over a sequence of at least 7 nucleotides, more typically in the range of 10-30 nucleotides, and often over a sequence of at least 14-25 nucleotides. It will be understood that the 3' base of a primer sequence will desirably be perfectly complementary to corresponding bases of the target nucleic acid sequence to allow priming to occur.

"Specific hybridization" refers to the binding of a nucleic acid to a target nucleotide sequence in the absence of substantial binding to other nucleotide sequences present in the hybridization mixture under defined stringency conditions. Those of skill in the art recognize that relaxing the stringency of the hybridization conditions allows sequence mismatches to be tolerated. In particular embodiments, hybridizations are carried out under stringent hybridization conditions.

"Tm" refers to "melting temperature", which is the temperature at which a population of double-stranded nucleic acid molecules becomes half-dissociated into single strands. The Tm of a single stranded oligonucleotide, as used herein, refers to the Tm of a double stranded molecule comprising the oligonucleotide and its exact complement. Tm may be determined by calculation. Specifically, the Tm of an oligonucleotide may be a calculated Tm according to the equation: "Tm (° C.)=4(G+C)+2(A+T)" (Thein and Wallace, 1986, in Human genetic disorders, p 33-50, IRL Press, Oxford UK, incorporated herein by reference).

In some cases, the identity of the investigated target polynucleotide sequence is known, and hybridizable primers can be synthesized precisely according to the antisense sequence of the aforesaid target polynucleotide sequence. In other cases, when the target polynucleotide sequence is unknown, the hybridizable sequence of an oligonucleotide primer is a random sequence. Oligonucleotide primers comprising random sequences may be referred to as "random primers", as described below. In yet other cases, an oligonucleotide primer such as a first primer or a second primer comprises a set of primers such as for example a set of first primers or a set of second primers. In some cases, the set of first or second primers may comprise a mixture of primers designed to hybridize to a plurality (e.g. 2, 3, 4, about 6, 8, 10, 20, 40, 80, 100, 125, 150, 200, 250, 300, 400, 500, 600, 800, 1000, 1500, 2000, 2500, 3000, 4000, 5000, 6000, 7000, 8000, 10,000, 20,000, 25,000 or more) of target sequences.

In some cases, the plurality of target sequences may comprise a group of related sequences, random sequences, a whole transcriptome or fraction (e.g. substantial fraction) thereof, or any group of sequences such as mRNA.

In some embodiments of the invention, random priming is used. A "random primer", as used herein, is a primer that generally comprises a sequence that is not designed based on a particular or specific sequence in a sample, but rather is based on a statistical expectation (or an empirical observation) that a sequence of the random primer is hybridizable, under a given set of conditions, to one or more sequences in a sample. A random primer will generally be an oligonucleotide or a population of oligonucleotides comprising a random sequence(s) in which the nucleotides at a given position on the oligonucleotide can be any of the four nucleotides A, T, G, C or any of their analogs. A random primer may comprise a 5' or 3' region that is a specific, non-random sequence. In some embodiments of the invention, the random primers comprise tailed primers with a 3' random sequence region and a 5' non-hybridizing region that comprises a specific, common adaptor sequence. The sequence of a random primer, or its complement, may or may not be naturally occurring, and may or may not be present in a pool of sequences in a sample of interest. A "random primer" can also refer to a primer that is a member of a population of primers (a plurality of random primers) which are collectively designed to hybridize to a desired target sequence or sequences.

The term "adaptor", as used herein, refers to an oligonucleotide of known sequence, the ligation or incorporation of which to a target polynucleotide or a target polynucleotide strand of interest enables the generation of amplification-ready products of the target polynucleotide or the target polynucleotide strand of interest. Various adaptor designs are envisioned. Various ligation processes and reagents are known in the art and can be useful for carrying out the methods of the invention. For example, blunt ligation can be employed. Similarly, a single dA nucleotide can be added to the 3'-end of the double-stranded DNA product, by a polymerase lacking 3'-exonuclease activity and can anneal to an adaptor comprising a dT overhang (or the reverse). This design allows the hybridized components to be subsequently ligated (e.g., by T4 DNA ligase). Other ligation strategies and the corresponding reagents and known in the art and kits and reagents for carrying out efficient ligation reactions are commercially available (e.g., from New England Biolabs, Roche).

The term "insert-dependent adaptor cleavage" (InDA-C), as used herein, refers to a multi-step process for depleting or removing specific nucleotide sequences from a nucleotide library. The first step comprises annealing sequence-specific oligonucleotides, designed to be complementary to non-desired nucleic acid sequences or sequences directly adjacent to regions of non-desired sequence, to single-stranded nucleic acid templates with adaptors of fixed orientation attached at each end. The adaptors at the 5' ends of each fragment contain a recognition sequence for a restriction endonuclease specific for double-stranded DNA. Following the annealing of the sequence-specific oligonucleotides, primer extension is performed, thereby creating double-stranded DNA fragments in the regions where the oligonucleotides are complementary to the single-stranded nucleic acid templates. The resulting nucleic acid library, containing both single-stranded and double-stranded fragments, is treated with the restriction endonuclease, resulting in cleavage at the restriction endonuclease site of the double-stranded fragments only, and thus, the removal of the adaptor at one end of the fragments containing the non-desired nucleic acid sequences. Following adaptor cleavage, PCR may be performed using primers specific to each adaptor, resulting in amplification of the desired nucleic acid fragments only (i.e. amplification of the fragments containing both PCR priming sites on the same template). Insert-dependent adaptor cleavage is depicted in FIG. 1.

Methods for designing oligonucleotides of various lengths and melting temperatures that are capable of hybridizing or that are excluded from hybridizing to a selected list of sequences are well known in the art and are described in further detail in EP 1957645B1, which is incorporated herein by reference in its entirety.

Nucleic Acid Modifying Enzymes

The methods of the invention employ the use of nucleic acid (NA) modifying enzymes. The nucleic acid modifying enzyme can be DNA-specific modifying enzyme. The NA-modifying enzyme can be selected for specificity for double-stranded DNA. The enzyme can be a duplex-specific endonuclease, a blunt-end frequent cutter restriction enzyme, or other restriction enzyme. Examples of blunt-end cutters include DraI or SmaI. The NA-modifying enzyme can be an enzyme provided by New England Biolabs. The NA-modifying enzyme can be a homing endonuclease (a homing endonuclease can be an endonuclease that does not have a stringently-defined recognition sequence). The NA-modifying enzyme can be a high fidelity endonuclease (a high fidelity endonuclease can be an engineered endonuclease that has less "star activity" than the wild-type version of the endonuclease).

In some embodiments, the NA-modifying enzyme is a sequence- and duplex-specific DNA-modifying restriction endonuclease. In a preferred embodiment, the NA-acid modifying enzyme is the enzyme BspQI, a type IIS restriction endonuclease.

Attachment of Adaptors
Ligation

The terms "joining" and "ligation" as used herein, with respect to two polynucleotides, such as a stem-loop adaptor/primer oligonucleotide and a target polynucleotide, refers to the covalent attachment of two separate polynucleotides to produce a single larger polynucleotide with a contiguous backbone. Methods for joining two polynucleotides are known in the art, and include without limitation, enzymatic and non-enzymatic (e.g. chemical) methods. Examples of ligation reactions that are non-enzymatic include the non-enzymatic ligation techniques described in U.S. Pat. Nos. 5,780,613 and 5,476,930, which are herein incorporated by reference. In some embodiments, an adaptor oligonucleotide is joined to a target polynucleotide by a ligase, for example a DNA ligase or RNA ligase. Multiple ligases, each having characterized reaction conditions, are known in the art, and include, without limitation NAD$^+$-dependent ligases including tRNA ligase, Taq DNA ligase, *Thermus filiformis* DNA ligase, *Escherichia coli* DNA ligase, Tth DNA ligase, *Thermus scotoductus* DNA ligase (I and II), thermostable ligase, Ampligase thermostable DNA ligase, VanC-type ligase, 9° N DNA Ligase, Tsp DNA ligase, and novel ligases discovered by bioprospecting; ATP-dependent ligases including T4 RNA ligase, T4 DNA ligase, T3 DNA ligase, T7 DNA ligase, Pfu DNA ligase, DNA ligase 1, DNA ligase III, DNA ligase IV, and novel ligases discovered by bioprospecting; and wild-type, mutant isoforms, and genetically engineered variants thereof. Ligation can be between polynucleotides having hybridizable sequences, such as complementary overhangs. Ligation can also be between two blunt ends. Generally, a 5' phosphate is utilized in a ligation reaction.

The 5' phosphate can be provided by the target polynucleotide, the adaptor oligonucleotide, or both. 5' phosphates can be added to or removed from polynucleotides to be joined, as needed. Methods for the addition or removal of 5' phosphates are known in the art, and include without limitation enzymatic and chemical processes. Enzymes useful in the addition and/or removal of 5' phosphates include kinases, phosphatases, and polymerases. In some embodiments, both of the two ends joined in a ligation reaction (e.g. an adaptor end and a target polynucleotide end) provide a 5' phosphate, such that two covalent linkages are made in joining the two ends. In some embodiments, only one of the two ends joined in a ligation reaction (e.g. only one of an adaptor end and a target polynucleotide end) provides a 5' phosphate, such that only one covalent linkage is made in joining the two ends. In some embodiments, only one strand at one or both ends of a target polynucleotide is joined to an adaptor oligonucleotide. In some embodiments, both strands at one or both ends of a target polynucleotide are joined to an adaptor oligonucleotide. In some embodiments, 3' phosphates are removed prior to ligation. In some embodiments, an adaptor oligonucleotide is added to both ends of a target polynucleotide, wherein one or both strands at each end are joined to one or more adaptor oligonucleotides. When both strands at both ends are joined to an adaptor oligonucleotide, joining can be followed by a cleavage reaction that leaves a 5' overhang that can serve as a template for the extension of the corresponding 3' end, which 3' end may or may not include one or more nucleotides derived from the adaptor oligonucleotide. In some embodiments, a target polynucleotide is joined to a first adaptor oligonucleotide on one end and a second adaptor oligonucleotide on the other end. In some embodiments, the target polynucleotide and the adaptor to which it is joined comprise blunt ends. In some embodiments, separate ligation reactions are carried out for each sample, using a different first adaptor oligonucleotide comprising at least one barcode sequence for each sample, such that no barcode sequence is joined to the target polynucleotides of more than one sample. A target polynucleotide that has an adaptor/primer oligonucleotide joined to it is considered "tagged" by the joined adaptor.

In some embodiments, joining of an adaptor/primer to a target polynucleotide produces a joined product polynucleotide having a 3' overhang comprising a nucleotide sequence derived from the adaptor/primer. In some embodiments, a primer oligonucleotide comprising a sequence complementary to all or a portion of the 3' overhang is hybridized to the overhang and extended using a DNA polymerase to produce a primer extension product hybridized to one strand of the joined product polynucleotide. The DNA polymerase may comprise strand displacement activity, such that one strand of the joined product polynucleotide is displaced during primer extension.

Methods of Strand-Specific Selection

The compositions and methods provided herein are useful for retaining directional information in double-stranded DNA.

The terms "strand specific" or "directional", as used herein, may refer to the ability to differentiate in a double-stranded polynucleotide between the original template strand and the strand that is complementary to the original template strand. Further, methods and compositions of the invention, in various embodiments, enable adapter ligation in a strand specific manner. In various embodiments, an adapter is incorporated at a chosen end of a strand, preferably a selected strand. Further, an adapter may be incorporated in a chosen orientation. In various embodiments, strand specificity, directionality and orientation is accomplished by selecting or enriching the desired configurations or strands.

In some embodiments, the methods of the invention are used to preserve information about the direction of single-stranded nucleic acid molecules while generating double-stranded polynucleotides more suitable for molecular cloning applications. One of the strands of the double-stranded polynucleotide is synthesized so that it has at least one modified nucleotide incorporated into it along the entire length of the strand. In some embodiments, the incorporation of the modified nucleotide marks the strand for degradation or removal.

The term "first strand synthesis" refers to the synthesis of the first strand using the original nucleic acid (RNA or DNA) as a starting template for the polymerase reaction. The nucleotide sequence of the first strand corresponds to the sequence of the complementary strand.

The term "second strand synthesis" refers to the synthesis of the second strand that uses the first strand as a template for the polymerase reaction. The nucleotide sequence of the second strand corresponds to the sequence of the original nucleic acid template.

The term "unmodified dNTPs" or "classic dNTPs" refers to the four deoxyribonucleotide triphosphates dATP (deoxyadenosine triphosphate), dCTP (deoxycytidine triphosphate), dGTP (deoxyguanosine triphosphate) and dTTP (deoxythymidine triphosphate) that are normally used as building blocks in the synthesis of DNA. Similarly, the term "canonical dNTP" is used to refer to the four deoxyribonucleotide triphosphates dATP, dCTP, dGTP and dTTP that are normally found in DNA. Generally, nucleotides are present in nucleoside triphosphate form in a solution for a primer extension reaction. During primer extension reactions, they are typically incorporated into a polynucleotide in nucleoside form, e.g. adenosine, thymidine, guanosine, cytidine, uridine, etc. losing two phosphates, while one of the phosphates forms part of the polynucleotide backbone. The nucleobase, e.g. adenine, guanine, thymine, cytosine, uracil etc., of the nucleotides may be removed according to various embodiments of the invention, forming an abasic site. Various methods for removing nucleobases from polynucleotides, forming abasic sites are explained in detail herein and known in the art.

The term "canonical" as used herein, refers to the nucleic acid bases adenine, cytosine, guanine and thymine that are commonly found in DNA or their deoxyribonucleotide or deoxyribonucleoside analogs. The term "noncanonical" refers to nucleic acid bases in DNA other than the four canonical bases in DNA, or their deoxyribonucleotide or deoxyribonucleoside analogs. Although uracil is a common nucleic acid base in RNA, uracil is a non-canonical base in DNA.

The term "modified nucleotide" or "modified dNTP", as used herein, refers to any molecule suitable for substituting one corresponding unmodified or classic dNTP. Such modified nucleotide must be able to undergo a base pair matching identical or similar to the classic or unmodified dNTP it replaces. The modified nucleotide or dNTP can be suitable for specific degradation in which it is selectively degraded by a suitable degrading agent, thus rendering the DNA strand containing at least one modified and degraded dNTP essentially unfit for amplification and/or hybridization. Alternatively, the modified nucleotide must mark the DNA strand containing the modified nucleotide eligible for selective removal or facilitate separation of the polynucleotide strands. Such a removal or separation can be achieved by molecules, particles or enzymes interacting selectively with the modified nucleotide, thus selectively removing or marking for removal only one polynucleotide strand.

As used in this application, the term "strand marking" refers to any method for distinguishing between the two strands of a double-stranded polynucleotide. The term "selection" refers to any method for selecting between the two strands of a double-stranded polynucleotide. The term "selective removal" or "selective marking for removal" refers to any modification to a polynucleotide strand that renders that polynucleotide strand unsuitable for a downstream application, such as amplification or hybridization.

In a one embodiment, the selection is done by incorporation of at least one modified nucleotide into one strand of a synthesized polynucleotide, and the selective removal is by treatment with an enzyme that displays a specific activity towards the at least one modified nucleotide. In a preferred embodiment, the modified nucleotide being incorporated into one strand of the synthesized polynucleotide is deoxyuridine triphosphate (dUTP), replacing dTTP in the dNTP mix, and the selective removal of the marked strand from downstream applications is carried by the nuclease Uracil-N-Glycosylase (UNG). UNG selectively degrades dUTP while it is neutral towards other dNTPs and their analogs. Treatment with UNG results in the cleavage of the N-glycosylic bond and the removal of the base portion of dU residues, forming abasic sites. In a preferred embodiment, the UNG treatment is done in the presence of an apurinic/apyrimidinic endonuclease (APE) to create nicks at the abasic sites. Consequently, a polynucleotide strand with incorporated dUTP that is treated with UNG/APE is cleaved and unable to undergo amplification by a polymerase. In another embodiment, nick generation and cleavage is achieved by treatment with a polyamine, such as N,N'-dimethylethylenediamine (DMED), or by heat treatment. In a preferred embodiment, UNG treatment is conducted in a reaction buffer containing about 32 mM DMED.

As used in this application, the term "at least one nucleotide" or "at least one modified nucleotide" refers to a plurality of dNTP molecules of the same kind or species. Thus, use of "one modified nucleotide" refers to the replacement in the dNTP mix of one of the classic dNTPs dATP, dCTP, dGTP or dTTP with a corresponding modified nucleotide species.

In a preferred embodiment, the at least one modified nucleotide is dUTP, replacing dTTP in the dNTP mix. In another embodiment, the at least one modified nucleotide is a biotinylated dNTP. In another embodiment, the at least one modified nucleotide contains a thio group. In another embodiment, the at least one modified nucleotide is an aminoallyl dNTP. In yet another embodiment, the at least one modified nucleotide is inosine, replacing dGTP in the dNTP mix.

In some embodiments, the methods of the invention are used for construction of directional cDNA libraries. Strand marking is necessary, but not sufficient for construction of directional cDNA libraries when using adaptors that are not polarity-specific, i.e. adaptors generating ligation products with two adaptor orientations. Construction of directional cDNA libraries according to the methods of invention requires strand marking of both the cDNA insert and one of the two adaptors at the ligation strand of the adaptor. A useful feature of the present invention is the ability to switch around the adaptor orientation. For example, in a duplex adaptor system where P1/P2 designates adaptor orientation resulting in sense strand selection and (optional) sequencing, and where the P2 adaptor has at least one modified nucleotide incorporated along the ligation strand of the adaptor, modification of the protocol such that the P1 adaptor (as opposed to P2 adaptor) has at least one modified nucleotide incorporated along the ligation strand allows for antisense strand selection and (optional) sequencing.

The methods of the present invention may further include a step of cleaving the input nucleic acid template. In some cases, the input nucleic acid template may be cleaved with an agent such as an enzyme. In the embodiment where the polynucleotide comprises a non-canonical nucleotide, the polynucleotide may be treated with an agent, such as an enzyme, capable of generally, specifically, or selectively cleaving a base portion of the non-canonical deoxyribonucleoside to create an abasic site. As used herein, "abasic site" encompasses any chemical structure remaining following removal of a base portion (including the entire base) with an agent capable of cleaving a base portion of a nucleotide, e.g., by treatment of a non-canonical nucleotide (present in a polynucleotide chain) with an agent (e.g., an enzyme, acidic conditions, or a chemical reagent) capable of effecting cleavage of a base portion of a non-canonical nucleotide. In some embodiments, the agent (such as an enzyme) catalyzes hydrolysis of the bond between the base portion of the non-canonical nucleotide and a sugar in the non-canonical nucleotide to generate an abasic site comprising a hemiacetal ring and lacking the base (interchangeably called "AP" site), though other cleavage products are contemplated for use in the methods of the invention. Suitable agents and reaction conditions for cleavage of base portions of non-canonical nucleotides include: N-glycosylases (also called "DNA glycosylases" or "glycosidases") including Uracil N-Glycosylase ("UNG"; specifically cleaves dUTP) (interchangeably termed "uracil DNA glycosylase"), hypoxanthine-N-Glycosylase, and hydroxy-methyl cytosine-N-glycosylase; 3-methyladenine DNA glycosylase, 3- or 7-methylguanine DNA glycosylase, hydroxymethyluracile DNA glycosylase; T4 endonuclease V. See, e.g., Lindahl, PNAS (1974) 71(9):3649-3653; Jendrisak, U.S. Pat. No. 6,190,865 B1 or any of the glycosidases provided in Table 1 or homologues thereof such as enzymes with greater than about 50%, 55%, 60%, 65%, 70%, 75%, 80%, 85%, 90%, 95%, 99%, 99.5%, or higher homology or identity at the amino acid or nucleotide level with any of the glycosydases provided herein. In one embodiment, uracil-N-glycosylase is used to cleave a base portion of the non-canonical nucleotide. In other embodiments, the agent that cleaves the base portion of the non-canonical nucleotide is the same agent that cleaves a phosphodiester backbone at the abasic site.

TABLE 1

Glycosylases in bacteria, yeast and humans

| E. coli | Yeast (S. cerevisiae) | Human | Type | Substrates |
| --- | --- | --- | --- | --- |
| AlkA | Mag1 | | monofunctional | 3-meA, hypoxanthine |
| UDG | Ung1 | UNG | monofunctional | uracil |
| Fpg | Ogg1 | hOGG1 | bifunctional | 8-oxoG, FapyG |
| Nth | Ntg1 Ntg2 | hNTH1 | bifunctional | Tg, hoU, hoC, urea, FapyG |
| Nei | | hNEIL1 | bifunctional | Tg, hoU, hoC, urea, FapyG, FapyA |
| | | hNEIL2 | | AP site, hoU |
| | | hNEIL3 | | unknown |
| MutY | | hMYH | monofunctional | A: 8-oxoG |
| | | hSMUG1 | monofunctional | U, hoU, hmU, fU |
| | | TDG | monofunctional | T: G mispair |
| | | MBD4 | monofunctional | T: G mispair |

Cleavage of base portions of non-canonical nucleotides may provide general, specific or selective cleavage (in the sense that the agent (such as an enzyme) capable of cleaving a base portion of a non-canonical nucleotide generally, specifically or selectively cleaves the base portion of a particular non-canonical nucleotide), whereby substantially all or greater than about 99.9%, 99.5%, 99%, 98.5%, 98%, about 95%, about 90%, about 85%, about 80%, about 75%, about 70%, about 65%, about 60%, about 55%, about 50%, about 45%, or about 40% of the base portions cleaved are base portions of non-canonical nucleotides. However, extent of cleavage can be less. Thus, reference to specific cleavage is exemplary. General, specific or selective cleavage is desirable for control of the fragment size in the methods of generating template polynucleotide fragments of the invention (i.e., the fragments generated by cleavage of the backbone at an abasic site). Reaction conditions may be selected such that the reaction in which the abasic site(s) are created can run to completion, or the reaction may be carried out until 10%, 20%, 30%, 40%, 50%, 60%, 70%, 80%, 90%, 95%, 99%, or about 100% of the non-canonical nucleotides are converted to abasic sites. In some cases, the reaction conditions may be selected such that the reaction in which abasic site(s) are created at between about 10% and about 100% of the one or more non-canonical nucleotides present in the template nucleic acid, between about 20% and about 90%, between about 30% and about 90%, between about 50% and about 90% 95%, 99%, or 100% of the non-canonical nucleotides in the template nucleic acid.

In some embodiments, the template polynucleotide comprising a non-canonical nucleotide is purified following synthesis of the template polynucleotide (to eliminate, for example, residual free non-canonical nucleotides that are present in the reaction mixture). In other embodiments, there is no intermediate purification between the synthesis of the template polynucleotide comprising the non-canonical nucleotide and subsequent steps (such as hybridization of primers, extension of primers to produce primer extension products that do not comprise non-canonical nucleotides, or do not comprise the same non-canonical nucleotides as the template nucleic acid, cleavage of a base portion of the non-canonical nucleotide and cleavage of a phosphodiester backbone at the abasic site).

It is understood that the choice of non-canonical nucleotide can dictate the choice of enzyme to be used to cleave the base portion of that non-canonical enzyme, to the extent that particular non-canonical nucleotides are recognized by particular enzymes that are capable of cleaving a base portion of the non-canonical nucleotide. In some cases, the enzyme is a glycosylase. For example, a template nucleic acid comprising non-canonical nucleotides such as dUTP, 8-oxoguanine, or a methylated purine which may be cleaved by glycosylases may be used in the methods of the present invention. Other suitable non-canonical nucleotides include deoxyinosine triphosphate (dITP), 5-hydroxymethyl deoxycytidine triphosphate (5-OH-Me-dCTP) or any of the non-canonical nucleotides provided in Table 1. See, e.g., Jendrisak, U.S. Pat. No. 6,190,865. A glycosylase such as uracil DNA glycosylase (known as UNG or UDG) which may act on dUTP to provide an abasic site, Ogg1 which may act on 8-oxoguanine to provide an abasic site, or N-methyl purine DNA glycosylase which may act on methylated purines to provide an abasic site may then be used in the methods of the present invention to act on the input nucleic acid template comprising non-canonical nucleotides to initiate a step of cleaving the input nucleic acid template. The enzymes as provided herein may provide N-glycosydic bond cleavage of the input nucleic acid template at the one or more non-canonical nucleotides provided herein to produce one or more abasic (apurinic or apyrimidic) sites.

Additional glycosylases which may be used in the methods of the present invention and their non-canonical nucleotide substrates include 5-methylcytosine DNA glycosylase (5-MCDG), which cleaves the base portion of 5-methylcytosine (5-MeC) from the DNA backbone (Wolffe et al., Proc. Nat. Acad. Sci. USA 96:5894-5896, 1999); 3-methyladenosine-DNA glycosylase I, which cleaves the base portion of 3-methyl adenosine from the DNA backbone (see, e.g. Hollis et al (2000) Mutation Res. 460: 201-210); and/or 3-methyladenosine DNA glycosylase II, which cleaves the base portion of 3-methyladenosine, 7-methylguanine, 7-methyladenosine, and/3-methylguanine from the DNA backbone. See McCarthy et al (1984) EMBO J. 3:545-550. Multifunctional and mono-functional forms of 5-MCDG have been described. See Zhu et al., Proc. Natl. Acad. Sci. USA 98:5031-6, 2001; Zhu et al., Nuc. Acid Res. 28:4157-4165, 2000; and Nedderrnann et al., J. B. C. 271:12767-74, 1996 (describing bifunctional 5-MCDG; Vairapandi & Duker, Oncogene 13:933-938, 1996; Vairapandi et al., J. Cell. Biochem. 79:249-260, 2000 (describing mono-functional enzyme comprising 5-MCDG activity). In some embodiments, 5-MCDG preferentially cleaves fully methylated polynucleotide sites (e.g., CpG dinucleotides), and in other embodiments, 5-MCDG preferentially cleaves a hemi-methylated polynucleotide. For example, mono-functional human 5-methylcytosine DNA glycosylase cleaves DNA specifically at fully methylated CpG sites, and is relatively inactive on hemimethylated DNA (Vairapandi & Duker, supra; Vairapandi et al., supra). By contrast, chick embryo 5-methylcytosine-DNA glycosylase has greater activity directed to hemimethylated methylation sites. In some embodiments, the activity of 5-MCDG is potentiated (increased or enhanced) with accessory factors, such as recombinant CpG-rich RNA, ATP, RNA helicase enzyme, and proliferating cell nuclear antigen (PCNA). See U.S. Patent Publication No. 20020197639 A1. One or more agents may be used. In some embodiments, the one or more agents cleave a base portion of the same methylated nucleotide. In other embodiments, the one or more agents cleave a base portion of different methylated nucleotides. Treatment with two or more agents may be sequential or simultaneous.

Appropriate reaction media and conditions for carrying out the cleavage of a base portion of a non-canonical nucleotide according to the methods of the invention are those that permit cleavage of a base portion of a non-canonical nucleotide. Such media and conditions are known to persons of skill in the art, and are described in various publications, such as Lindahl, PNAS (1974) 71(9):3649-3653; and Jendrisak, U.S. Pat. No. 6,190,865 BI; U.S. Pat. No. 5,035,996; and U.S. Pat. No. 5,418,149. For example, buffer conditions can be as described above with respect to polynucleotide synthesis. In one embodiment, UDG (Epicentre Technologies, Madison Wis.) is added to a nucleic acid synthesis reaction mixture, and incubated at 37° C. for 20 minutes. In one embodiment, the reaction conditions are the same for the synthesis of a polynucleotide comprising a non-canonical nucleotide and the cleavage of a base portion of the non-canonical nucleotide. In another embodiment, different reaction conditions are used for these reactions. In some embodiments, a chelating regent (e.g. EDTA) is added before or concurrently with UNG in order to prevent a polymerase from extending the ends of the cleavage products.

The polynucleotide comprising an abasic site may be labeled using an agent capable of labeling an abasic site, and, in embodiments involving fragmentation, the phosphodiester backbone of the polynucleotide comprising an abasic site may be cleaved at the site of incorporation of the non-canonical nucleotide (i.e., the abasic site by an agent capable of cleaving the phosphodiester backbone at an abasic site, such that two or more fragments are produced. In embodiments involving fragmentation, labeling can occur before fragmentation, fragmentation can occur before labeling, or fragmentation and labeling can occur simultaneously.

Agents capable of labeling (e.g., generally or specifically labeling) an abasic site, whereby a polynucleotide (or polynucleotide fragment) comprising a labeled abasic site is generated, are provided herein. In some embodiments, the detectable moiety (label) is covalently or non-covalently associated with an abasic site. In some embodiments, the detectable moiety is directly or indirectly associated with an abasic site. In some embodiments, the detectable moiety (label) is directly or indirectly detectable. In some embodiments, the detectable signal is amplified. In some embodiments, the detectable moiety comprises an organic molecule such as a chromophore, a fluorophore, biotin or a derivative thereof. In other embodiments, the detectable moiety comprises a macromolecule such as a nucleic acid, an aptamer, a peptide, or a protein such as an enzyme or an antibody. In other embodiments, the detectable signal is fluorescent. In other embodiments, the detectable signal is enzymatically generated. In some embodiments, the label is selected from, fluorescein, rhodamine, a cyanine dye, an indocyanine dye, Cy3, Cy5, an Alexa Fluor dye, phycoerythrin, 5-(((2-(carbohydrazino)-methyl)thio)acetyl)aminofluorescein, aminooxyacetyl hydrazide ("FARP"), or N-(aminooxyacetyl)-N'-(D-biotinoyl)hydrazine, trifluoroacetic acid salt (ARP).

The cleavage of the input nucleic acid template comprising one or more abasic sites may further be provided by the use of enzymatic or chemical means or by the application of heat, or a combination thereof. For example the input nucleic acid template comprising one or more abasic sites may be treated with a nucleophile or a base. In some cases, the nucleophile is an amine such as a primary amine, a secondary amine, or a tertiary amine. For example, the abasic site may be treated with piperidine, morpholine, or a combination thereof. In some cases, hot piperidine (e.g., 1M at 90° C.) may be used to cleave the input nucleic acid template comprising one or more abasic sites. In some cases, morpholine (e.g., 3M at 37° C. or 65° C.) may be used to cleave the input nucleic acid template comprising one or more abasic sites. Alternatively, a polyamine may be used to cleave the input nucleic acid template comprising one or more abasic sites. Suitable polyamines include for example spermine, spermidine, 1,4-diaminobutane, lysine, the tripeptide K—W—K, N,N-dimethylethylenediamine (DMED), piperazine, 1,2-ethylenediamine, or any combination thereof. In some cases, the input nucleic acid template comprising one or more abasic sites may be treated with a reagent suitable for carrying out a beta elimination reaction, a delta elimination reaction, or a combination thereof. In some cases, the cleavage of input nucleic acid template comprising one or more abasic sites by chemical means may provide fragments of input nucleic acid template, which fragments comprise a blocked 3' end. In some cases, the blocked 3' end lacks a terminal hydroxyl. In other cases, the blocked 3' end is phosphorylated. In still other cases, cleavage of the input nucleic acid template comprising one or more abasic sites by chemical means may provide fragments of input nucleic acid template that are not blocked. In some cases, the methods of the present invention provide for the use of an enzyme or combination of enzymes and a polyamine such as DMED under mild conditions in a single reaction mixture which does not affect the canonical nucleotides and therefore may maintain the sequence integrity of the products of the method. Suitable mild conditions may include conditions at or near neutral pH. Other suitable conditions include pH of about 4.5 or higher, 5 or higher, 5.5 or higher, 6 or higher, 6.5 or higher, 7 or higher, 7.5 or higher, 8 or higher, 8.5 or higher, 9 or higher, 9.5 or higher, 10 or higher, or about 10.5 or higher. Still other suitable conditions include between about 4.5 and 10.5, between about 5 and 10.0, between about 5.5 and 9.5, between about 6 and 9, between about 6.5 and 8.5, between about 6.5 and 8.0, or between about 7 and 8.0. Suitable mild conditions also may include conditions at or near room temperature. Other suitable conditions include a temperature of about 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., or 70° C. or higher. Still other suitable conditions include between about 10° C. and about 70° C., between about 15° C. and about 65° C., between about 20° C. and about 60° C., between about 20° C. and about 55° C., between about 20° C. and about 50° C., between about 20° C. and about 45° C., between about 20° C. and about 40° C., between about 20° C. and about 35° C., or between about 20° C. and about 30° C. In some cases, the use of mild cleavage conditions may provide for less damage to the primer extension products produced by the methods of the present invention. In some cases, the fewer damaged bases, the more suitable the primer extension products may be for downstream analysis such as sequencing, or hybridization. In other cases, the use of mild cleavage conditions may increase final product yields, maintain sequence integrity, or render the methods of the present invention more suitable for automation.

In embodiments involving fragmentation, the backbone of the template polynucleotide comprising the abasic site is cleaved at the abasic site, whereby two or more fragments of the polynucleotide are generated. At least one of the fragments comprises an abasic site, as described herein. Agents that cleave the phosphodiester backbone of a polynucleotide at an abasic site are provided herein. In some embodiments, the agent is an AP endonuclease such as E. coli AP endonuclease IV. In other embodiments, the agent is N,N'-dimethylethylenediamine (termed "DMED"). In other embodiments, the agent is heat, basic condition, acidic conditions, or an alkylating agent. In still other embodiments, the agent that cleaves the phosphodiester backbone at an abasic site is the same agent that cleaves the base portion of a nucleotide to form an abasic site. For example, glycosidases of the present invention may comprise both a glycosidase and a lyase activity, whereby the glycosidase activity cleaves the base portion of a nucleotide (e.g., a non-canonical nucleotide) to form an abasic site and the lyase activity cleaves the phosphodiester backbone at the abasic site so formed. In some cases, the glycosidase comprises both a glycosidase activity and an AP endonuclease activity.

Depending on the agent employed for cleaving at the abasic site of the template polynucleotide, the backbone can be cleaved 5' to the abasic site (e.g., cleavage between the 5'-phosphate group of the abasic residue and the deoxyribose ring of the adjacent nucleotide, generating a free 3' hydroxyl group), such that an abasic site is located at the 5' end of the resulting fragment. In other embodiments, cleavage can also be 3' to the abasic site (e.g., cleavage between the deoxyribose ring and 3'-phosphate group of the abasic residue and the deoxyribose ring of the adjacent nucleotide, generating a free 5' phosphate group on the deoxyribose ring of the adjacent nucleotide), such that an abasic site is located at the 3' end of the resulting fragment. In still other embodiments, more complex forms of cleavage are possible, for example, cleavage such that cleavage of the phosphodiester backbone and cleavage of a portion of the abasic nucleotide results. Selection of the fragmentation agent thus permits control of the orientation of the abasic site within the polynucleotide fragment, for example, at the 3' end of the resulting fragment or the 5' end of the resulting fragment. Selection of reaction conditions also permits control of the degree, level or completeness of the fragmentation reactions. In some embodiments, reaction conditions can be selected such that the cleavage reaction is performed in the presence of a large excess of reagents and allowed to run to completion with minimal concern about cleavage of the primer extension products of the invention. By contrast, other methods known in the art, e.g., mechanical shearing, DNase cleavage, cannot distinguish between the template polynucleotide and the primer extension products. In other embodiments, reaction conditions are selected such that fragmentation is not complete (in the sense that the backbone at some abasic sites remains uncleaved (unfragmented)), such that polynucleotide fragments comprising more than one abasic site are generated. Such fragments comprise internal (nonfragmented) abasic sites.

Following generation of an abasic site by cleavage of the base portion of the non-canonical nucleotide if present in the polynucleotide, the backbone of the polynucleotide is cleaved at the site of incorporation of the non-canonical nucleotide (also termed the abasic site, following cleavage of the base portion of the non-canonical nucleotide) with an agent capable of effecting cleavage of the backbone at the abasic site. Cleavage at the backbone (also termed "fragmentation") results in at least two fragments (depending on the number of abasic sites present in the polynucleotide comprising an abasic site, and the extent of cleavage).

Suitable agents (for example, an enzyme, a chemical and/or reaction conditions such as heat) capable of cleavage of the backbone at an abasic site include: heat treatment and/or chemical treatment (including basic conditions, acidic conditions, alkylating conditions, or amine mediated cleavage of abasic sites, (see e.g., McHugh and Knowland, Nucl. Acids Res. (1995) 23(10):1664-1670; Bioorgan. Med. Chem (1991) 7:2351; Sugiyama, Chem. Res. Toxicol. (1994) 7: 673-83; Horn, Nucl. Acids. Res., (1988) 16:11559-71), and use of enzymes that catalyze cleavage of polynucleotides at abasic sites, for example AP endonucleases (also called "apurinic, apyrimidinic endonucleases") (e.g., E. coli Endonuclease IV, available from Epicentre Tech., Inc, Madison Wis.), E. coli endonuclease III or endonuclease IV, E. coli exonuclease III in the presence of calcium ions. See, e.g. Lindahl, PNAS (1974) 71(9):3649-3653; Jendrisak, U.S. Pat. No. 6,190,865 B1; Shida, Nucleic Acids Res. (1996) 24(22):4572-76; Srivastava, J. Biol Chem. (1998) 273(13): 21203-209; Carey, Biochem. (1999) 38:16553-60; Chem Res Toxicol (1994) 7:673-683. As used herein "agent" encompasses reaction conditions such as heat. In one embodiment, the AP endonuclease, E. coli endonuclease IV, is used to cleave the phosphodiester backbone at an abasic site. In another embodiment, cleavage is with an amine, such as N,N'-dimethylethylenediamine. See, e.g., McHugh and Knowland, supra.

Cleavage of the abasic site may occur between the nucleotide immediately 5' to the abasic residue and the abasic residue, or between the nucleotide immediately 3' to the abasic residue and the abasic residue (though, as explained herein, 5' or 3' cleavage of the phosphodiester backbone may or may not result in retention of the phosphate group 5' or 3' to the abasic site, respectively, depending on the fragmentation agent used). Cleavage can be 5' to the abasic site (such as endonuclease IV treatment which generally results in cleavage of the backbone at a location immediately 5' to the abasic site between the 5'-phosphate group of the abasic residue and the deoxyribose ring of the adjacent nucleotide, generating a free 3' hydroxyl group on the adjacent nucleotide), such that an abasic site is located at the 5' end of the resulting fragment. Cleavage can also be 3' to the abasic site (e.g., cleavage between the deoxyribose ring and 3'-phosphate group of the abasic residue and the deoxyribose ring of the adjacent nucleotide, generating a free 5' phosphate group on the deoxyribose ring of the adjacent nucleotide), such that an abasic site is located at the 3' end of the resulting fragment. Treatment under basic conditions or with amines (such as N,N'-dimethylethylenediamine) results in cleavage of the phosphodiester backbone immediately 3' to the abasic site. In addition, more complex forms of cleavage are also possible, for example, cleavage such that cleavage of the phosphodiester backbone and cleavage of (a portion of) the abasic nucleotide results. For example, under certain conditions, cleavage using chemical treatment and/or thermal treatment may comprise a β-elimination step which results in cleavage of a bond between the abasic site deoxyribose ring and its 3' phosphate, generating a reactive α,β-unsaturated aldehyde which can be labeled or can undergo further cleavage and cyclization reactions. See, e.g., Sugiyama, Chem. Res. Toxicol. (1994) 7: 673-83; Horn, Nucl. Acids. Res., (1988) 16:11559-71. It is understood that more than one method of cleavage can be used, including two or more different methods which result in multiple, different types of cleavage products (e.g., fragments comprising an abasic site at the 3' end, and fragments comprising an abasic site at the 5' end).

Cleavage of the backbone at an abasic site may be general, specific or selective (in the sense that the agent (such as an enzyme) capable of cleaving the backbone at an abasic site specifically or selectively cleaves the base portion of a particular non-canonical nucleotide), whereby greater than about 98%, about 95%, about 90%, about 85%, or about 80% of the cleavage is at an abasic site. However, extent of cleavage can be less. Thus, reference to specific cleavage is exemplary. General, specific or selective cleavage is desirable for control of the fragment size in the methods of generating labeled polynucleotide fragments of the invention. In some embodiments, reaction conditions can be selected such that the cleavage reaction is performed in the presence of a large excess of reagents and allowed to run to completion with minimal concern about excessive cleavage of the polynucleotide (i.e., while retaining a desired fragment size, which is determined by spacing of the incorporated non-canonical nucleotide, during the synthesis step, above). In other embodiments, extent of cleavage can be less, such that polynucleotide fragments are generated comprising an abasic site at an end and an abasic site(s) within or internal to the polynucleotide fragment (i.e., not at an end).

In embodiments involving cleavage of the phosphodiester backbone, appropriate reaction media and conditions for carrying out the cleavage of the phosphodiester backbone at an abasic site according to the methods of the invention are those that permit cleavage of the phosphodiester backbone at an abasic site. Such media and conditions are known to persons of skill in the art, and are described in various publications, such as Bioorgan. Med. Chem (1991) 7:2351; Sugiyama, Chem. Res. Toxicol. (1994) 7: 673-83; Horn, Nucl. Acids. Res., (1988) 16:11559-71; Lindahl, PNAS (1974) 71(9):3649-3653; Jendrisak, U.S. Pat. No. 6,190,865 B1; Shida, Nucleic Acids Res. (1996) 24(22):4572-76; Srivastava, J. Biol Chem. (1998) 273(13):21203-209; Carey, Biochem. (1999) 38:16553-60; Chem Res Toxicol (1994) 7:673-683.

In some cases, nucleic acids containing abasic sites are heated in a buffer solution containing an amine, for example, 25 mM Tris-HCl and 1-5 mM magnesium ions, for 10-30 minutes at 70° C. to 95° C. Alternatively, 1.0 M piperidine (a base) is added to polynucleotide comprising an abasic site which has been precipitated with ethanol and vacuum dried. The solution is then heated for 30 minutes at 90° C. and lyophilized to remove the piperidine. In another example, cleavage is effected by treatment with basic solution, e.g., 0.2 M sodium hydroxide at 37° C. for 15 minutes. See Nakamura (1998) Cancer Res. 58:222-225. In yet another example, incubation at 37° C. with 100 mM N,N'-dimethylethylenediamine acetate, pH 7.4 is used to cleave. See McHugh and Knowland, (1995) Nucl. Acids Res. 23(10) 1664-1670.

The cleavage of the input nucleic acid template comprising one or more abasic sites may also be performed by enzymatic means. For example an apyrimidinic endonuclease or an apurinic endonuclease (collectively known as AP endonucleases) may be used to cleave the input nucleic acid template at the one or more abasic sites. In some cases, the input nucleic acid template comprising one or more abasic sites may be cleaved with a class I, class II, class III, or class IV AP endonuclease or a combination thereof. In some cases, the cleavage of input nucleic acid template comprising one or more abasic sites by enzymatic means may provide fragments of input nucleic acid template, which fragments comprise a blocked 3' end. In some cases, the blocked 3' end lacks a terminal hydroxyl. In other cases, the blocked 3' end is phosphorylated. In still other cases, cleavage of the input nucleic acid template comprising one or more abasic sites by enzymatic means may provide fragments of input nucleic acid template that are not blocked.

In some cases, the cleavage may be performed by use of a glycosylase and a nucleophile, or a glycosylase and an amine, or a glycosylase and an AP endonuclease such as for example UDG and DMED or UDG and an AP endonuclease at the same time. Alternatively, the input nucleic acid template comprising one or more non-canonical nucleotides may first be treated with a glycosylase to produce one or more abasic sites, and then be treated with an AP endonuclease or cleaved by chemical means. In some cases, the hybridization, and extension reactions are performed first, and then the cleavage reaction is performed after sufficient time. In other cases, the hybridization and extension reactions are performed at the same time as the cleavage reactions. In still other cases, the hybridization and extension reactions are initiated and allowed to proceed for a set period of time (e.g., 1 minute, 2 minutes, 3 minutes, 5 minutes, 10 minutes, 15 minutes, 30 minutes, 1 hour, 2 hours, 3 hours etc.) and then the cleavage reaction is initiated. In some cases, initiation of the cleavage reaction may stop the extension reaction; in other cases, the cleavage reaction and the extension reaction may then proceed concurrently.

For example, *E. coli* AP endonuclease IV may be added to reaction conditions as described above. AP Endonuclease IV can be added at the same or different time as the agent (such as an enzyme) capable of cleaving the base portion of a non-canonical nucleotide. For example, AP Endonuclease IV can be added at the same time as UNG, or at different times. Alternatively, the template nucleic acid or a reaction mixture comprising template nucleic acid may be treated with UNG and an amine at the same time. A reaction mixture suitable for simultaneous UNG treatment and N,N'-dimethylethylenediamine treatment may include about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, or about 50 mM DMED. Alternatively, the use of an agent that comprises both glycosidase and lyase activity may be utilized in the reaction mixture to cleave the input nucleic acid template.

Cleavage of the input nucleic acid template by chemical means, enzymatic means, or a combination thereof may provide a mixture of double stranded products, single stranded products, and partial duplexes. In some cases, the cleaved products of the cleavage reaction may be removed by one or more methods of the present invention. In some cases, the cleaved products of the cleavage reaction may be removed by purification. For example, the cleaved products of the cleavage reaction may be removed by a size-dependent purification method, or an affinity based purification method. For example, the single stranded nucleic acids may be removed by an affinity hybridization step to capture probes. In some cases, the capture probes may be hybridized to a solid substrate. In other cases, the cleaved nucleic acid products of the cleavage reaction may be removed by an affinity capture step using a ligand with affinity to a label that has been incorporated into the cleaved products of the cleavage reaction. The label, or ligand, may be incorporated prior to cleavage (e.g. during synthesis of the template nucleic acid), during cleavage, or after the cleavage step. In some cases, the label may be incorporated at the abasic site. In other cases, the cleaved nucleic acid products of the cleavage reaction may be removed by a capture step using a reactive moiety (e.g., an amine or a hydrazine) such as an immobilized reactive moiety that reacts with a reactive $\alpha,\beta$-unsaturated aldehyde present at the abasic site of the cleaved nucleic acid product of the cleavage reaction. In some cases, the cleaved nucleic acid products of the cleavage reaction may be removed by electrophoresis or ultrafiltration.

In other cases, the single stranded products may be removed by enzymatic means. For example, a single stranded specific exonuclease or endonuclease can be used to cleave the single stranded DNA. A variety of suitable single stranded DNA specific exonucleases are suitable for the methods of the present invention such as for example exonuclease 1, and exonuclease 7. Similarly a variety of suitable single stranded DNA specific endonucleases are suitable for the methods of the present invention such as for example the single stranded DNA specific endonuclease is a S1 endonuclease or a mung bean nuclease. In some cases, any combination of single strand specific endonucleases or exonucleases known in the art such as those provided herein may be utilized to degrade or remove single stranded products, such as single stranded fragmentation products or single stranded primer extension products or a combination thereof.

In some cases, the products of the primer extension reaction generated in the methods of the present invention may be purified from the reaction mixture comprising fragmented target nucleic acid and primer extension products. For example, the primer extension step may include the use of nucleotides comprising a purification label such as for example biotin/avidin or any other suitable label (e.g. digoxin, fluorescein, an antigen, a ligand, a receptor, or any nucleotide labels provided herein). Primer extension products may therefore be understood to contain a member of the biotin/avidin ligand receptor pair or other purification label, whereas primers and template nucleic acid may not. A simple purification step may be performed to remove unincorporated nucleotides such as alcohol or polyethylene glycol precipitation, ion exchange purification, ultrafiltration, silica absorption, or reverse phase methods, and then the primer extension products may be recovered using an appropriate affinity matrix such as a matrix comprising biotin or a derivative thereof, avidin or a derivative thereof, streptavidin or a derivative thereof, an antibody or a derivative or fragment thereof, an antigen, a ligand, or a receptor in the form of particles, beads, a membrane or a column. Alternatively, the simple purification step to remove unincorporated nucleotides may be omitted or performed after the affinity purification step.

In some embodiments, the methods of the present invention further provide for the generation of one or more blunt ended double stranded products. In some embodiments the blunt ended double stranded products are produced from a template not containing any non-canonical nucleotides. In other embodiments the double stranded products are produced from a template containing one or more non-canonical nucleotides. In some cases, the extension step of the present invention directly provides blunt ended double stranded products. In other cases, the extension step of the present invention provides a mixture of blunt ended and non-blunt ended double stranded products. In still other cases, the extension step does not provide blunt ended double stranded products, or does not provide a substantial degree or amount of blunt ended double stranded products. In some cases, the non-blunt ended products of the primer extension reaction must be further treated by the methods of the present invention to produce blunt ended double stranded products, or to convert a substantial fraction of the non-blunt ended products to blunt ended products.

In some cases, the double stranded products generated by the method of the present invention may be blunt ended, when blunt end dsDNA is desirable for downstream analysis such as highly parallel sequencing, or other cloning or adaptor ligation applications, by the use of a single strand specific DNA exonuclease such as for example exonuclease 1, exonuclease 7 or a combination thereof to degrade overhanging single stranded ends of the double stranded products. Alternatively, the double stranded products may be blunt ended by the use of a single stranded specific DNA endonuclease for example but not limited to mung bean endonuclease or S1 endonuclease. Alternatively, the double stranded fragment products may be blunt ended by the use of a polymerase that comprises single stranded exonuclease activity such as for example T4 DNA polymerase, any other polymerase comprising single stranded exonuclease activity or a combination thereof to degrade the overhanging single stranded ends of the double stranded products. In some cases, the polymerase comprising single stranded exonuclease activity may be incubated in a reaction mixture that does or does not comprise one or more dNTPs. In other cases, a combination of single stranded nucleic acid specific exonucleases and one or more polymerases may be used to blunt end the double stranded products of the primer extension reaction. In still other cases, the products of the extension reaction may be made blunt ended by filling in the overhanging single stranded ends of the double stranded products. For example, the fragments may be incubated with a polymerase such as T4 DNA polymerase or Klenow polymerase or a combination thereof in the presence of one or more dNTPs to fill in the single stranded portions of the double stranded products. Alternatively, the double stranded products may be made blunt by a combination of a single stranded overhang degradation reaction using exonucleases and/or polymerases, and a fill-in reaction using one or more polymerases in the presence of one or more dNTPs.

In some embodiments, the methods of the present invention provide for generation of primer extension products comprising double stranded nucleic acids, single stranded nucleic acids, and nucleic acids comprising partial double stranded and partial single stranded portions, either from a template not comprising any non-canonical nucleotides or from a template nucleic acid comprising one or more non-canonical nucleotides; fragmentation of the template nucleic acid; optional purification of the primer extension products; and generation of double stranded products from the single stranded nucleic acid primer extension products and/or from the primer extension products comprising partial double stranded and partial single stranded portions. Methods for generation of double stranded products from partial double stranded products are provided herein including the methods for blunt ending double stranded primer extension products. Methods for generation of double stranded primer extension products from single stranded primer extension products include for example annealing one or more primers, such as any of the primers provided herein, to the single stranded primer extension product and extending the one or more annealed primers with a polymerase, such as any of the polymerases provided herein or a any suitable polymerase in a reaction mixture comprised of one or more dNTPs, including labeled dNTPs, canonical dNTPs, non-canonical dNTPs or a combination thereof. In some cases, the non-canonical nucleotides utilized in the reaction mixture for generating double stranded products from single stranded primer extension products or from partial double stranded products are different from at least one of the non-canonical nucleotides present in the template polynucleotide. Methods of generation of double stranded primer extension products from single stranded primer extension products may further include for example annealing two or more adjacent primers, such as any of the primers provided herein including random primers (e.g. pentamers, hexamers, heptamers, octamers, nonamers, decamers, undecamers, dodecamers, tridecamers etc.), to the single stranded primer extension product and ligating the adjacent primers. Methods for generating double stranded primer extension products from single stranded primer extension products may further include for example annealing one or more primers such as any of the primers provided herein including primers comprising random hybridizing portions (e.g. random pentamers, hexamers, heptamers, octamers, nonamers, decamers, undecamers, dodecamers, tridecamers etc.) to the single stranded primer extension product and extending the annealed primers. In some cases, the extension step may be performed using an enzyme (e.g., a DNA dependent DNA polymerase) comprising strand displacement activity.

In some embodiments, the methods of the present invention provide for attachment (e.g., ligation) of adaptor molecules to the double stranded DNA products of the primer extension reaction, or double stranded products generated from the single stranded or partially double stranded products of the primer extension reaction. The adaptor molecules may be ligated to double stranded DNA fragment molecules comprising single stranded overhangs, including but not limited to single, double, triple, quadruple, quintuple, sextuple, septuple, octuple, or more base overhangs, or to double stranded DNA fragment molecules comprising blunt ends. In some cases, the adaptor molecules are ligated to blunt end double stranded DNA fragment molecules which have been modified by 5' phosphorylation. In some cases, the adaptor molecules are ligated to blunt end double stranded DNA fragment molecules which have been modified by 5' phosphorylation followed by extension of the 3' end with one or more nucleotides. In some cases, the adaptor molecules are ligated to blunt end double stranded DNA fragment molecules which have been modified by 5' phosphorylation followed by extension of the 3' end with a single nucleotide (or 2, 3, 4, 5, 6, 7, 8, 9, 10, 11, 12, 13, 14, 15, 16, 17, 18, 19, 20 or more) such as for example adenine, guanine, cytosine, or thymine. In still other cases, adaptor molecules can be ligated to blunt end double stranded DNA fragment molecules which have been modified by extension of the 3' end with one or more nucleotides followed by 5' phosphorylation. In some cases, extension of the 3' end may be performed with a polymerase such as for example Klenow polymerase or any of the suitable polymerases provided herein, or by use of a terminal deoxynucleotide transferase, in the presence of one or more dNTPs in a suitable buffer containing magnesium. Phosphorylation of 5' ends of DNA fragment molecules may be performed for example with T4 polynucleotide kinase in a suitable buffer containing ATP and magnesium.

The adaptor molecules may comprise single or double stranded nucleic acids or a combination thereof. In some cases, the adaptor molecules comprise a one, two, three, four, five, six, seven, eight, nine, ten, eleven, twelve, thirteen, fourteen, fourteen, fifteen, sixteen, seventeen, eighteen, nineteen, twenty or longer base long single stranded overhang at their 5' ends. For example, the adaptor molecules may comprise a one base long thymine, adenine, cytosine, or guanine overhang at their 5' ends. Adaptor molecule compositions are provided herein.

In some embodiments, the methods of the present invention provide for ligation or attachment of adaptor molecules to the single stranded DNA products of the extension reaction. The adaptor molecules may comprise single stranded or double stranded nucleic acids or a combination thereof. The adaptor molecules may be ligated to the single stranded DNA products of the extension reaction using T4 RNA ligase which is capable of ligating two single stranded nucleic acids (RNA or DNA) together in the absence of a template. Alternatively, a single stranded DNA specific ligase such as for example CircLigase® may be utilized in the methods of the present invention.

In some embodiments, the methods of the present invention provide for contacting an input nucleic acid template comprising one or more non-canonical nucleotides with a reaction mixture. In some cases, the reaction mixture may comprise one or more oligonucleotide primers as provided herein. For example, the reaction mixture may comprise one or more oligonucleotide primers comprising random hybridizing portions. Additionally, the reaction mixture may comprise one or more oligonucleotide primers comprising random hybridizing portions and one or more oligonucleotide primers comprising a polyT sequence.

In some cases, the reaction mixture may comprise one or more polymerases as provided herein. For example, the reaction mixture may comprise one or more polymerases comprising strand displacement activity, such as for example, Klenow polymerase, exo-Klenow polymerase, 5'-3' exo-Klenow polymerase, Bst polymerase, Bst large fragment polymerase, Vent polymerase, Deep Vent (exo-) polymerase, 9° Nm polymerase, Therminator polymerase, Therminator II polymerase, MMulV Reverse Transcriptase, phi29 polymerase, or DyNAzyme EXT polymerase, or a combination thereof. In some cases, the reaction mixture may be configured to provide double stranded products in the presence of the input nucleic acid template, the one or more oligonucleotide primers, and the one or more polymerases comprising strand displacement activity. Enzymes for use in the compositions, methods and kits of the present invention may further include any enzyme having reverse transcriptase activity. Such enzymes include, but are not limited to, retroviral reverse transcriptase, retrotransposon reverse transcriptase, hepatitis B reverse transcriptase, cauliflower mosaic virus reverse transcriptase, bacterial reverse transcriptase, E. coli DNA polymerase and klenow fragment, Tth DNA polymerase, Taq DNA polymerase (Saiki, R. K., et al., Science 239:487-491 (1988); U.S. Pat. Nos. 4,889,818 and 4,965,188), Tne DNA polymerase (WO 96/10640), Tma DNA polymerase (U.S. Pat. No. 5,374,553), C. Therm DNA polymerase from *Carboxydothermus hydrogenoformans* (EP0921196A1, Roche, Pleasanton, Calif., Cat. No. 2016338), ThermoScript (Invitrogen, Carsbad, Calif. Cat. No. 11731-015) and mutants, fragments, variants or derivatives thereof. As will be understood by one of ordinary skill in the art, modified reverse transcriptases may be obtained by recombinant or genetic engineering techniques that are routine and well-known in the art. Mutant reverse transcriptases can, for example, be obtained by mutating the gene or genes encoding the reverse transcriptase of interest by site-directed or random mutagenesis. Such mutations may include point mutations, deletion mutations and insertional mutations. Preferably, one or more point mutations (e.g., substitution of one or more amino acids with one or more different amino acids) are used to construct mutant reverse transcriptases of the invention. Fragments of reverse transcriptases may be obtained by deletion mutation by recombinant techniques that are routine and well-known in the art, or by enzymatic digestion of the reverse transcriptase(s) of interest using any of a number of well-known proteolytic enzymes. Mutant DNA polymerase containing reverse transcriptase activity can also be used as described in U.S. patent application Ser. No. 10/435,766, incorporated herein by reference.

In some cases, the reaction mixture may comprise one or more agents capable of cleaving the base portion of a non-canonical nucleotide to generate an abasic site. In some cases, the reaction mixture may contain the one or more agents capable of cleaving the base portion of a non-canonical nucleotide to generate an abasic site at the initiation of the extension reaction. In some cases, the reaction mixture may be supplemented with the one or more agents capable of cleaving the base portion of a non-canonical nucleotide to generate an abasic site after a suitable period of time (e.g., about 1, 2, 3, 4, 5, 10, 15, 20, 25, 30, 45, 60, 90, 120, 180, 240, 300, 400, 500, 600 minutes) has passed for the generation of primer extension products. Suitable agents capable of cleaving the base portion of a non-canonical nucleotide to generate an abasic site include but are not limited to UDG and MPG.

In some cases, the reaction mixture may comprise one or more agents capable of fragmenting a phosphodiester backbone at an abasic site to fragment the input nucleic acid template. In some cases, the reaction mixture may contain the one or more agents capable of fragmenting a phosphodiester backbone at an abasic site to fragment the input nucleic acid template at the initiation of the extension reaction. In some cases, the reaction mixture may be supplemented with the one or more agents capable of fragmenting a phosphodiester backbone at an abasic site to fragment the input nucleic acid template after a suitable period of time (e.g., about 1, 2, 3, 4, 5, 10, 15, 20, 25, 30, 45, 60, 90, 120, 180, 240, 300, 400, 500, 600 minutes) has passed for the generation of primer extension products. Suitable agents capable of fragmenting a phosphodiester backbone at an abasic site to fragment the input nucleic acid template include but are not limited to an amine, a primary amine, a secondary amine, a polyamine as provided herein, a nucleophile, a base (e.g. NaOH), piperidine, hot piperidine, and one or more AP endonucleases.

The methods of the present invention provide for downstream analysis of the primer extension products generated in the methods of the present invention. Said downstream analysis includes but is not limited to e.g. pyrosequencing, sequencing by synthesis, sequencing by hybridization, single molecule sequencing, nanopore sequencing, and sequencing by ligation, high density PCR, microarray hybridization, SAGE, digital PCR, and massively parallel Q-PCR; subtractive hybridization; differential amplification; comparative genomic hybridization, preparation of libraries (including cDNA and differential expression libraries); preparation of an immobilized nucleic acid (which can be a nucleic acid immobilized on a microarray), and characterizing amplified nucleic acid products generated by the methods of the invention, or a combination thereof.

Applications on Single Cells

Single cell sequencing and gene expression profiling is provided for a variety of suitable methods known in the art, such as disease diagnostic or prognostic applications, as well as a research tool, for example to identify novel drug targets. Diseases of interest include, without limitation, immune-mediated dysfunction, cancer, and the like. In the methods of the invention, a heterogeneous cell mixture, e.g. a tumor needle biopsy, inflammatory lesion biopsy, synovial fluid, spinal tap, etc., is divided randomly or in a certain order into spatially separated single cells, e.g. into a multiwell plate, microarray, microfluidic device, or slide. Cells are then lysed, and the contents amplified and individually analyzed for sequencing or expression of genes of interest. The cells thus analyzed can be classified according to the genetic signatures of individual cells. Such classification allows an accurate assessment of the cellular composition of a test sample, which assessment may find use, for example, in determining the identity and number of cancer stem cells in a tumor; in determining the identity and number of immune-associated cells such as the number and specificity of T cells, dendritic cells, B cells and the like.

In some embodiments, the cell sample to be analyzed is a primary sample, which may be freshly isolated, frozen, etc. However, cells to be analyzed can be cultured cells. Usually the sample is a heterogeneous mixture of cells, comprising a plurality of distinct cell types, distinct populations, or distinct subpopulations, for example 2, 3, 4, 5, 6, 7, 8, 9, 10, 11, 12, 13, 14, 15, 16, 17, 18, 19, 20 or more cell types, populations, or subpopulations. In some embodiments the sample is a cancer sample from a solid tumor, leukemia, lymphoma, etc., which may be a biopsy, e.g. a needle biopsy, etc., a blood sample for disseminated tumors and leukemias, and the like. Samples may be obtained prior to diagnosis, may be obtained through a course of treatment, and the like.

For isolation of cells from tissue, an appropriate solution can be used for dispersion or suspension. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc. The separated cells can be collected in any appropriate medium that maintains the viability of the cells, usually having a cushion of serum at the bottom of the collection tube. Various media are commercially available and may be used according to the nature of the cells, including dMEM, HBSS, dPBS, RPMI, Iscove's medium, etc., frequently supplemented with fetal calf serum.

Systems such as Beckman MoFlo cell sorter, Becton Dickenson Influx, or Bio-Rad S3 can be used to sort heterogeneous mixtures of cells based on surface markers, size, etc. into distinct populations.

In some embodiments, cells in a sample are separated on a microarray. For example, a highly integrated live-cell microarray system may utilize microwells each of which is just large enough to fit a single cell (see Tokimitsu et al. (2007) Cytometry Part A 71k 1003:1010; and Yamamura et al. (2005) Analytical Chemistry 77:8050; each herein specifically incorporated by reference). Prior enrichment of cells of interest—such as by FACS or other sorting—is optional and in some embodiments, cells from a sample are divided into discrete locations without any prior sorting or enrichment. For example, cells from a sample (e.g., blood sample, biopsy, solid tumor) can be individually isolated into distinct positions. Typically, for solid tissue samples, the samples are mechanically, chemically, and/or enzymatically separated (e.g., by treatment with trypsin or sonication). Cells from a sample can be placed into any cell sorting device (e.g., a microfluidic cell sorter) such that individual cells are isolated, such as at an addressable position on a planar surface. Planar surfaces can have indentations, barriers or other features ensuring isolation of individual cells. Isolated cells can then be analyzed according to the methods herein. Preferably, cells are separated into distinct positions wherein each position contains 1 or 0 cells.

Cells are optionally sorted, e.g. by flow cytometry, prior to the separation. For example, FACS sorting or size-differential sorting, can be used to increase the initial concentration of the cells of interest by at least 1,000, 10,000, 100,000, or more fold, according to one or more markers present on the cell surface. Such cells are optionally sorted according to the presence and/or absence of cell surface markers particularly markers of a population or subpopulation of interest.

Cell Sorters

Where the cells are isolated into distinct positions for analysis, the cells may be sorted with a microfluidic sorter, by flow cytometry, microscopy, etc. A microfabricated fluorescence-activated cell sorter is described by Fu et al. (1999) Nature Biotechnology 17: 1109 and Fu et al. (2002) Anal. Chem. 74:2451-2457, each herein specifically incorporated by reference. A sample can be sorted with an integrated microfabricated cell sorter using multilayer soft lithography. This integrated cell sorter may incorporate various microfluidic functionalities, including peristaltic pumps, dampers, switch valves, and input and output wells, to perform cell sorting in a coordinated and automated fashion. The active volume of an actuated valve on this integrated cell sorter can be as small as 1 pL, and the volume of optical interrogation as small as 100 fL. Compared with conventional FACS machines, the microfluidic FACS provides higher sensitivity, no cross-contamination, and lower cost.

Individual cells can be isolated into distinct positions (e.g., a 96-well plate or a microarray address) for further analysis and/or manipulation. For example, a cell population containing a desired cell type, such as, hematopoietic stem cells (HSCs) is sorted by FACS analysis utilizing antibodies capable of distinguishing HSCs from mature cells. The cells are sorted into 96-well plates, lysed by appropriate methods and the lysates are analyzed by qPCR, microarray analysis, and/or sequencing.

Devices for single cell isolation include a microfluidic cell sorter, which isolates live cells from cellular debris and sorts cells from a single cell suspension. Microfluidic devices can be used in combination with fluorescent signals (e.g., labeled antibodies to markers for a target population or subpopulation) from 1, 2, 3, 4, 5 or more different surface markers, and places them in individual bins for subsequent genetic studies. Other upstream steps such as digesting the tumor or cell culture to obtain a cell suspension and staining the cells with fluorescent surface markers may be incorporated in this system. The number of cells to be analyzed depends on the heterogeneity of the sample, and the expected frequency of cells of interest in the sample. Usually at least about $10^2$ cells are analyzed, at least about $10^3$, at least $5\times10^3$, at least about $10^4$, at least about $10^5$, at least about $10^6$, at least about $10^7$, at least about $10^8$, at least about $10^9$, at least about $10^{10}$, at least about $10^{11}$, at least about $10^{12}$, at least about $10^{13}$, at least about $10^{14}$, at least about $10^{15}$, or more cells are analyzed.

In some instances, a single cell analysis device (SCAD) is modular and can perform multiple steps, such as digestion of the tissue, separation of live cells from the debris, staining, or sorting in an integrated, fully automated fashion.

Sorted cells can be individually lysed to perform analysis of genetic (RNA, DNA) and/or protein composition of the cells. mRNA can be captured on a column of oligo-dT beads, reverse transcribed on beads, processed off chip, transferred to a macroscopic well, etc. Optionally, DNA or RNA is preamplified prior to analysis. Preamplification can be of an entire genome or transcriptome, or a portion thereof (e.g., genes/transcripts of interest). A polynucleotide sample can be transferred to a chip for analysis (e.g., by qRT-PCR) and determination of an expression profile.

A nucleic acid sample includes a plurality or population of distinct nucleic acids that can include the expression information of the phenotype determinative genes of interest of the individual cell. A nucleic acid sample can include RNA or DNA nucleic acids, e.g., mRNA, cRNA, cDNA, etc. Expression profiles can be generated by any convenient means for determining differential gene expression between two samples, e.g. quantitative hybridization of mRNA, labeled mRNA, amplified mRNA, cRNA, etc., quantitative PCR, and the like. A subject or patient sample, e.g., cells or collections thereof, e.g., tissues, is assayed. Samples are collected by any convenient method, as known in the art.

The sample can be prepared in a number of different ways, as is known in the art, e.g., by mRNA isolation from a single cell, where the isolated mRNA is used as is, amplified, employed to prepare cDNA, cRNA, etc., as is known in the differential expression art (for example, see Marcus, et al., Anal. Chem. (2006); 78(9): 3084-89). The sample can be prepared from any tissue (e.g., a lesion, or tumor tissue) harvested from a subject. Analysis of the samples can be used for any purpose (e.g., diagnosis, prognosis, classification, tracking and/or developing therapy). Cells may be cultured prior to analysis.

The expression profile may be generated from the initial nucleic acid sample using any conventional protocol. While a variety of different manners of generating expression profiles are known, such as those employed in the field of differential gene expression analysis, one representative and convenient type of protocol for generating expression profiles is quantitative PCR (QPCR, or QT-PCR). Any available methodology for performing QPCR can be utilized, for example, as described in Valera, et al., /.Neurooncol. (2007) 85(1):1-10.

Sorting of Cells

Cells with selected properties, for example cells with selected surface proteins, cells with a disrupted cell membrane, cells infected with a pathogen, dying cells or dead cells can be detected in a sample by a variety of techniques well known in the art, including cell sorting, especially fluorescence-activated cell sorting (FACS), by using an affinity reagent bound to a substrate (e.g., a plastic surface, as in panning), or by using an affinity reagent bound to a solid phase particle which can be isolated on the basis of the properties of the beads (e.g., colored latex beads or magnetic particles). Naturally, the procedure used to detect the cells will depend upon how the cells have been labelled. In one example, any detectable substance which has the appropriate characteristics for the cell sorter may be used (e.g., in the case of a fluorescent dye, a dye which can be excited by the sorter's light source, and an emission spectra which can be detected by the cell sorter's detectors). In flow cytometry, a beam of laser light is projected through a liquid stream that contains cells, or other particles, which when struck by the focussed light give out signals which are picked up by detectors. These signals are then converted for computer storage and data analysis, and can provide information about various cellular properties. Cells labelled with a suitable dye are excited by the laser beam, and emit light at characteristic wavelengths. This emitted light is picked up by detectors, and these analogue signals are converted to digital signals, allowing for their storage, analysis and display.

Many larger flow cytometers are also "cell sorters", such as fluorescence-activated cell sorters (FACS), and are instruments which have the ability to selectively deposit cells from particular populations into tubes, or other collection vessels. In a particularly preferred embodiment, the cells are isolated using FACS. This procedure is well known in the art and described by, for example, Melamed et al., Flow Cytometry and Sorting, Wiley-Liss, Inc., (1990); Shapiro, Practical Flow Cytometry, 4th Edition, Wiley-Liss, Inc., (2003); and Robinson et al., Handbook of Flow Cytometry Methods, Wiley-Liss, Inc. (1993).

In order to sort cells, the instruments electronics interprets the signals collected for each cell as it is interrogated by the laser beam and compares the signal with sorting criteria set on the computer. If the cell meets the required criteria, an electrical charge is applied to the liquid stream which is being accurately broken into droplets containing the cells. This charge is applied to the stream at the precise moment the cell of interest is about to break off from the stream, then removed when the charged droplet has broken from the stream. As the droplets fall, they pass between two metal plates, which are strongly positively or negatively charged. Charged droplets get drawn towards the metal plate of the opposite polarity, and deposited in the collection vessel, or onto a microscope slide, for further examination. The cells can automatically be deposited in collection vessels as single cells or as a plurality of cells, e.g. using a laser, e.g. an argon laser (488 nm) and for example with a Flow Cytometer fitted with an Autoclone unit (Coulter EPICS Altra, Beckman-Coulter, Miami, Fla., USA). Other examples of suitable FACS machines/useful for the methods of the invention include, but are not limited to, MoFlo™ Highspeed cell sorter (Dako-Cytomation ltd), FACS Aria™ (Becton Dickinson), FACS Diva (Becton Dickinson), ALTRA™ Hyper sort (Beckman Coulter) and Cy Flow™ sorting system (Partec GmbH).

The enrichment or sorting of desired cells and/or precursors thereof from a sample may be accomplished using solid-phase particles. Any particle with the desired properties may be utilized. For example, large particles (e.g., greater than about 90-100 µm in diameter) may be used to facilitate sedimentation. In some cases, the particles are "magnetic particles" (i.e., particles which can be collected using a magnetic field). Labeled cells may be retained in a column (held by the magnetic field), whilst unlabelled cells pass straight through and are eluted at the other end. Magnetic particles are now commonly available from a variety of manufacturers including Dynal Biotech (Oslo, Norway) and Milteni Biotech GmbH (Germany). An example of magnetic cell sorting (MACS) is provided by Al-Mufti et al. (1999).

Laser-capture microdissection can also be used to selectively enrich labelled dendritic cells or precursors thereof on a slide using methods of the invention. Methods of using laser-capture microdissection are known in the art (see, for example, U.S. 20030227611 and Bauer et al, 2002).

Target Polynucleotides

In various embodiments of the invention, nucleic acid are used as substrates for further manipulation. The input nucleic acid can be DNA, or complex DNA, for example genomic DNA. The input DNA may also be cDNA. The cDNA can be generated from RNA, e.g., mRNA. The input DNA can be of a specific species, for example, human, grape, rat, mouse, other animals, plants, bacteria, algae, viruses, and the like. The input nucleic acid also can be from a mixture of genomes of different species such as host-pathogen, bacterial populations and the like. The input DNA can be cDNA made from a mixture of genomes of different species. Alternatively, the input nucleic acid can be from a synthetic source. The input DNA can be mitochondrial DNA or chloroplast DNA. The input DNA can also comprise cDNA generated from one or more of cytoplasmic, mitochondrial, or chloroplast mRNA, rRNA, or tRNA The input DNA can be cell-free DNA. The cell-free DNA can be obtained from, e.g., a serum or plasma sample. The input DNA can comprise one or more chromosomes. For example, if the input DNA is from a human, the DNA can comprise one or more of chromosome 1, 2, 3, 4, 5, 6, 7, 8, 9, 10, 11, 12, 13, 14, 15, 16, 17, 18, 19, 20, 21, 22, X, or Y. The DNA can be from a linear or circular genome. The DNA can be plasmid DNA, cosmid DNA, bacterial artificial chromosome (BAC), or yeast artificial chromosome (YAC). The input DNA can be from more than one individual or organism. The input DNA can be double stranded or single stranded. The input DNA can be part of chromatin. The input DNA can be associated with histones. The methods described herein can be applied to high molecular weight DNA, such as is isolated from tissues or cell culture, for example, as well as highly degraded DNA, such as cell-free DNA from blood and urine and/or DNA extracted from formalin-fixed, paraffin-embedded tissues, for example.

The different samples from which the target polynucleotides are derived can comprise multiple samples from the same individual, samples from different individuals, or combinations thereof. In some embodiments, a sample comprises a plurality of polynucleotides from a single individual. In some embodiments, a sample comprises a plurality of polynucleotides from two or more individuals. An individual is any organism or portion thereof from which target polynucleotides can be derived, non-limiting examples of which include plants, animals, fungi, protists, monerans, viruses, mitochondria, and chloroplasts. Sample polynucleotides can be isolated from a subject, such as a cell sample, tissue sample, or organ sample derived therefrom, including, for example, cultured cell lines, biopsy, blood sample, or fluid sample containing a cell. The subject may be an animal, including but not limited to, an animal such as a cow, a pig, a mouse, a rat, a chicken, a cat, a dog, etc., and is usually a mammal, such as a human. Samples can also be artificially derived, such as by chemical synthesis. In some embodiments, the samples comprise DNA. In some embodiments, the samples comprise genomic DNA. In some embodiments, the samples comprise mitochondrial DNA, chloroplast DNA, plasmid DNA, bacterial artificial chromosomes, yeast artificial chromosomes, oligonucleotide tags, or combinations thereof. In some embodiments, the samples comprise DNA generated by primer extension reactions using any suitable combination of primers and a DNA polymerase, including but not limited to polymerase chain reaction (PCR), reverse transcription, and combinations thereof. Where the template for the primer extension reaction is RNA, the product of reverse transcription is referred to as complementary DNA (cDNA). Primers useful in primer extension reactions can comprise sequences specific to one or more targets, random sequences, partially random sequences, and combinations thereof. Reaction conditions suitable for primer extension reactions are known in the art. In general, sample polynucleotides comprise any polynucleotide present in a sample, which may or may not include target polynucleotides.

Methods for the extraction and purification of nucleic acids are well known in the art. For example, nucleic acids can be purified by organic extraction with phenol, phenol/chloroform/isoamyl alcohol, or similar formulations, including TRIzol and TriReagent. Other non-limiting examples of extraction techniques include: (1) organic extraction followed by ethanol precipitation, e.g., using a phenol/chloroform organic reagent (Ausubel et al., 1993), with or without the use of an automated nucleic acid extractor, e.g., the Model 341 DNA Extractor available from Applied Biosystems (Foster City, Calif.); (2) stationary phase adsorption methods (U.S. Pat. No. 5,234,809; Walsh et al., 1991); and (3) salt-induced nucleic acid precipitation methods (Miller et al., (1988), such precipitation methods being typically referred to as "salting-out" methods. Another example of nucleic acid isolation and/or purification includes the use of magnetic particles to which nucleic acids can specifically or non-specifically bind, followed by isolation of the beads using a magnet, and washing and eluting the nucleic acids from the beads (see e.g. U.S. Pat. No. 5,705,628). In some embodiments, the above isolation methods may be preceded by an enzyme digestion step to help eliminate unwanted protein from the sample, e.g., digestion with proteinase K, or other like proteases. See, e.g., U.S. Pat. No. 7,001,724. If desired, RNase inhibitors may be added to the lysis buffer. For certain cell or sample types, it may be desirable to add a protein denaturation/digestion step to the protocol. Purification methods may be directed to isolate DNA, RNA, or both. When both DNA and RNA are isolated together during or subsequent to an extraction procedure, further steps may be employed to purify one or both separately from the other. Sub-fractions of extracted nucleic acids can also be generated, for example, purification by size, sequence, or other physical or chemical characteristic. In addition to an initial nucleic isolation step, purification of nucleic acids can be performed after any step in the methods of the invention, such as to remove excess or unwanted reagents, reactants, or products.

Single Cells Suitable for Analysis

Samples containing nucleic acids or single cells can be obtained from biological sources and prepared using conventional methods known in the art. In particular, DNA or RNA useful in the methods described herein can be extracted and/or amplified from any source, including bacteria, protozoa, fungi, viruses, organelles, as well higher organisms such as plants or animals, e.g., mammals, and particularly humans. Suitable nucleic acids can also be obtained from an environmental source (e.g., pond water), from man-made products (e.g., food), from forensic samples, and the like. Nucleic acids can be extracted or amplified from cells, bodily fluids (e.g., blood, a blood fraction, urine, etc.), or tissue samples by any of a variety of standard techniques. Cells may either be cultured or from primary isolates such as clinical samples. Illustrative samples include samples of plasma, serum, spinal fluid, lymph fluid, peritoneal fluid, pleural fluid, oral fluid, and external sections of the skin; samples from the respiratory, intestinal, genital, and urinary tracts; samples of tears, saliva, blood cells, stem cells, or tumors. For example, samples of fetal DNA can be obtained from an embryo (e.g., from one or a few embryonic or fetal cells) or from maternal blood. Samples can be obtained from live or dead organisms or from in vitro cultures. Illustrative samples can include single cells, paraffin-embedded tissue samples, and needle biopsies. Nucleic acids useful in the methods described herein can also be derived from one or more nucleic acid libraries, including cDNA, cosmid, YAC, BAC, P1, PAC libraries, and the like.

Samples may reflect particular states, e.g., cell proliferation, cell differentiation, cell death, disease, exposure to stimuli, and/or stages, e.g., stages of development.

In particular embodiments, the methods described herein can carried out on a single cell from a preimplantation embryo, a stem cell, a suspected cancer cell, a cell from a pathogenic organism, and/or a cell obtained from a crime scene. For example, a human blastomere (e.g., from an eight-cell stage embryo or later) can be analyzed to determine whether the genome includes one or more genetic defects.

Nucleic acids of interest can be isolated using methods well known in the art, with the choice of a specific method depending on the source, the nature of nucleic acid, and similar factors. The sample nucleic acids need not be in pure form, but are typically sufficiently pure to allow the amplification steps of the methods described herein to be performed. Where the target nucleic acids are mRNA, the RNA can be reversed transcribed into cDNA by standard methods known in the art and as described in Sambrook, J., Fritsch, E. F., and Maniatis, T., Molecular Cloning: A Laboratory Manual. Cold Spring Harbor Laboratory Press, NY, Vol. 1, 2, 3 (1989), for example. The cDNA can then be analyzed according to the methods described herein.

In certain embodiments, a single cell can be added directly to a suitable WGA reaction mixture and WGA carried out. In other embodiments, the RNA of a single cell can be converted to DNA (e.g., cDNA) or the RNA directly amplified.

Fragmentation Methods

In some embodiments, sample polynucleotides are fragmented into a population of fragmented insert DNA molecules of one or more specific size range(s). In some embodiments, fragments are generated from at least about 1, 10, 100, 1000, 10000, 100000, 300000, 500000, or more genome-equivalents of starting DNA. Fragmentation may be accomplished by methods known in the art, including chemical, enzymatic, and mechanical fragmentation. In some embodiments, the fragments have an average length from about 10 to about 10,000 nucleotides. In some embodiments, the fragments have an average length from about 50 to about 2,000 nucleotides. In some embodiments, the fragments have an average length from about 100-2,500, 10-1,000, 10-800, 10-500, 50-500, 50-250, or 50-150 nucleotides. In some embodiments, the fragments have an average length less than 500 nucleotides, such as less than 400 nucleotides, less than 300 nucleotides, less than 200 nucleotides, or less than 150 nucleotides. In some embodiments, the fragmentation is accomplished mechanically comprising subjecting sample polynucleotides to acoustic sonication. In some embodiments, the fragmentation comprises treating the sample polynucleotides with one or more enzymes under conditions suitable for the one or more enzymes to generate double-stranded nucleic acid breaks. Examples of enzymes useful in the generation of polynucleotide fragments include sequence specific and non-sequence specific nucleases. Non-limiting examples of nucleases include DNase I, Fragmentase, restriction endonucleases, variants thereof, and combinations thereof. For example, digestion with DNase I can induce random double-stranded breaks in DNA in the absence of Mg++ and in the presence of Mn++. In some embodiments, fragmentation comprises treating the sample polynucleotides with one or more restriction endonucleases. Fragmentation can produce fragments having 5' overhangs, 3' overhangs, blunt ends, or a combination thereof. In some embodiments, such as when fragmentation comprises the use of one or more restriction endonucleases, cleavage of sample polynucleotides leaves overhangs having a predictable sequence. In some embodiments, the method includes the step of size selecting the fragments via standard methods such as column purification or isolation from an agarose gel. Combination of fragmentation methods can be utilized, such as a combination enzymatic and chemical methods. In a particular example, an abasic site can be generated, e.g. using a glycosylase (Uracil-DNA glycosylase, Thymine-DNA glycosylase etc.), and the abasic site can be cleaved using a chemical method, such as by contacting the abasic site with dimethylethylenediamine (DMED).

In some embodiments, the 5' and/or 3' end nucleotide sequences of fragmented DNA are not modified prior to ligation with one or more adaptor oligonucleotides. For example, fragmentation by a restriction endonuclease can be used to leave a predictable overhang, followed by ligation with one or more adaptor oligonucleotides comprising an overhang complementary to the predictable overhang on a DNA fragment. In another example, cleavage by an enzyme that leaves a predictable blunt end can be followed by ligation of blunt-ended DNA fragments to adaptor oligonucleotides comprising a blunt end. In some embodiments, the fragmented DNA molecules are blunt-end polished (or "end repaired") to produce DNA fragments having blunt ends, prior to being joined to adaptors. The blunt-end polishing step may be accomplished by incubation with a suitable enzyme, such as a DNA polymerase that has both 3' to 5' exonuclease activity and 5' to 3' polymerase activity, for example T4 polymerase. In some embodiments, end repair is followed by an addition of 1, 2, 3, 4, 5, 6, 7, 8, 9, 10, 11, 12, 13, 14, 15, 16, 17, 18, 19, 20 or more nucleotides, such as one or more adenine, one or more thymine, one or more guanine, or one or more cytosine, to produce an overhang.

DNA fragments having an overhang can be joined to one or more adaptor oligonucleotides having a complementary overhang, such as in a ligation reaction. For example, a single adenine can be added to the 3' ends of end repaired DNA fragments using a template independent polymerase, followed by ligation to one or more adaptors each having a thymine at a 3' end. In some embodiments, adaptor oligonucleotides can be joined to blunt end double-stranded DNA fragment molecules which have been modified by extension of the 3' end with one or more nucleotides followed by 5' phosphorylation. In some cases, extension of the 3' end may be performed with a polymerase such as for example Klenow polymerase or any of the suitable polymerases provided herein, or by use of a terminal deoxynucleotide transferase, in the presence of one or more dNTPs in a suitable buffer containing magnesium. In some embodiments, target polynucleotides having blunt ends are joined to one or more adaptors comprising a blunt end. Phosphorylation of 5' ends of DNA fragment molecules may be performed for example with T4 polynucleotide kinase in a suitable buffer containing ATP and magnesium. The fragmented DNA molecules may optionally be treated to dephosphorylate 5' ends or 3' ends, for example, by using enzymes known in the art, such as phosphatases.

In some embodiments, each of the plurality of independent samples comprises at least about 1 pg, 10 pg, 100 pg, 1 ng, 10 ng, 20 ng, 30 ng, 40 ng, 50 ng, 75 ng, 100 ng, 150 ng, 200 ng, 250 ng, 300 ng, 400 ng, 500 ng, 1 µg, 1.5 µg, 2 µg, or more of nucleic acid material. In some embodiments, each of the plurality of independent samples comprises less than about 1 pg, 10 pg, 100 pg, 1 ng, 10 ng, 20 ng, 30 ng, 40 ng, 50 ng, 75 ng, 100 ng, 150 ng, 200 ng, 250 ng, 300 ng, 400 ng, 500 ng, 1 µg, 1.5 µg, 2 µg, or more of nucleic acid.

In some embodiments each of the individual or plurality of samples comprises a single polynucleotide target or a single genome.

In another aspect, the invention provides compositions that can be used in the above described methods. Compositions of the invention can comprise any one or more of the elements described herein. In one embodiment, the composition comprises a plurality of target polynucleotides, each target polynucleotide comprising one or more barcode sequences selected from a plurality of barcode sequences, wherein said target polynucleotides are from two or more different samples, and further wherein the sample from which each of said polynucleotides is derived can be identified in a combined sequencing reaction with an accuracy of at least 95% based on a single barcode contained in the sequence of said target polynucleotide. In some embodiments, the composition comprises a plurality of first adaptor/primer oligonucleotides, wherein each of said first adaptor/primer oligonucleotides comprises at least one of a plurality of barcode sequences, wherein each barcode sequence of the plurality of barcode sequences differs from every other barcode sequence in said plurality of barcode sequences at least three nucleotide positions.

Methods of Amplification

The methods, compositions and kits described herein can be useful to generate amplification-ready products for downstream applications such as massively parallel sequencing or hybridization platforms. Methods of amplification are well known in the art. In some embodiments, the amplification is exponential, e.g. in the enzymatic amplification of specific double stranded sequences of DNA by a polymerase chain reaction (PCR). In other embodiments the amplification method is linear. In other embodiments the amplification method is isothermal.

Thus, it is understood that the methods, compositions and kits described herein can be useful to generate amplification-ready products directly from genomic DNA or whole or partial transcriptome RNA for downstream applications such as massively parallel sequencing (Next Generation Sequencing methods), multiplexed quantification of large sets of sequence regions of interest, such as by high density qPCR arrays and other highly parallel quantification platforms (selective massively parallel target pre-amplification), as well as generation of libraries with enriched population of sequence regions of interest. The methods described herein can be used to generate a collection of at least 25, 50, 75, 100, 500, 1000, 2500, 5000, 10,000, 25,000, 50,000, 100,000, 500,000, or 1,000,000 amplification-ready target sequence regions of interest directly from a sample of complex DNA using a plurality of oligonucleotides.

Methods of nucleic acid amplification are well known in the art. In some embodiments, the amplification method is isothermal. In other embodiments the amplification method is linear. In other embodiments the amplification is exponential.

Amplification

In some embodiments, amplification methods can be solid-phase amplification, polony amplification, colony amplification, emulsion PCR, bead RCA, surface RCA, surface SDA, etc., as will be recognized by one of skill in the art. In some embodiments, amplification methods that results in amplification of free DNA molecules in solution or tethered to a suitable matrix by only one end of the DNA molecule can be used. Methods that rely on bridge PCR, where both PCR primers are attached to a surface (see, e.g., WO 2000/018957 and Adessi et al., Nucleic Acids Research (2000): 28(20): E87) can be used. In some cases the methods of the invention can create a "polymerase colony technology", or "polony", referring to a multiplex amplification that maintains spatial clustering of identical amplicons (see Harvard Molecular Technology Group and Lipper Center for Computational Genetics website). These include, for example, in situ polonies (Mitra and Church, Nucleic Acid Research 27, e34, Dec. 15, 1999), in situ rolling circle amplification (RCA) (Lizardi et al., Nature Genetics 19, 225, July 1998), bridge PCR (U.S. Pat. No. 5,641,658), picotiter PCR (Leamon et al., Electrophoresis 24, 3769, November 2003), and emulsion PCR (Dressman et al., PNAS 100, 8817, Jul. 22, 2003).

The methods of the present invention may further include a step of hybridizing one or more oligonucleotide primers to an input nucleic acid template. The template can optionally comprise one or more non-canonical nucleotides. In some cases the oligonucleotide primers may comprise a hybridizing portion which comprises random nucleotides, such as for example random dimers, trimers, tetramers, pentamers, hexamers, heptamers, octomers, nonomers, decamers, undecamers, dodecamers, tridecamers, tetradecamers, or longer. In other cases, the hybridizing portion may comprise a non random sequence such as a polyT sequence. In still other cases, the hybridizing portion of some of the oligonucleotide primers may comprise random nucleotides, while the hybridizing portion of some of the nucleotides comprise non-random sequences, such as polyT or "not so random sequences." In some cases, the hybridizing portion of the oligonucleotide primers may comprise "not so random sequences" such as for example a pool of sequences which randomly or pseudo-randomly prime desired sequences such as total mRNA or a substantial fraction thereof, but do not prime undesired sequences such as rRNA.

A "random primer," as used herein, can be a primer that generally comprises a sequence that is designed not necessarily based on a particular or specific sequence in a sample, but rather is based on a statistical expectation (or an empirical observation) that the sequence of the random primer is hybridizable (under a given set of conditions) to one or more sequences in the sample. A random primer can generally be an oligonucleotide or a population of oligonucleotides comprising a random sequence(s) in which the nucleotides at a given position on the oligonucleotide can be any of the four nucleotides, or any of a selected group of the four nucleotides (for example only three of the four nucleotides, or only two of the four nucleotides). In some cases all of the positions of the oligonucleotide or population of oligonucleotides can be any of the four nucleotides; in other cases, only a portion of the positions, for instance a particular region, of the oligonucleotide will comprise positions which can be any of the four bases. In some cases, the portion of the oligonucleotide which comprises positions which can be any of the four bases is about 1, 2, 3, 4, 5, 6, 7, 8, 9, 10, 11, 12, 13, 14, or about 15-20 nucleotides in length. In some cases, the portion of the oligonucleotide which comprises positions which can be any of the four bases is about 5-20, 5-15, 5-10, 4-8, 10-20, 15-20, or 10-15 nucleotides in length. In some cases, a random primer may comprise a tailed primer having a 3'-region that comprises a random sequence and a 5'-region that is a non-hybridizing sequence that comprises a specific, non-random sequence. The 3'-region may also comprise a random sequence in combination with a region that comprises poly-T sequences. The sequence of a random primer (or its complement) may or may not be naturally-occurring, or may or may not be present in a pool of sequences in a sample of interest. The amplification of a plurality of RNA species in a single reaction mixture would generally, but not necessarily, employ a multiplicity, or a large multiplicity, of random primers. As is well understood in the art, a "random primer" can also refer to a primer that is a member of a population of primers (a plurality of random primers) which collectively are designed to hybridize to a desired and/or a significant number of target sequences. A random primer may hybridize at a plurality of sites on a nucleic acid sequence. The use of random primers provides a method for generating primer extension products complementary to a target polynucleotide which does not require prior knowledge of the exact sequence of the target. In some embodiments one portion of a primer is random, and another portion of the primer comprises a defined sequence. For example, in some embodiments, a 3'-portion of the primer will comprise a random sequence, while the 5'-portion of the primer comprises a defined sequence. In some embodiments a 3'-random portion of the primer will comprise DNA, and a 5'-portion defined portion of the primer will comprise RNA; in other embodiments, both the 3' and 5'-portions will comprise DNA. In some embodiments, the 5'-portion will contain a defined sequence and the 3'-portion will comprise a poly-dT sequence that is hybridizable to a multiplicity of RNAs in a sample (such as all mRNA).

The hybridizing portion of the oligonucleotide primers may comprise a pool of hybridizing portions which hybridize to a number of sequences or fragments to be analyzed such as for example, 1; 2; 3; 4; 5; 6; 7; 8; 9; 10; 11; 12; 13; 14; 15; 16; 17; 18; 19; 20; 25; 30; 35; 40; 45; 50; 55; 60; 75; 100; 150; 200; 250; 300; 400; 500; 600; 750; 1000; 10,000; 15,000; 20,000; 25,000; 30,000; 40,000; 50,000; 60,000; 75,000; 100,000; 150,000; 200,000; 250,000 or more sequences or fragments. In some cases, each fragment may be hybridized to one primer, in other cases, each fragment is hybridized on average to 1, 2, 3, 4, 5, 6, 7, 8, 9, 10, 11, 12, 13, 14, 15, 16, 17, 18, 19, 20 or more oligonucleotide primers. Oligonucleotide primers suitable for the methods of the present invention are provided herein.

The olignucleotide primers may be extended along the input nucleic acid template to which they are hybridized. In some cases, the extension may be performed with a polymerase such as for example any of the polymerases provided herein including polymerases comprising strand displacement activity. Exemplary DNA dependent DNA polymerases suitable for the methods of the present invention include but are not limited to Klenow polymerase, with or without 3'-exonuclease, Bst DNA polymerase, Bca polymerase, φ29 DNA polymerase, Vent polymerase, Deep Vent polymerase, Taq polymerase, T4 polymerase, and *E. coli* DNA polymerase 1, derivatives thereof, or mixture of polymerases. In some cases, the polymerase does not comprise a 5'-exonuclease activity. In other cases, the polymerase comprises 5' exonuclease activity. In some cases, the primer extension of the present invention may be performed using a polymerase comprising strong strand displacement activity such as for example Bst polymerase. In other cases, the primer extension of the present invention may be performed using a polymerase comprising weak or no strand displacement activity. One skilled in the art may recognize the advantages and disadvantages of the use of strand displacement activity during the primer extension step, and which polymerases may be expected to provide strand displacement activity (see e.g., New England Biolabs Polymerases). For example, strand displacement activity may be useful in ensuring whole genome or whole transcriptome coverage during the random priming and extension step. Strand displacement activity may further be useful in the generation of double stranded amplification products during the priming and extension step. Alternatively, a polymerase which comprises weak or no strand displacement activity may be useful in the generation of single stranded nucleic acid products during primer hybridization and extension that are hybridized to the template nucleic acid.

An "RNA-dependent DNA polymerase" or "reverse transcriptase" ("RT") is an enzyme that synthesizes a complementary DNA copy from an RNA template. All known reverse transcriptases also have the ability to make a complementary DNA copy from a DNA template; thus, they are both RNA- and DNA-dependent DNA polymerases. Reverse transcriptases may also have an RNase H activity. Some examples of reverse transcriptases are reverse transcriptase derived from Maloney murine leukemia virus (MMLV-RT), avian myeloblastosis virus, retroviral reverse transcriptase, retrotransposon reverse transcriptase, hepatitis B reverse transcriptase, cauliflower mosaic virus reverse transcriptase, bacterial reverse transcriptase, *E. coli* DNA polymerase and klenow fragment, and Tth DNA polymerase. A primer can be used to initiate synthesis with both RNA and DNA templates. In other examples a DNA dependent DNA polymerase may also comprise an RNA-dependent DNA polymerase such as Klenow polymerase, Bst DNA polymerase and the like.

The extension of hybridized oligonucleotide primers, at least a portion of which may comprise random hybridizing portions, non-random hybridizing portions, not-so random hybridizing portions or a combination thereof, with a polymerase comprising strand displacement activity may provide for the generation of double stranded nucleic acid product fragments. In some cases, the extension of hybridized oligonucleotide primers, at least a portion of which comprise random hybridizing portions, with a polymerase comprising strand displacement activity may produce double stranded nucleic acid products comprising a mixture of double stranded nucleic acid fragment products produced in the polymerization reaction as well as double stranded molecules comprising template nucleic acid hybridized to one or more oligonucleotide primers.

In the embodiment where the template contains one or more non-canonical nucleotides, the products of the primer extension reaction, e.g. single or double stranded, partially double stranded, or mixtures thereof, may be distinguished from the template nucleic acid in that the template nucleic acid comprises one or more non-canonical nucleotides whereas the products of the primer extension reaction do not comprise non-canonical nucleotides, or do not comprise the same one or more non-canonical nucleotides. In some cases, double stranded products of the primer extension reaction comprise a hybrid duplex of a single strand of template nucleic acid comprising one or more non-canonical nucleotides and a single strand of primer extension product that does not comprise one or more non-canonical nucleotides, or does not comprise the same one or more non-canonical nucleotides. In other cases, double stranded products of the primer extension reaction comprise two strands, of which neither strand comprises one or more non-canonical nucleotides, or of which neither strand comprises the same one or more non-canonical nucleotides as the template nucleic acid.

The extension of hybridized oligonucleotide primers may be carried out for a suitable period of time. The period of time for the extension reaction may be anywhere from seconds to minutes to hours. For example, the extension step may include incubation of the input nucleic acid template in a reaction mixture such as the reaction mixtures provided herein with one or more oligonucleotide primers at a temperature suitable for the extension reaction (e.g., 15° C.-80° C.) for a period of between about 5 minutes and about 24 hours. Other suitable extension times include between about 1 minute and about 8 hours, about 2 minutes and about 7 hours, about 3 minutes and about 6 hours, about 4 minutes and about 5 hours, about 5 minutes and about 4 hours, about 5 minutes and about 3 hours, about 5 minutes and about 2 hours, about 10 minutes and about 2 hours, about 15 minutes and about 2 hours, about 20 minutes and about 2 hours, about 30 minutes and about 2 hours, or between about 30 minutes and about 1 hour. Still other suitable extension times include 1 minute, 2 minutes, 3 minutes, 4 minutes, 5 minutes, 6 minutes, 7 minutes, 8 minutes, 9 minutes, 10 minutes, 12 minutes, 15 minutes, 20 minutes, 30 minutes, 45 minutes, 60 minutes, 1 hour, 1.5 hours, 2 hours, 2.5 hours, 3 hours, 3.5 hours, 4 hours or more. Still other suitable extension times include about 1 minute, 2 minutes, 3 minutes, 4 minutes, 5 minutes, 6 minutes, 7 minutes, 8 minutes, 9 minutes, 10 minutes, 12 minutes, 15 minutes, 20 minutes, 30 minutes, 45 minutes, 60 minutes, 1 hour, 1.5 hours, 2 hours, 2.5 hours, 3 hours, 3.5 hours, 4 hours or more.

The extension step may be performed in a reaction mixture comprising nucleotides, labeled nucleotides or a combination thereof. For example, the hybridized oligonucleotides may be extended by one or more polymerases, such as polymerases comprising strand displacement activity or polymerases comprising weak or no strand displacement activity, along the input nucleic acid template in the presence of a mixture of dNTPs and amino allyl dNTPs. The use of amino-allyl dNTPs may allow further labeling and modification of the products of the extension reaction such as double stranded DNA fragment products. For example, the amino allyl dNTPs may provide for biotinylation, fluoresceination, labelling with Cy dyes (e.g., Cy3 or Cy5), or any other nucleic acid modification known in the art. Other modified nucleotides which are suitable for post amplification labeling by either covalent or non-covalent attachment of labels (e.g., fluorophores, chromophores, biotin, antibodies, antigens, or enzymes such as alkaline phosphatase or horse radish peroxidase) are also applicable including for example thio, phosphorothio, and amino modified nucleotides and oligonucleotides as described in U.S. Pat. Nos. 6,172,209, 5,679,785, and 5,623,070, or any other modified nucleotides provided herein.

SPIA Amplification

Amplification of the sequence regions of interest employing a linear amplification method such as the single primer isothermal amplification (SPIA) can be used. SPIA enables generation of multiple copies of the strand specific sequence regions of interest and employs a single amplification primer, thus reducing the complexity associated with multiple oligonucleotide design and manufacturing, enables the use of a generic amplification primer, and can be linear. The fidelity of quantification of the copy number of the sequence regions of interest in the complex genomic NA sample is a highly desirable feature of the presented methods of the invention.

Amplification by SPIA can occur under conditions permitting composite primer hybridization, primer extension by a DNA polymerase with strand displacement activity, cleavage of RNA from a RNA/DNA heteroduplex and strand displacement. In so far as the composite amplification primer hybridizes to the 3'-single-stranded portion (of the partially double stranded polynucleotide which is formed by cleaving RNA in the complex comprising a RNA/DNA partial heteroduplex) comprising, generally, the complement of at least a portion of the composite amplification primer sequence, composite primer hybridization may be under conditions permitting specific hybridization. In SPIA, all steps are isothermal (in the sense that thermal cycling is not required), although the temperatures for each of the steps may or may not be the same. It is understood that various other embodiments can be practiced given the general description provided above. For example, as described and exemplified herein, certain steps may be performed as temperature is changed (e.g., raised, or lowered).

Although generally only one composite amplification primer is described above, it is further understood that the SPIA amplification methods can be performed in the presence of two or more different first and/or second composite primers that randomly prime template polynucleotide. In addition, the amplification polynucleotide products of two or more separate amplification reactions conducted using two or more different first and/or second composite primers that randomly prime template polynucleotide can be combined.

The composite amplification primers are primers that are composed of RNA and DNA portions. In the amplification composite primer, both the RNA and the DNA portions are generally complementary and can hybridize to a sequence in the amplification-ready product to be copied or amplified. In some embodiments, a 3'-portion of the amplification composite primer is DNA and a 5'-portion of the composite amplification primer is RNA. The composite amplification primer is designed such that the primer is extended from the 3'-DNA portion to create a primer extension product. The 5'-RNA portion of this primer extension product in a RNA/DNA heteroduplex is susceptible to cleavage by RNase H, thus freeing a portion of the polynucleotide to the hybridization of an additional composite amplification primer. The extension of the amplification composite primer by a DNA polymerase with strand displacement activity releases the primer extension product from the original primer and creates another copy of the sequence of the polynucleotide. Repeated rounds of primer hybridization, primer extension with strand displacement DNA synthesis, and RNA cleavage create multiple copies of the strand-specific sequence of the polynucleotide.

In some embodiments, the composite amplification primer is generated in the amplification reaction mixture from a stem-loop chimeric pro-primer. The amplification reaction mixture can comprise a target partial duplex nucleic acid, for example a target partial duplex DNA, a chimeric stem-loop pro-primer, DNA polymerase with strand displacement activity, and an RNase targeting RNA in a RNA/DNA heteroduplex, for example RNase H. The RNA portion of the RNA/DNA heteroduplex at the stem of the chimeric stem-loop pro-primer can be cleaved by RNase H to generate, for example, a linear composite primer comprising a 3'-DNA and 5'-RNA. The linearized amplification primer can hybridize to a 3'-single stranded DNA portion (overhang) of a target partial duplex and can be extended by the DNA polymerase with strand displacement activity. The RNA portion of the hybridized primer in a heteroduplex can be cleaved by RNase H to free a portion of the primer binding site. A second linear composite amplification primer can hybridize to the freed primer binding site, and can be extended along the target DNA strand. The previously synthesized primer extension product (amplification product) can be displaced by the newly extended primer. Repeated cycles of primer hybridization, primer extension by strand displacement DNA polymerase, and cleavage of the RNA portion of the hybridized primer can generate multiple copies of a target nucleic acid.

Other Amplification Methods

Some aspects of the invention comprise the amplification of polynucleotide molecules or sequences within the polynucleotide molecules. Amplification generally refers to a method that can result in the formation of one or more copies of a nucleic acid or polynucleotide molecule or in the formation of one or more copies of the complement of a nucleic acid or polynucleotide molecule. Amplifications can be used in the invention, for example, to amplify or analyze a polynucleotide bound to a solid surface. The amplifications can be performed, for example, after archiving the samples in order to analyze the archived polynucleotide.

In some aspects of the invention, exponential amplification of nucleic acids or polynucleotides is used. These methods often depend on the product catalyzed formation of multiple copies of a nucleic acid or polynucleotide molecule or its complement. The amplification products are sometimes referred to as "amplicons." One such method for the enzymatic amplification of specific double stranded sequences of DNA is polymerase chain reaction (PCR). This in vitro amplification procedure is based on repeated cycles of denaturation, oligonucleotide primer annealing, and primer extension by thermophilic template dependent polynucleotide polymerase, resulting in the exponential increase in copies of the desired sequence of the polynucleotide analyte flanked by the primers. The two different PCR primers, which anneal to opposite strands of the DNA, are positioned so that the polymerase catalyzed extension product of one primer can serve as a template strand for the other, leading to the accumulation of a discrete double stranded fragment whose length is defined by the distance between the 5' ends of the oligonucleotide primers. Other amplification techniques that can be used in the methods of the provided invention include, e.g., AFLP (amplified fragment length polymorphism) PCR (see e.g.: Vos et al. 1995. AFLP:

a new technique for DNA fingerprinting. Nucleic Acids Research 23: 4407-14), allele-specific PCR (see e.g., Saiki R K, Bugawan T L, Horn G T, Mullis K B, Erlich H A (1986). Analysis of enzymatically amplified beta-globin and HLA-DQ alpha DNA with allele-specific oligonucleotide probes Nature 324: 163-166), Alu PCR, assembly PCR (see e.g., Stemmer W P, Crameri A, Ha K D, Brennan T M, Heyneker H L (1995). Single-step assembly of a gene and entire plasmid from large numbers of oligodeoxyribonucleotides Gene 164: 49-53), assymetric PCR (see e.g., Saiki R K supra), colony PCR, helicase dependent PCR (see e.g., Myriam Vincent, Yan Xu and Huimin Kong (2004). Helicase-dependent isothermal DNA amplification EMBO reports 5 (8): 795-800), hot start PCR, inverse PCR (see e.g., Ochman H, Gerber A S, Hartl D L. Genetics. 1988 November; 120(3):621-3), in situ PCR, intersequence-specific PCR or IS SR PCR, digital PCR, linear-after-the-exponential-PCR or Late PCR (see e.g., Pierce K E and Wangh L T (2007). Linear-after-the-exponential polymerase chain reaction and allied technologies Real-time detection strategies for rapid, reliable diagnosis from single cells Methods Mol. Med. 132: 65-85), long PCR, nested PCR, real-time PCR, duplex PCR, multiplex PCR, quantitative PCR, or single cell PCR.

Another method for amplification involves amplification of a single stranded polynucleotide using a single oligonucleotide primer. The single stranded polynucleotide that is to be amplified contains two non-contiguous sequences that are substantially or completely complementary to one another and, thus, are capable of hybridizing together to form a stem-loop structure. This single stranded polynucleotide already may be part of a polynucleotide analyte or may be created as the result of the presence of a polynucleotide analyte.

Another method for achieving the result of an amplification of nucleic acids is known as the ligase chain reaction (LCR). This method uses a ligase enzyme to join pairs of preformed nucleic acid probes. The probes hybridize with each complementary strand of the nucleic acid analyte, if present, and ligase is employed to bind each pair of probes together resulting in two templates that can serve in the next cycle to reiterate the particular nucleic acid sequence.

Another method for achieving nucleic acid amplification is the nucleic acid sequence based amplification (NASBA). This method is a promoter-directed, enzymatic process that induces in vitro continuous, homogeneous and isothermal amplification of a specific nucleic acid to provide RNA copies of the nucleic acid. The reagents for conducting NASBA include a first DNA primer with a 5'-tail comprising a promoter, a second DNA primer, reverse transcriptase, RNase-H, T7 RNA polymerase, NTP's and dNTP's.

Another method for amplifying a specific group of nucleic acids is the Q-beta-replicase method, which relies on the ability of Q-beta-replicase to amplify its RNA substrate exponentially. The reagents for conducting such an amplification include "midi-variant RNA" (amplifiable hybridization probe), NTP's, and Q-beta-replicase.

Another method for amplifying nucleic acids is known as 3SR and is similar to NASBA except that the RNase-H activity is present in the reverse transcriptase. Amplification by 3SR is an RNA specific target method whereby RNA is amplified in an isothermal process combining promoter directed RNA polymerase, reverse transcriptase and RNase H with target RNA. See for example Fahy et al. PCR Methods Appl. 1:25-33 (1991).

Another method for amplifying nucleic acids is the Transcription Mediated Amplification (TMA) used by Gen-Probe. The method is similar to NASBA in utilizing two enzymes in a self-sustained sequence replication. See U.S. Pat. No. 5,299,491 herein incorporated by reference.

Another method for amplification of nucleic acids is Strand Displacement Amplification (SDA) (Westin et al 2000, Nature Biotechnology, 18, 199-202; Walker et al 1992, Nucleic Acids Research, 20, 7, 1691-1696), which is an isothermal amplification technique based upon the ability of a restriction endonuclease such as HincII or BsoBI to nick the unmodified strand of a hemiphosphorothioate form of its recognition site, and the ability of an exonuclease deficient DNA polymerase such as Klenow exo minus polymerase, or Bst polymerase, to extend the 3'-end at the nick and displace the downstream DNA strand. Exponential amplification results from coupling sense and antisense reactions in which strands displaced from a sense reaction serve as targets for an antisense reaction and vice versa.

Another method for amplification of nucleic acids is Rolling Circle Amplification (RCA) (Lizardi et al. 1998, Nature Genetics, 19:225-232). RCA can be used to amplify single stranded molecules in the form of circles of nucleic acids. In its simplest form, RCA involves the hybridization of a single primer to a circular nucleic acid. Extension of the primer by a DNA polymerase with strand displacement activity results in the production of multiple copies of the circular nucleic acid concatenated into a single DNA strand.

In some embodiments of the invention, RCA is coupled with ligation. For example, a single oligonucleotide can be used both for ligation and as the circular template for RCA. This type of polynucleotide can be referred to as a "padlock probe" or a "RCA probe." For a padlock probe, both termini of the oligonucleotide contain sequences complementary to a domain within a nucleic acid sequence of interest. The first end of the padlock probe is substantially complementary to a first domain on the nucleic acid sequence of interest, and the second end of the padlock probe is substantially complementary to a second domain, adjacent to the first domain near the first domain. Hybridization of the oligonucleotide to the target nucleic acid results in the formation of a hybridization complex. Ligation of the ends of the padlock probe results in the formation of a modified hybridization complex containing a circular polynucleotide. In some cases, prior to ligation, a polymerase can fill in the gap by extending one end of the padlock probe. The circular polynucleotide thus formed can serve as a template for RCA that, with the addition of a polymerase, results in the formation of an amplified product nucleic acid. The methods of the invention described herein can produce amplified products with defined sequences on both the 5'- and 3'-ends. Such amplified products can be used as padlock probes.

Some aspects of the invention utilize the linear amplification of nucleic acids or polynucleotides. Linear amplification generally refers to a method that involves the formation of one or more copies of the complement of only one strand of a nucleic acid or polynucleotide molecule, usually a nucleic acid or polynucleotide analyte. Thus, the primary difference between linear amplification and exponential amplification is that in the latter process, the product serves as substrate for the formation of more product, whereas in the former process the starting sequence is the substrate for the formation of product but the product of the reaction, i.e. the replication of the starting template, is not a substrate for generation of products. In linear amplification the amount of product formed increases as a linear function of time as opposed to exponential amplification where the amount of product formed is an exponential function of time.

In some embodiments, amplification methods can be solid-phase amplification, polony amplification, colony amplification, emulsion PCR, bead RCA, surface RCA, surface SDA, etc., as will be recognized by one of skill in the art. In some embodiments, amplification methods that results in amplification of free DNA molecules in solution or tethered to a suitable matrix by only one end of the DNA molecule can be used. Methods that rely on bridge PCR, where both PCR primers are attached to a surface (see, e.g., WO 2000/018957 and Adessi et al., Nucleic Acids Research (2000): 28(20): E87) can be used. In some cases the methods of the invention can create a "polymerase colony technology," or "polony." referring to a multiplex amplification that maintains spatial clustering of identical amplicons (see Harvard Molecular Technology Group and Lipper Center for Computational Genetics website). These include, for example, in situ polonies (Mitra and Church, Nucleic Acid Research 27, e34, Dec. 15, 1999), in situ rolling circle amplification (RCA) (Lizardi et al., Nature Genetics 19, 225, July 1998), bridge PCR (U.S. Pat. No. 5,641,658), picotiter PCR (Leamon et al., Electrophoresis 24, 3769, November 2003), and emulsion PCR (Dressman et al., PNAS 100, 8817, Jul. 22, 2003). The methods of the invention provide new methods for generating and using polonies.

Downstream Applications for Whole Transcriptome Analysis

An important aspect of the invention is that the methods and compositions disclosed herein can be efficiently and cost-effectively utilized for downstream analyses, such as next generation sequencing or hybridization platforms, with minimal loss of biological material of interest. Specifically, the methods of the invention are useful for sequencing a whole transcriptome from a NGS library with depleted or reduced rRNA content.

Sequencing

In one embodiment, the invention provides for products ready for amplification in preparation for sequencing. In some embodiments, the target polynucleotides are pooled followed by sequencing one or more polynucleotides in the pool. Sequencing methods utilizing adaptor incorporated sequences are well known in the art and are further described, for example, in U.S. Pat. Nos. 8,053,192 and 8,017,335.

Sequencing processes are generally template dependent. Nucleic acid sequence analysis that employs template dependent synthesis identifies individual bases, or groups of bases as they are added during a template mediated synthesis reaction, such as a primer extension reaction, where the identity of the base is complementary to the template sequence to which the primer sequence is hybridized during synthesis. Other such processes include ligation driven processes, where oligonucleotides or polynucleotides are complexed with an underlying template sequence, in order to identify the sequence of nucleotides in that sequence. Typically, such processes are enzymatically mediated using nucleic acid polymerases, such as DNA polymerases, RNA polymerases, reverse transcriptases, and the like, or other enzymes such as in the case of ligation driven processes, e.g., ligases.

Sequence analysis using template dependent synthesis can include a number of different processes. For example, in the ubiquitously practiced four-color Sanger sequencing methods, a population of template molecules is used to create a population of complementary fragment sequences. Primer extension is carried out in the presence of the four naturally occurring nucleotides, and with a sub-population of dye labeled terminator nucleotides, e.g., dideoxyribonucleotides, where each type of terminator (ddATP, ddGTP, ddTTP, ddCTP) includes a different detectable label. As a result, a nested set of fragments is created where the fragments terminate at each nucleotide in the sequence beyond the primer, and are labeled in a manner that permits identification of the terminating nucleotide. The nested fragment population is then subjected to size based separation, e.g., using capillary electrophoresis, and the labels associated with each different sized fragment is identified to identify the terminating nucleotide. As a result, the sequence of labels moving past a detector in the separation system provides a direct readout of the sequence information of the synthesized fragments, and by complementarity, the underlying template (See, e.g., U.S. Pat. No. 5,171,534, incorporated herein by reference in its entirety for all purposes).

Other examples of template dependent sequencing methods include sequence by synthesis processes, where individual nucleotides are identified iteratively, as they are added to the growing primer extension product.

Pyrosequencing is an example of a sequence by synthesis process that identifies the incorporation of a nucleotide by assaying the resulting synthesis mixture for the presence of by-products of the sequencing reaction, namely pyrophosphate. In particular, a primer/template/polymerase complex is contacted with a single type of nucleotide. If that nucleotide is incorporated, the polymerization reaction cleaves the nucleoside triphosphate between the α and β phosphates of the triphosphate chain, releasing pyrophosphate. The presence of released pyrophosphate is then identified using a chemiluminescent enzyme reporter system that converts the pyrophosphate, with AMP, into ATP, then measures ATP using a luciferase enzyme to produce measurable light signals. Where light is detected, the base is incorporated, where no light is detected, the base is not incorporated. Following appropriate washing steps, the various bases are cyclically contacted with the complex to sequentially identify subsequent bases in the template sequence. See, e.g., U.S. Pat. No. 6,210,891, incorporated herein by reference in its entirety for all purposes).

In related processes, the primer/template/polymerase complex is immobilized upon a substrate and the complex is contacted with labeled nucleotides. The immobilization of the complex may be through the primer sequence, the template sequence and/or the polymerase enzyme, and may be covalent or noncovalent. For example, immobilization of the complex can be via a linkage between the polymerase or the primer and the substrate surface. A variety of types of linkages are useful for this attachment, including, e.g., provision of biotinylated surface components, using e.g., biotin-PEG-silane linkage chemistries, followed by biotinylation of the molecule to be immobilized, and subsequent linkage through, e.g., a streptavidin bridge. Other synthetic coupling chemistries, as well as non-specific protein adsorption can also be employed for immobilization. In alternate configurations, the nucleotides are provided with and without removable terminator groups. Upon incorporation, the label is coupled with the complex and is thus detectable. In the case of terminator bearing nucleotides, all four different nucleotides, bearing individually identifiable labels, are contacted with the complex. Incorporation of the labeled nucleotide arrests extension, by virtue of the presence of the terminator, and adds the label to the complex. The label and terminator are then removed from the incorporated nucleotide, and following appropriate washing steps, the process is repeated. In the case of non-terminated nucleotides, a single type of labeled nucleotide is added to the complex to determine whether it will be incorporated, as with pyrosequencing. Following removal of the label group on the nucleotide and appropriate washing steps, the various different nucleotides are cycled through the reaction mixture in the same process. See, e.g., U.S. Pat. No. 6,833,246, incorporated herein by reference in its entirety for all purposes). For example, the Illumina Genome Analyzer System is based on technology described in WO 98/44151, hereby incorporated by reference, wherein DNA molecules are bound to a sequencing platform (flow cell) via an anchor probe binding site (otherwise referred to as a flow cell binding site) and amplified in situ on a glass slide. The DNA molecules are then annealed to a sequencing primer and sequenced in parallel base-by-base using a reversible terminator approach. Typically, the Illumina Genome Analyzer System utilizes flow-cells with 8 channels, generating sequencing reads of 18 to 36 bases in length, generating >1.3 Gbp of high quality data per run. Accordingly, the methods of the invention are useful for sequencing by the method commercialized by Illumina, as described U.S. Pat. Nos. 5,750,341; 6,306,597; and 5,969,119. Directional (strand-specific) cDNA libraries are prepared using the methods of the present invention, and the selected single-stranded nucleic acid is amplified, for example, by PCR. The resulting nucleic acid is then denatured and the single-stranded amplified polynucleotides are randomly attached to the inside surface of flow-cell channels. Unlabeled nucleotides are added to initiate solid-phase bridge amplification to produce dense clusters of double-stranded DNA. To initiate the first base sequencing cycle, four labeled reversible terminators, primers, and DNA polymerase are added. After laser excitation, fluorescence from each cluster on the flow cell is imaged. The identity of the first base for each cluster is then recorded. Cycles of sequencing are performed to determine the fragment sequence one base at a time.

In yet a further sequence by synthesis process, the incorporation of differently labeled nucleotides is observed in real time as template dependent synthesis is carried out. In particular, an individual immobilized primer/template/polymerase complex is observed as fluorescently labeled nucleotides are incorporated, permitting real time identification of each added base as it is added. In this process, label groups are attached to a portion of the nucleotide that is cleaved during incorporation. For example, by attaching the label group to a portion of the phosphate chain removed during incorporation, i.e., a $\beta$, $\gamma$, or other terminal phosphate group on a nucleoside polyphosphate, the label is not incorporated into the nascent strand, and instead, natural DNA is produced. Observation of individual molecules typically involves the optical confinement of the complex within a very small illumination volume. By optically confining the complex, one creates a monitored region in which randomly diffusing nucleotides are present for a very short period of time, while incorporated nucleotides are retained within the observation volume for longer as they are being incorporated. This results in a characteristic signal associated with the incorporation event, which is also characterized by a signal profile that is characteristic of the base being added. In related aspects, interacting label components, such as fluorescent resonant energy transfer (FRET) dye pairs, are provided upon the polymerase or other portion of the complex and the incorporating nucleotide, such that the incorporation event puts the labeling components in interactive proximity, and a characteristic signal results, that is again, also characteristic of the base being incorporated (See, e.g., U.S. Pat. Nos. 6,056,661, 6,917,726, 7,033,764, 7,052,847, 7,056,676, 7,170,050, 7,361,466, 7,416,844 and Published U.S. Patent Application No. 2007-0134128, the full disclosures of which are hereby incorporated herein by reference in their entirety for all purposes).

In some embodiments, the nucleic acids in the sample can be sequenced by ligation. This method uses a DNA ligase enzyme to identify the target sequence, for example, as used in the polony method and in the SOLiD technology (Applied Biosystems, now Invitrogen). In general, a pool of all possible oligonucleotides of a fixed length is provided, labeled according to the sequenced position. Oligonucleotides are annealed and ligated; the preferential ligation by DNA ligase for matching sequences results in a signal corresponding to the complementary sequence at that position.

Thus, in some embodiments, the methods of the invention are useful for preparing target polynucleotides for sequencing by the sequencing by ligation methods commercialized by Applied Biosystems (e.g., SOLiD sequencing). In other embodiments, the methods are useful for preparing target polynucleotides for sequencing by synthesis using the methods commercialized by 454/Roche Life Sciences, including but not limited to the methods and apparatus described in Margulies et al., Nature (2005) 437:376-380 (2005); and U.S. Pat. Nos. 7,244,559; 7,335,762; 7,211,390; 7,244,567; 7,264,929; and 7,323,305. In other embodiments, the methods are useful for preparing target polynucleotide(s) for sequencing by the methods commercialized by Helicos BioSciences Corporation (Cambridge, Mass.) as described in U.S. application Ser. No. 11/167,046, and U.S. Pat. Nos. 7,501,245; 7,491,498; 7,276,720; and in U.S. Patent Application Publication Nos. US20090061439; US20080087826; US20060286566; US20060024711; US20060024678; US20080213770; and US20080103058. In other embodiments, the methods are useful for preparing target polynucleotide(s) for sequencing by the methods commercialized by Pacific Biosciences as described in U.S. Pat. Nos. 7,462,452; 7,476,504; 7,405,281; 7,170,050; 7,462,468; 7,476,503; 7,315,019; 7,302,146; 7,313,308; and U.S. Application Publication Nos. US20090029385; US20090068655; US20090024331; and US20080206764. In general, double stranded fragment polynucleotides can be prepared by the methods of the present invention. The polynucleotides can then be immobilized in zero mode waveguide arrays. The methods may include a step of rendering the nucleic acid bound to the waveguide arrays single stranded or partially single stranded. Polymerase and labeled nucleotides are added in a reaction mixture, and nucleotide incorporations are visualized via fluorescent labels attached to the terminal phosphate groups of the nucleotides. The fluorescent labels are clipped off as part of the nucleotide incorporation. In some cases, circular templates are utilized to enable multiple reads on a single molecule.

Another example of a sequencing technique that can be used in the methods of the provided invention is nanopore sequencing (see e.g. Soni G V and Meller A. (2007) Clin Chem 53: 1996-2001). A nanopore can be a small hole of the order of 1 nanometer in diameter. Immersion of a nanopore in a conducting fluid and application of a potential across it can result in a slight electrical current due to conduction of ions through the nanopore. The amount of current that flows is sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore can represent a reading of the DNA sequence.

Another example of a sequencing technique that can be used in the methods of the provided invention is semiconductor sequencing provided by Ion Torrent (e.g., using the Ion Personal Genome Machine (PGM)). Ion Torrent technology can use a semiconductor chip with multiple layers, e.g., a layer with micro-machined wells, an ion-sensitive layer, and an ion sensor layer. Nucleic acids can be introduced into the wells, e.g., a clonal population of single nucleic can be attached to a single bead, and the bead can be introduced into a well. To initiate sequencing of the nucleic acids on the beads, one type of deoxyribonucleotide (e.g., dATP, dCTP, dGTP, or dTTP) can be introduced into the wells. When one or more nucleotides are incorporated by DNA polymerase, protons (hydrogen ions) are released in the well, which can be detected by the ion sensor. The semiconductor chip can then be washed and the process can be repeated with a different deoxyribonucleotide. A plurality of nucleic acids can be sequenced in the wells of a semiconductor chip. The semiconductor chip can comprise chemical-sensitive field effect transistor (chemFET) arrays to sequence DNA (for example, as described in U.S. Patent Application Publication No. 20090026082). Incorporation of one or more triphosphates into a new nucleic acid strand at the 3' end of the sequencing primer can be detected by a change in current by a chemFET. An array can have multiple chemFET sensors.\

In some embodiments, sequencing comprises extension of a sequencing primer comprising a sequence hybridizable to at least a portion of the complement of the first adaptor oligonucleotide. In some embodiments, sequencing comprises extension of a sequencing primer comprising a sequence hybridizable to at least a portion of the complement of the second adaptor oligonucleotide. A sequencing primer may be of any suitable length, such as about, less than about, or more than about 10, 15, 20, 25, 30, 35, 40, 45, 50, 55, 60, 65, 70, 75, 80, 90, 100, or more nucleotides, any portion or all of which may be complementary to the corresponding target sequence (e.g. about, less than about, or more than about 5, 10, 15, 20, 25, 30, 35, 40, 45, 50, or more nucleotides). In some embodiments, sequencing comprises a calibration step, wherein the calibration is based on each of the nucleotides at one or more nucleotide positions in the barcode sequences. Calibration can be useful in processing the sequencing data, for example, by facilitating or increasing the accuracy of identifying a base at a given position in the sequence.

In some embodiments, accurate identification of the sample from which a target polynucleotide is derived is based on at least a portion of the sequence obtained for the target polynucleotide and is at least 90%, 95%, 96%, 97%, 98%, 99%, 99.5%, 99.8%, 99.85%, 99.9%, 99.95%, 99.99%, or more accurate. In some embodiments, the sample source of a target polynucleotide is identified based on a single barcode contained in the sequence. In some embodiments, accuracy can be increased by identifying the source of a target polynucleotide using two or more barcodes contained in the sequence. Multiple barcodes can be joined to a target polynucleotide by the incorporation of multiple barcodes into a single adaptor/primer to which a target polynucleotide is joined, and/or by joining two or more adaptors/primers having one or more barcodes to a target polynucleotide. In some embodiments, the identity of the sample source of a target polynucleotide comprising two or more barcode sequences may be accurately determined using only one of the barcode sequences that it comprises. In general, accurate identification of a sample from which a target polynucleotide is derived comprises correct identification of a sample source from among two or more samples in a pool, such as about, less than about, or more than about 2, 3, 4, 5, 6, 7, 8, 9, 10, 12, 16, 20, 24, 28, 32, 36, 40, 50, 60, 70, 80, 90, 100, 128, 192, 384, 500, 1000 or more samples in a pool.

In some embodiments, the methods are useful for preparing target polynucleotide(s) from selectively enriched populations of specific sequence regions of interest in a strand-specific manner for sequencing by the methods well known in the art and further described below.

For example the methods are useful for sequencing by the method commercialized by Illumina as described U.S. Pat. Nos. 5,750,341; 6,306,597; and 5,969,119. In general, double stranded fragment polynucleotides can be prepared by the methods of the present invention to produce amplified nucleic acid sequences tagged at one (e.g., (A)/(A') or both ends (e.g., (A)/(A') and (C)/(C')). In some cases, single stranded nucleic acid tagged at one or both ends is amplified by the methods of the present invention (e.g., by SPIA or linear PCR). The resulting nucleic acid is then denatured and the single stranded amplified polynucleotides are randomly attached to the inside surface of flow-cell channels. Unlabeled nucleotides are added to initiate solid-phase bridge amplification to produce dense clusters of double-stranded DNA. To initiate the first base sequencing cycle, four labeled reversible terminators, primers, and DNA polymerase are added. After laser excitation, fluorescence from each cluster on the flow cell is imaged. The identity of the first base for each cluster is then recorded. Cycles of sequencing are performed to determine the fragment sequence one base at a time. For paired-end sequencing, such as for example, when the polynucleotides are labeled at both ends by the methods of the present invention, sequencing templates can be regenerated in-situ so that the opposite end of the fragment can also be sequenced.

Kits

Any of the compositions described herein may be comprised in a kit. In a non-limiting example, the kit, in a suitable container, comprises: an adaptor or several adaptors, one or more of oligonucleotide primers and reagents for ligation, primer extension and amplification. The kit may also comprise means for purification, such as a bead suspension, and nucleic acid modifying enzymes.

The containers of the kits will generally include at least one vial, test tube, flask, bottle, syringe or other containers, into which a component may be placed, and preferably, suitably aliquotted. Where there is more than one component in the kit, the kit also will generally contain a second, third or other additional container into which the additional components may be separately placed. However, various combinations of components may be comprised in a container.

When the components of the kit are provided in one or more liquid solutions, the liquid solution can be an aqueous solution. However, the components of the kit may be provided as dried powder(s). When reagents and/or components are provided as a dry powder, the powder can be reconstituted by the addition of a suitable solvent.

In various embodiments, a kit according to the invention comprises one or more of a restriction endonuclease, e.g. BspQI, a ligase, a polymerase, e.g. a hot start polymerase such as MyTaq, a cleavage agent, a library of probes capable of acting as a primer for a primer extension reaction, and one or more non-canonical nucleotides, e.g. uracil or inosine. In some embodiments, the cleavage agent comprises one or more of a glycosylase, e.g. UNG or UDG, a primary amine, a polyamine, e.g. DMED, and endonuclease V.

In some embodiments, a kit comprises one or more of a first adapter comprising one or more non-canonical nucleotides on one strand and lacking 5' phosphates, a second adapter lacking said one or more non-canonical nucleotides and lacking 5' phosphates, and a set of primers specific to the adaptor sequences. In some embodiments, the second adapter comprises a recognition sequence for a restriction endonuclease.

In some embodiments, a kit comprises one or more of a first adapter lacking 5' phosphates, a plurality of partial duplex primers each comprising a 3' overhang and comprising a shared sequence within a double-stranded portion, and a primer that is hybridizable a sequence reverse complimentary to the adapter. In some embodiments, the first adapter comprises a recognition sequence for a restriction endonuclease. In some embodiments, the plurality of partial duplex primers comprise at least two partial duplex primers with dissimilar 3' overhang sequences.

In some embodiments, the kit comprises one or more of a first adapter lacking 5' phosphates, a plurality of partial duplex primers each comprising a 3' overhang, comprising a shared sequence within a double-stranded portion, and the strand of the plurality of partial duplex primers with the 3' overhang lacking adenines in the shared sequence within the double-stranded portion, and a set of primers that are hybridizable to a sequence reverse complimentary to the adapter and the shared sequence of the partial duplex primers opposite the 3' overhang. In some embodiments, the first adapter comprises a recognition sequence for the restriction endonuclease. In some embodiments, the plurality of partial duplex primers comprise at least two partial duplex primers with dissimilar 3' overhang sequences.

A kit will preferably include instructions for employing, the kit components as well the use of any other reagent not included in the kit. Instructions may include variations that can be implemented.

In one aspect, the invention provides kits containing any one or more of the elements disclosed in the above methods and compositions. In some embodiments, a kit comprises a composition of the invention, in one or more containers. In some embodiments, the invention provides kits comprising adaptors, primers, and/or other oligonucleotides described herein. The adaptors, primers, other oligonucleotides, and reagents can be, without limitation, any of those described above. Elements of the kit can further be provided, without limitation, in any suitable amounts and/or using any of the combinations (such as in the same kit or same container) described above or any other suitable combination known in the art. The kits may further comprise additional agents, such as those described above, for use according to the methods of the invention. The kit elements can be provided in any suitable container, including but not limited to test tubes, vials, flasks, bottles, ampules, syringes, or the like. The agents can be provided in a form that may be directly used in the methods of the invention, or in a form that requires preparation prior to use, such as in the reconstitution of lyophilized agents. Agents may be provided in aliquots for single-use or as stocks from which multiple uses, such as in a number of reaction, may be obtained.

Products Based on the Methods of the Invention

Products based on the methods of the invention may be commercialized by the Applicants under the trade name Encore Complete Prokaryotic RNA-Seq™. Encore is a trademark of NuGEN Technologies, Inc.

EXAMPLES

Example 1—Depletion of Bacterial Ribosomal RNA Fragments from Directional (i.e. Strand-Specific) Whole Transcriptome Libraries This example describes the depletion of bacterial rRNA fragments from four directional cDNA libraries generated from *E. coli* total RNA, using insert-dependent adaptor cleavage (InDA-C) probes that target highly conserved prokaryotic 16S and as 23S rRNA transcript regions.

Probe Design and Synthesis

InDA-C probes that target prokaryotic rRNA transcripts were designed by comparing the ribosomal operons from a phylogenetically diverse set of 40 bacterial strains and 10 archaeal strains using the ClustalW multiple sequence alignment program (European Bioinformatics Institute). Candidate primer sequences were first selected from highly conserved sequences identified in 16S rRNA (9 sites) and 23S rRNA (7 sites) subunits. These conserved regions were computationally fragmented and analyzed by Primer3 (Steve Rozen and Helen J. Skaletsky (2000) Primer3 on the WWW for general users and for biologist programmers. In: Krawetz S, Misener S (eds) Bioinformatics Methods and Protocols: Methods in Molecular Biology. Humana Press, Totowa, N.J., pp 365-386). These sequences were then filtered for optimal predicted melting temperatures ranging from 55-65° C. and length. Oligonucleotides corresponding to the rRNA sense strand were synthesized individually and pooled in equimolar proportions. The final primer pool was comprised of 205 oligonucleotides ranging from 14-18 nt in length. Some primers were synthesized with one or more nucleotide analogues, such as Locked Nucleic Acid (LNA) bases, to increase their respective melting temperatures. The probe mix was diluted to 25 times the final concentration used in InDA-C depletion reactions (375 nM per species, 15 nM final).

Generation of Strand-Specific cDNA Libraries

The Encore Complete RNA-Seq Library System (NuGEN Technologies, p/n 0311) was used to generate four strand-specific cDNA libraries from 100 ng of *E. coli* total RNA (Life Technologies, p/n AM7940) extracted from a liquid culture harvested at the mid-log phase of growth in rich media. The reverse transcription reaction was carried out according to the manufacturer's instructions except that the primer supplied in the kit was replaced with the first strand primer from the Ovation Prokaryotic RNA-Seq System (NuGEN Technologies, p/n 9030). Second strand DNA synthesis was performed as recommended in the kit and the double-stranded cDNA was sheared with a Covaris S-series device using the 200 bp sonication protocol provided with the instrument (10% duty cycle, 200 cycles/burst, 5 intensity, 180 seconds). Purification of the fragmented cDNA was accomplished by adding 2 volumes of Ampure XP beads (Agencourt Genomics), washed twice with 70% ethanol and eluted with 15 μL of water. Ten microliters of each sample were prepared for ligation using the End Repair reaction as described in the kit. Ligation was performed with the reverse adaptor provided in the kit and a custom forward adaptor containing deoxyuridine and a single base substitution in the BspQI recognition site (5'-TACACTCUTTCCCUACAC-GACGAUCTTCCGAUCT-3' (SEQ ID NO: 1)). Following the Strand Selection I reaction, samples were purified with beads as before except that elution volume was 25 μL with 18 μL of that taken forward.

Ribosomal RNA Depletion

Ribosomal DNA fragments were selectively depleted from the library in three distinct steps: 1) base excision/rRNA-specific primer extension, 2) reverse adaptor cleavage and 3) PCR enrichment. The first step was performed by combining each 18 µL sample with 7 µL of mastermix containing 1 µL of InDA-C rRNA probes, 5 µL of 5×MyTaq polymerase buffer, 0.5 µL of Strand Selection II enzyme (SS4) from the Encore Complete RNA-Seq system and 0.5 µL of HS MyTaq polymerase (Bioline p/n BIO-21111). This solution was placed in a thermal cycler, heated to 37° C. for 10 minutes to complete strand selection and generate single-stranded library fragments, heated to 95° C. for 2 minutes to activate the hot start polymerase, cooled to 50° C. for 30 seconds to anneal rRNA probes, heated to 65° C. for 5 minutes to allow primer extension from insert into the reverse adaptor sequence. Samples were cooled to 4° C. before adding 25 µL of adaptor cleavage mastermix containing 1×MyTaq polymerase buffer and 2.5 units of BspQI restriction enzyme (New England Biolabs p/n R0712). Reactions were carried out in a thermal cycler by heating to 55° C. for 5 minutes and 95° C. for 5 minutes before cooling to 4° C. Enrichment of non-rRNA fragments was accomplished by adding 50 µL of 2×PCR mastermix containing 1×MyTaq polymerase buffer, 2.5 units of HS MyTaq polymerase and 8 µL of P2 primer mix provided in the kit. Samples were placed in a thermal cycler, heated to 95° C. for 2 minutes to activate the polymerase and amplified using a 2-step temperature routine: 2 cycles of 95° C. for 30 seconds, 60° C. for 90 seconds and 18 cycles of 95° C. for 30 second, 65° C. for 90 seconds. PCR products were purified using AMPure XP beads and analyzed with a 2100 Bioanalyzer (Agilent Technologies). Libraries were sequenced in single end format on an Illumina GA2X instrument. Raw data were processed using Illumina base calling software and mapped to the *E. coli* K-12 (substrain MG1655) reference genome (Genbank Accession #AP009048). The orientation of reads is expected to be in the sense strand orientation relative to RNA templates.

Only one of the four cDNA aliquots was converted to a library using the full complement of InDA-C components (Test4). The other three libraries were constructed with one or more of the InDA-C reagents missing (Test1, Test2 and Test3). A control library generated with random primers from the same RNA was used as a benchmark for the undepleted input sample (ctrl). The mapping statistics for the control and each of the test libraries are shown in FIG. 2. A comparison of expression profiles from the four test libraries is shown in FIG. 3. The targeted depletion of 16S rRNA sites by universal prokaryotic InDA-C probes is depicted in FIG. 4.

Example 2—Depletion of Mitochondrial DNA Fragments from a Genomic DNA Library

This example describes the depletion of mitochondrial DNA fragments from a genomic DNA library, using insert-dependent adaptor cleavage (InDA-C) probes that target the mitochondrial genome.

Probe Design and Synthesis

InDA-C probes that anneal to both strands of the hg19 version of the human mitochondrial genome sequence were selected within mitochondrial-specific segments identified by the "Duke 20 bp uniqueness" tracks provided by the UCSC Genome Browser. These sequences were then filtered for optimal predicted melting temperatures and length. Oligonucleotides ranging from 20-25 nt in length were synthesized individually and pooled in equimolar proportions. The resulting probe mix was diluted to 25 times the final concentration used in InDA-C depletion reactions (375 nM per species, 15 nM final).

Generation of Genomic DNA Libraries

The Ovation Ultralow Library System (NuGEN Technologies, San Carlos, Calif.) was used to generate DNA libraries from 10 ng of human male DNA (Promega). The DNA was sheared with a Covaris S-series device using the 200 bp sonication protocol provided with the instrument (10% duty cycle, 200 cycles/burst, 5 intensity, 180 seconds). Purification of the fragmented DNA was accomplished by adding 2 volumes of Ampure XP beads (Agencourt Genomics), washed twice with 70% ethanol and eluted with 15 µL of water. Ten microliters of each sample were prepared for ligation using the End Repair reaction as described in the kit. Ligation was performed with a custom forward adaptor and the Illumina TruSeq reverse adaptor. The forward adaptor contained an AsiSI recognition site (5'-GCGATCGC-3') near the ligation junction (5'-AATGATACGGCGACCAC-CGAAGATAAGAAGAaTGAcGTcAAgTGCGATCGCA-GGA TAGAT-3' (SEQ ID NO: 2)). The reverse adapter contained a BspQ1 recognition site (5'-GCTCTTC-3') near the ligation junction (5'-CAAGCAGAAGACGGCATAC-GAGATGTGACTGGAGTTCAGACGTGTGCTCTTCCG ATCT-3' (SEQ ID NO: 3)). Samples were purified with beads as before except that elution volume was 25 µL with 18 µL of that taken forward.

Mitochondrial DNA Depletion

Mitochondrial DNA fragments were selectively depleted from the library in three distinct steps: 1) denaturation/mitochondrial-specific primer extension, 2) adaptor cleavage, and 3) PCR enrichment. The first step was performed by combining each 18 µL sample with 7 µL of mastermix containing 1 µL of InDA-C mitochondrial probes, 5 µL of 5×MyTaq polymerase buffer, and 0.5 µL of HS MyTaq polymerase (Bioline p/n BIO-21111). This solution was placed in a thermal cycler, heated to 95° C. for 10 minutes to complete strand separation, generate single-stranded library fragments, and to activate the hot start polymerase, cooled to 50° C. for 30 seconds to anneal rRNA probes, heated to 65° C. for 5 minutes to allow primer extension from insert into the reverse adaptor sequence. Samples were cooled to 4° C. before adding 25 µL of adaptor cleavage mastermix containing 1×MyTaq polymerase buffer, 2.5 units of BspQI restriction enzyme (New England Biolabs p/n R0712), and 2.5 units of AsiSI restriction enzyme (New England Biolabs p/n R0630). Reactions were carried out in a thermal cycler by heating to 40° C. for 5 minutes and 95° C. for 5 minutes before cooling to 4° C. Enrichment of non-mitochondrial fragments was accomplished by adding 50 µL of 2×PCR mastermix containing 1×MyTaq polymerase buffer, 2.5 units of HS MyTaq polymerase and 8 µL of 10×PCR primer mix containing 10 µM forward primer (5'-AATGATACGGCGACCACCGA-3' (SEQ ID NO: 4)) and 10 µM reverse primer (5'-CAAGCAGAAGACGGCAT-ACG-3' (SEQ ID NO: 5)). Samples were placed in a thermal cycler, heated to 95° C. for 2 minutes to activate the polymerase and amplified using a 2-step temperature routine: 2 cycles of 95° C. for 30 seconds, 60° C. for 90 seconds and 18 cycles of 95° C. for 30 second, 65° C. for 90 seconds. PCR products were purified using AMPure XP beads and analyzed with a 2100 Bioanalyzer (Agilent Technologies). Libraries were sequenced in single end format on an Illumina GA2X instrument. Raw data were processed using Illumina base calling software and mapped to human reference genome.

Figure 5:
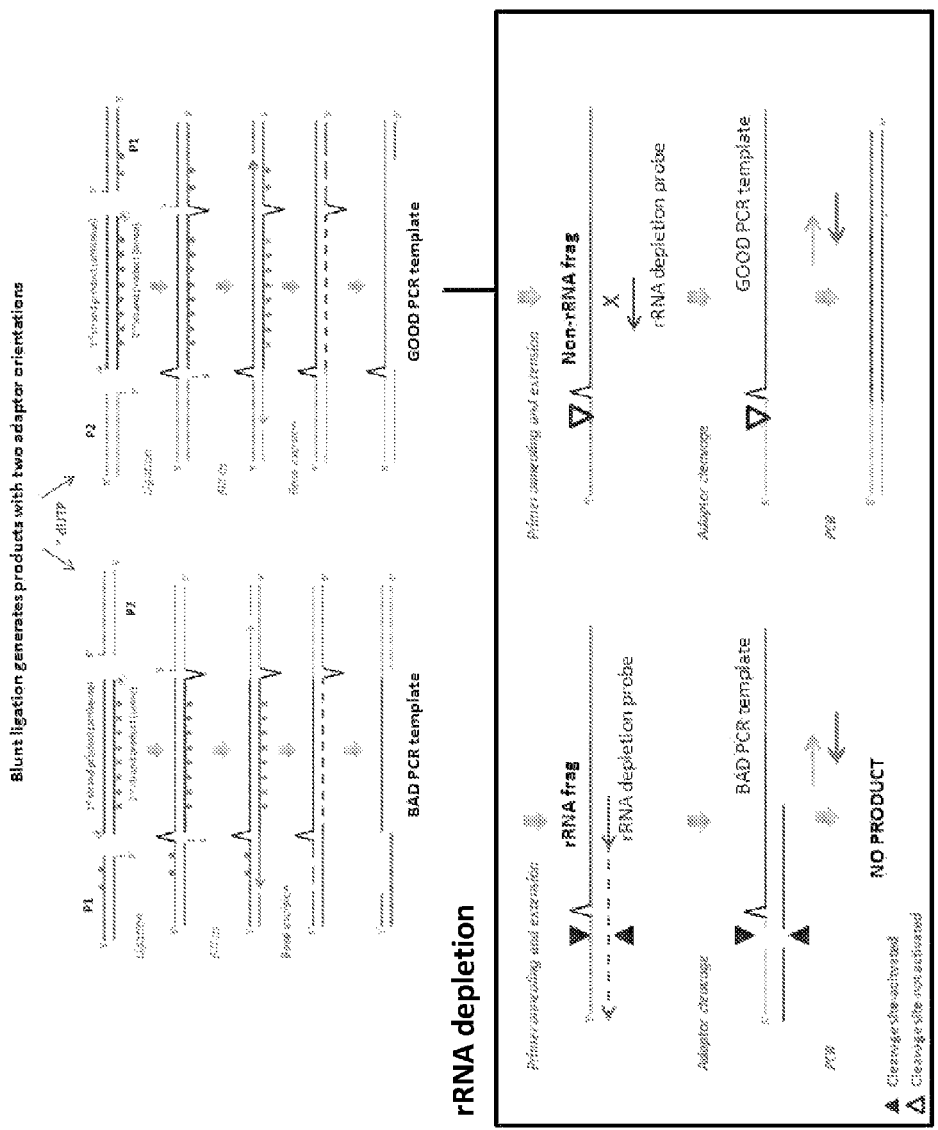
FIG. 5 depicts a method of directional library construction.

Example 3—Generation of a Directional cDNA Library (FIG. 5)

This example describes the generation of a directional cDNA library using conventional blunt-end ligation with modified duplex adaptors and 50 ng of poly(A)+ selected messenger RNA as a starting material.

First Strand Synthesis

First strand cDNA was generated using random hexamer priming. The first strand synthesis reaction was conducted using the Invitrogen SuperScript III Reverse Transcriptase kit, with 10 µM of random hexamers, 3.0 mM $MgCl_2$ and 1.0 mM dNTPs. The cDNA synthesis reaction was carried out in 10 µL volume, incubated at 40 degrees Celsius for 60 minutes and chilled to 4 degrees Celsius.

Second Strand Synthesis with dUTP Incorporation

Second strand synthesis was performed using the New England Biolabs NEBNext Second Strand Synthesis Module, where the Second Strand Synthesis (dNTP-free) Reaction Buffer was supplemented with dNTP mix containing 0.2 mM of dATP, dCTP and dGTP, and 0.54 mM dUTP. RNAse H-mediated nick translation was carried out by adding 65 µL of second strand synthesis master mix and incubating for one hour at 16 degrees Celsius. The reaction was stopped by adding 45 µL of 25 mM EDTA.

Fragmentation and Purification of cDNA Fragments

The 120 µL second strand synthesis reaction was subjected to acoustic fragmentation using the Covaris S-series System according to the manufacturer's instructions, using the manufacturer recommended settings to produce fragmented DNA with an average fragment size of 150-200 bases. Fragmented DNA was concentrated using QIAquick PCR purification kit, according to the manufacturer's instructions. The fragmented and concentrated DNA was quantitated and run on Agilent Bioanalyzer DNA 1000 chip to ensure fragment distribution of 150-200 bp length.

End Repair

The ends of the fragmented cDNA were repaired to generate blunt ends with 5' phosphates and 3' hydroxyls. End repair of the fragmented DNA was performed according to the Encore™ Ultra Low Input NGS Library System I User Guide instructions using End Repair Master Mix.

Ligation with dU Marked Adaptors

Duplex adaptors were ligated to blunt-ended cDNA fragments according to the Encore™ Ultra Low Input NGS Library System I User Guide Instructions, with the exception that the Ligation Adaptor Mix contained one adaptor where the ligation strand of the adaptor had at least one dU incorporated into it.

Nick Repair/Adaptor Fill-in

Ligation of unphosphorylated adaptors leaves a single-strand nick that must be repaired prior to strand selection and amplification. To fill in the adaptor sequence and generate full-length double-stranded DNA (dsDNA), the reaction mix was heated at 72 degrees Celsius, resulting in the extension of the 3' end of the cDNA insert by Taq DNA polymerase (thereby filling in the adaptor sequence), and the melting of the unligated adaptor strand. The repaired dsDNA fragments with ligated adaptors were then purified using Agencourt RNAClean XP Beads, according to the Encore™ Ultra Low Input NGS Library System I User Guide Instructions.

Strand Selection with UDG/APE I Treatment

Uridine digestion was performed with 1 unit of UNG and 1,000 units of APE I at 37° C. for 20 minutes. Incorporation of dUTP into one strand of the cDNA insert and the ligation strand of one of the two adaptors allowed for selective removal of the products with the undesired adaptor orientation. Consequently, a polynucleotide strand with incorporated dUTP that is treated with UNG/APE I was unable to undergo amplification by a polymerase.

Library Amplification

To produce a final directional cDNA library, the UNG-selected fragments were amplified by PCR according to the Library Amplification Protocol in the Encore™ Ultra Low Input NGS Library System I User Guide.

Example 4—Depletion of Ribosomal RNA Fragments from a Genomic DNA Library from Cells Sorted by Size Cells from a human blood sample are sorted on a Beckman MoFlo cell sorter, based on surface markers into distinct populations and individuals within those populations are separated and lysed using NuGEN's Prelude Direct Lysis Module according to manufacturer's recommendations.

The resulting RNA containing solution is used as input into NuGEN's Encore® Whole Blood RNA-Seq with care being taken to avoid lysis of the nucleus. Following first strand synthesis, second strand synthesis performed in the presence of dUTPs, and adapters comprising a restriction endonuclease recognition sequence are ligated and filled-in. The second strand is degraded by UNG treatment. The reaction mixture is incubated with a set of probes designed to anneal to sequences in rRNA transcripts that are converted into cDNAs.

The hybridized probes are extended using a DNA polymerase all the way to the adapter sequence, generating double stranded adapters on undesired nucleic acids, comprising the restriction endonuclease recognition sequence. Adapters on nucleic acids that are not probe targets, remain single stranded. The double stranded adapter sequences are digested with a restriction enzyme to remove the adapter rendering them unable to amplify during the PCR enrichment step. PCR primers targeting the adapters, master mix and a thermophilic polymerase are added and thermal cycled 20 cycles. The resultant library is quantified and applied to an Illumina flow cell for sequencing.

Example 5—Depletion of Ribosomal RNA Fragments from a Genomic DNA Library on a Microfluidic System CD4+CD25+ cells are sorted from a blood sample into a pool using a Becton Dickenson Influx cell sorter based on surface markers lysed using NuGEN's Prelude Direct Lysis Module according to manufacturer's recommendations.

The resulting RNA containing solution is gently introduced to Agencourt magnetic beads to a final volume of 50 ul under conditions that favored RNA vs. DNA binding. Care is taken to avoid lysis of the cell nucleus. The bead containing solution is then loaded to NuGEN's Mondrian™ digital microfluidic system Encore Complete SP cartridge, the cartridge applied to the workstation and the appropriate script selected. Following first strand synthesis, second strand synthesis is performed in the presence of the suitable nucleotide analog according to manufacturer's instructions, Manufacturer's instructions are followed through fragmentation, ligation with suitable adapters comprising nucleotide analogs and a restriction endonuclease recognition sequence, and strand selection The products are retrieved from the system following strand selection and before the PCR enrichment step. The sample ~1 ul in 19 ul of cartridge filler fluid, was diluted to 10 ul in a solution containing InDA-C probes designed to anneal to sequences in human rRNA transcripts.

The hybridized probes are extended using a DNA polymerase all the way to the adapter sequence, generating double stranded adapters on undesired nucleic acids, comprising the restriction endonuclease recognition sequence. Adapters on nucleic acids that are not probe targets, remain single stranded. The double stranded adapter sequences are digested with a restriction enzyme to remove the adapter rendering them unable to amplify during the PCR enrichment step (FIG. 5). PCR primers targeting the adapters, master mix and a thermophilic polymerase are added and thermal cycled 20 cycles. The resultant library is quantified and applied to an Illumina flow cell for sequencing.

Example 6—Depletion of Ribosomal RNA Fragments from a Genomic DNA Library from Single Cells Expressing GFP Cells expressing GFP from a human blood sample are sorted on a FACS Vantage SE Cell sorter (BD Biosciences, San Diego, Calif., worldwideweb.bdbiosciences.com) based on color into distinct populations. Cells above a threshold GFP expression are separated into individual microwells and lysed using NuGEN's Prelude Direct Lysis Module according to manufacturer's recommendations.

Figure 6:
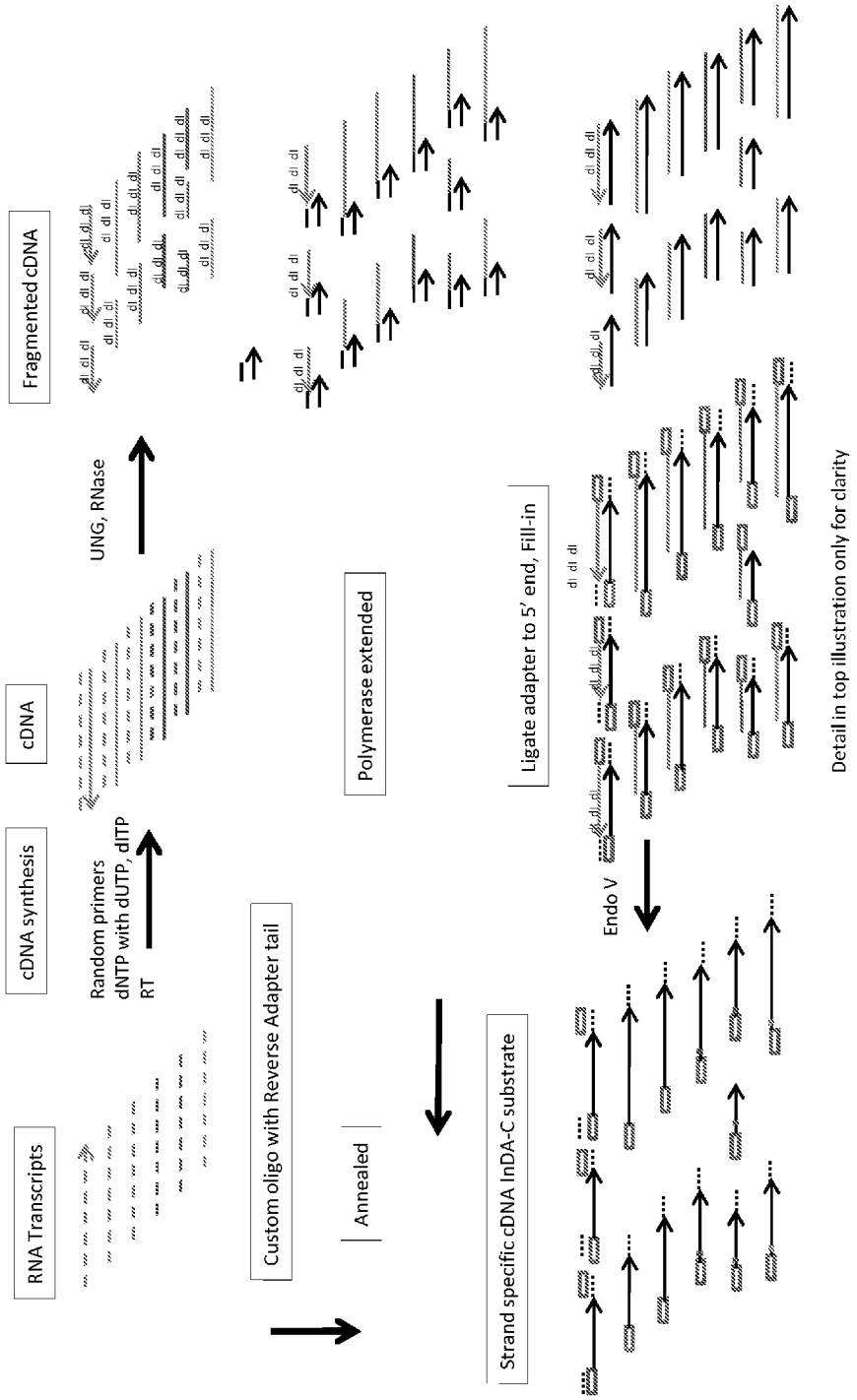
FIG. 6 depicts a method of nucleic acid depletion using InDA-C probes, comprising double cDNA hydrolysis.

The resulting RNA containing solution is primed for first strand synthesis with either N6 or USP primers (NuGEN Encore Complete first strand primer mix). The primers are extended with a Reverse Transcriptase and nucleotide solution containing dUTP and dITP at a ratio of canonical to non-canonical nucleotides for enabling fragmentation to a desired size range. Following synthesis, the cDNA is fragmented by treatment with UNG (FIG. 6) to generate fragments of the desired size range comprising blocked 3'-end.

Figure 8:
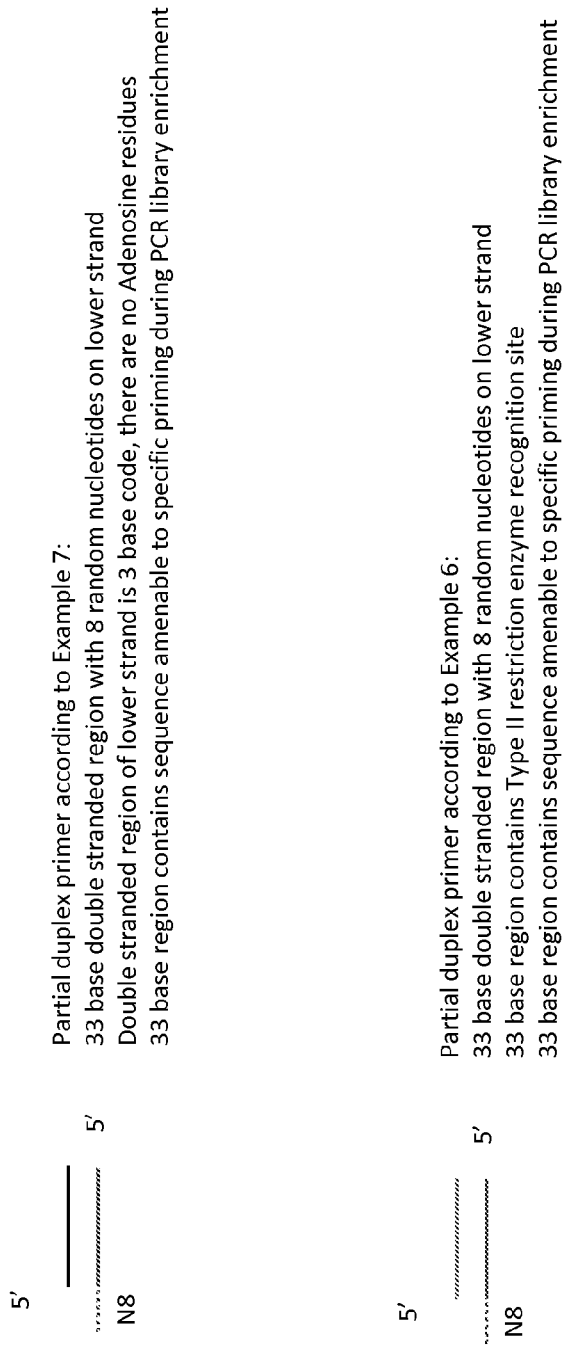
FIG. 8 depicts designs for two of the partial-duplex primers.

The resulting cDNA product with inosines is primed with a partial duplex oligonucleotide complex comprising 33 bases of double stranded structure appended with 8 random nucleotides of single stranded DNA at one 3' end (FIG. 8). A 3' extension reaction follows using the cDNA product comprising inosines as a template. Following ligation of an adapter comprising a restriction endonuclease recognition sequence to the end of the double stranded molecule and fill-in to produce blunt ends, the library is treated with Endonuclease V to remove the inosine residues and fragment the cDNA product. The resulting single stranded DNA with adapter sequences appended to each end is incubated with a set of probes designed to anneal to sequences within cDNAs corresponding to rRNA sequences.

Figure 9:
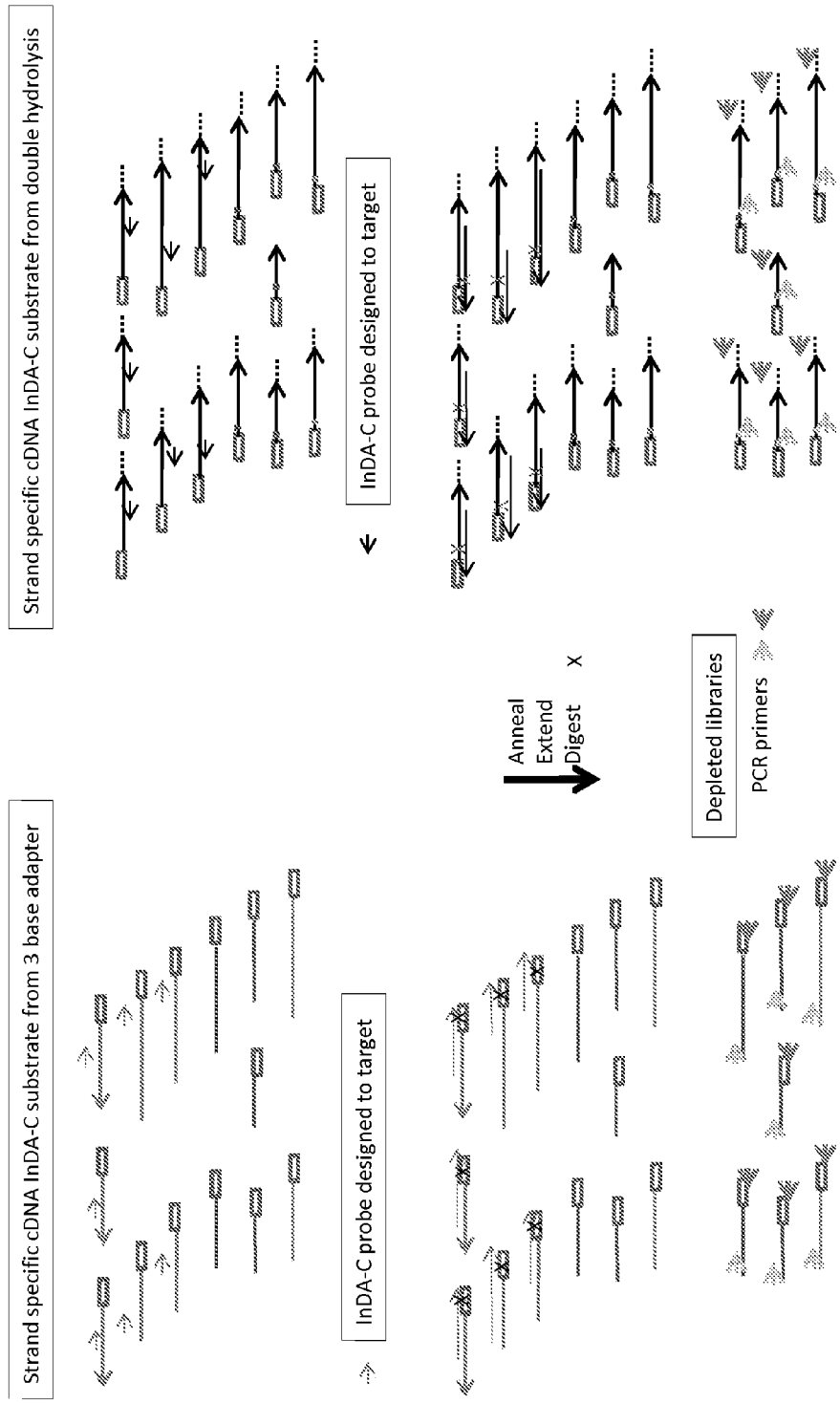
FIG. 9 depicts a method for of undesired nucleic acids by universal prokaryotic InDA-C probes.

The hybridized probes are extended using a DNA polymerase all the way to the adapter sequence, generating double stranded adapters on undesired nucleic acids, comprising the restriction endonuclease recognition sequence. Adapters on nucleic acids that are not probe targets, remain single stranded. The double stranded adapter sequences are digested with a restriction enzyme to remove the adapter rendering them unable to amplify during the PCR enrichment step (FIG. 9). PCR primers targeting the adapters, master mix and a thermophilic polymerase are added and thermal cycled 20 cycles. The resultant library is quantified and applied to an Illumina flow cell for sequencing.

Example 7—Depletion of Ribosomal RNA Fragments from a Genomic DNA Library from Single Cells Expressing a CFP-YFP FRET System Cells expressing a CFP-YFP FRET system are sorted on a FACS Vantage SE Cell sorter (BD Biosciences, San Diego, Calif., worldwideweb.bdbiosciences.com) based on the FRET emission signal into distinct populations. Cells above a threshold FRET emission are separated into individual microwells and lysed using NuGEN's Prelude Direct Lysis Module according to manufacturer's recommendations.

Figure 7:
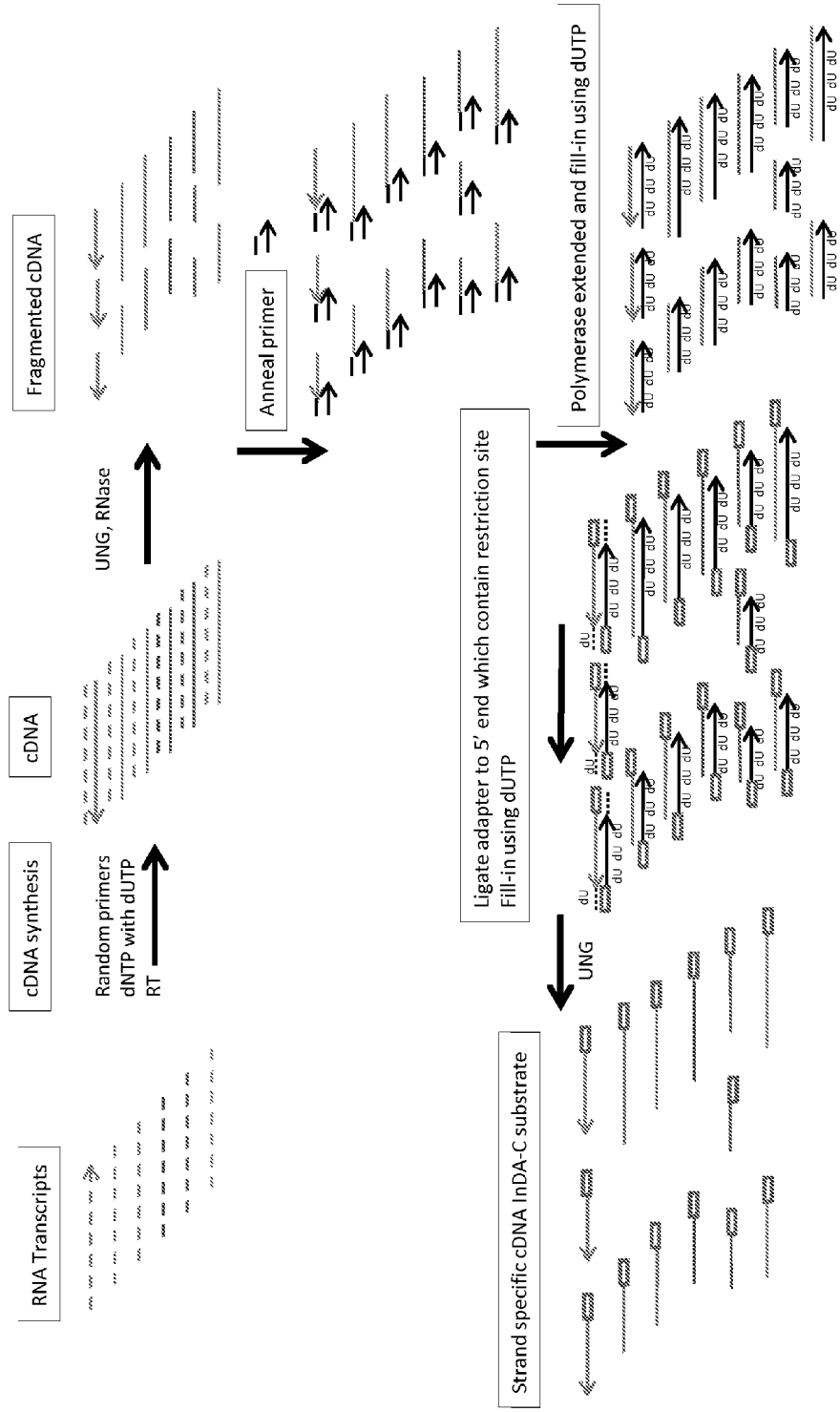
FIG. 7 depicts another method of nucleic acid depletion using InDA-C probes.

The resulting RNA containing solution is primed for first strand synthesis with either N6 or USP primers (Encore Complete first strand primer mix, NuGEN). The primers are extended with a Reverse Transcriptase and nucleotide solution containing dUTP. Following synthesis the cDNA is fragmented by treatment with UNG (FIG. 7) to generate fragments of the desired size range. This cDNA product is primed with a partial duplex oligonucleotide complex library, each complex comprising 33 bases of double stranded structure appended with 8 random nucleotides of single stranded DNA as 3' overhang (FIG. 8). The oligo complexes are made up of 2 strands comprising 33 nucleotides on the short strand and 41 nucleotides on the long strand, respectively. The 33 bases of the ling strand falling within the double-stranded portion lacks any adenine nucleotides.

The 8 base random sequence is annealed to the fragmented cDNA and extended with a DNA polymerase in the presence of dUTP. At the same time, the 33 base oligo is displaced by the DNA polymerase producing a blunt ended molecule. By virtue of lacking adenines in the double stranded portion of the long strand of the oligo complex, the extension product displacing the short strand does not incorporate any uracils. Following ligation of an adapter comprising a restriction endonuclease recognition sequence to the end of the double stranded molecule to the end of the double stranded molecule and fill-in to produce blunt ends, the library is treated with UNG to fragment the DNA where dUs residues are incorporated. The resulting single stranded DNA with adapter sequences appended to each end is incubated with a set of probes designed to anneal to sequences within cDNAs corresponding to rRNA sequences.

The hybridized probes are extended using a DNA polymerase all the way to the adapter sequence, generating double stranded adapters on undesired nucleic acids, comprising the restriction endonuclease recognition sequence. Adapters on nucleic acids that are not probe targets, remain single stranded. The double stranded adapter sequences are digested with a restriction enzyme to remove the adapter rendering them unable to amplify during the PCR enrichment step (FIG. 9). PCR primers targeting the adapters, master mix and a thermophilic polymerase are added and thermal cycled 20 cycles. The resultant library is quantified and applied to an Illumina flow cell for sequencing.

Example 8—Probe Design for the Depletion of Undesired Nucleic Acid Fragments from Library This example describes the depletion of undesired nucleic acid fragments from a library of various origins, using insert-dependent adaptor cleavage (InDA-C) probes that target the undesired nucleic acid fragments.

Probe Design and Synthesis

Target sequences for depletion are compiled for transcripts that might frequently be found in high abundance within a given sample type. Examples of such transcripts are ribosomal RNA (rRNAs) and mitochondrial RNAs in most sample types, globin within blood samples and chloroplast RNAs within plant samples. These sequences are compiled from public data such as RefSeq when available or from empirical data sources (Grape Genome Browser available online from Genoscope, Denoeud et al. Annotating genomes with massive-scale RNA sequencing. Genome Biology 2008, 9:R175 doi:10.1186/gb-2008-9-12-r175: worldwide-web.genoscope.cns.fr/externe/GenomeBrowserNitis/) as was the case with grape, which does not have a well annotated or complete reference genome. Orientation of probes is determined based on which strand of template is to be retained following adapter ligation. Each undesired transcript is computationally "fragmented" into 70 base regions and these regions are queried using PCR primer design software such as Primer3 (Steve Rozen and Helen J. Skaletsky (2000) Primer3 on the WWW for general users and for biologist programmers. In: Krawetz S, Misener S (eds) Bioinformatics Methods and Protocols: Methods in Molecular Biology. Humana Press, Totowa, N.J., pp 365-386). Target melting temperature is set to 60° C. for human cytoplasmic and mitochondrial rRNA and human globin message and 65° C. for grape cytoplasmic and mitochondrial rRNA and grape chloroplast rRNA.

Primer sequences proposed by Primer3 are BLASTed against known transcript sequences from the same organism to limit or eliminate off-target interactions. Probes determined to have off-target interactions are removed from the pool. The primer probe oligonucleotides are produced using standard phosphoramidite chemistries.

Depletion of RNA and DNA Sequences

The designed primer probes specific for undesired nucleic acid sequences, such as human cytoplasmic and mitochondrial rRNA, human globin mRNA, grape cytoplasmic and mitochondrial rRNA, grape chloroplast rRNA, are utilized in depleting the undesired sequences in one of the ways described herein, such as one of the methods exemplified in Examples 1, 2, 4, 5, 6, or 7 (FIGS. 1, 5-7, and 9). Lower annealing and extension temperatures may be used for more aggressive strand depletion conditions. Briefly, single stranded nucleic acids in various adapter configurations are hybridized with a set of designed primer probes for depleting undesired nucleic acids. The nucleic acid is prepared with a restriction endonuclease recognition sequence supplied on the 5' end. The primer probes are extended resulting in a double-stranded structure around the restriction endonuclease recognition sequence. Cleaving the nucleic acid at the restriction endonuclease recognition site further destroys a primer annealing sequence targeted by a subsequent amplification reaction, e.g. PCR. Thus, nucleic acids targeted by the primer probes are unavailable for amplification, enriching the remainder of the nucleic acids in a sample.

What is claimed is:

1. A method of reducing an abundance ratio of non-desired to desired nucleic acid sequence from a single-stranded nucleic acid library, the method comprising:
   a) annealing a sequence-specific oligonucleotide probe to a non-desired nucleic acid sequence in a single-stranded nucleic acid library, wherein the non-desired nucleic acid sequence is in a non-desired single-stranded nucleic acid fragment comprising an adaptor sequence, wherein the single-stranded nucleic acid library further comprises a desired nucleic acid sequence in a desired single-stranded nucleic acid fragment comprising the adaptor sequence;
   b) extending the sequence-specific oligonucleotide probe annealed to the non-desired nucleic acid sequence to produce a partial double-stranded nucleic acid comprising a double-stranded adaptor;
   c) selectively cleaving the partial double-stranded nucleic acid at a cleavage site in the double-stranded adaptor; and
   d) amplifying the desired nucleic acid sequence, thereby reducing an abundance ratio of the non-desired to the desired nucleic acid sequence from the single-stranded nucleic acid library.

2. The method of claim 1, wherein the desired single-stranded nucleic acid fragment comprises an adaptor at a 5' end and a 3' end.

3. The method of claim 2, wherein the amplifying the desired nucleic acid sequence comprises amplifying with a primer that anneals to the adaptor at the 3' end and a primer that anneals to the complement of the adaptor at the 5' end.

4. The method of claim 1, wherein the desired single-stranded nucleic acid fragment and the non-desired single-stranded nucleic acid fragment comprise DNA.

5. The method of claim 1, wherein the selectively cleaving comprises cleavage with a cleavage agent specific for a double-stranded nucleic acid sequence in the partial double-stranded nucleic acid.

6. The method of claim 5, wherein the cleavage agent is a restriction endonuclease.

7. The method of claim 6, wherein the restriction endonuclease is BspQI.

8. The method of claim 1, wherein the cleavage site is capable of recognition by a cleavage agent.

9. The method of claim 1, wherein the amplifying the desired nucleic acid sequence comprises amplifying with a primer that anneals to a complement of the adaptor sequence.

10. The method of claim 1, wherein the non-desired nucleic acid sequence comprises a sequence of ribosomal RNA (rRNA), mitochondrial DNA, or human globin mRNA.

11. The method of claim 1, wherein the amplifying comprises amplifying with a DNA polymerase.

12. The method of claim 1, further comprising generating the single-stranded nucleic acid library of step a) from a double stranded nucleic acid.

13. The method of claim 12, wherein the generating comprises selectively removing a second cDNA strand from a double-stranded nucleic acid library member from the double stranded nucleic acid, thereby retaining a first cDNA strand of the double-stranded nucleic acid library member.

14. The method of claim 13, wherein the second cDNA strand comprises a non-canonical nucleotide, wherein the first cDNA strand does not comprise the non-canonical nucleotide.

15. The method of claim 14, wherein the non-canonical nucleotide comprises a uridine or inosine base.

16. The method of claim 14, wherein the selectively removing comprises cleaving a base portion of the non-canonical nucleotide to create an abasic site.

17. The method of claim 16, wherein the selectively removing further comprises cleaving the second cDNA strand at the abasic site.

18. A method of creating a strand retained library of nucleic acids, the method comprising:
   a) annealing a partial duplex primer to a nucleic acid template strand, wherein the nucleic acid template strand comprises a non-canonical nucleotide, wherein the partial duplex primer comprises a 3' overhang;
   b) extending the partial duplex primer to form a primer extension product strand, thereby forming a double-stranded nucleic acid comprising (i) the primer extension product strand and (ii) the nucleic acid template strand;
   c) ligating an adaptor to a 5' end of the primer extension product strand; and
   d) cleaving the nucleic acid template strand from the double-stranded nucleic acid, wherein the cleaving comprises use of a cleavage agent specific for the non-canonical nucleotide, thereby creating a strand retained library of nucleic acids.

19. The method of claim 18, wherein the adaptor comprises a recognition sequence for a restriction endonuclease specific for double-stranded DNA.

20. The method of claim 19, further comprising:
e) hybridizing a probe to a sequence of the primer extension product;
f) extending the probe with a DNA polymerase, thereby producing a partial duplex nucleic acid; and
g) treating the partial duplex nucleic acid with a restriction endonuclease specific for double-stranded DNA, thereby cleaving the partial duplex nucleic acid at the recognition sequence.

21. The method of claim 20, further comprising performing polymerase chain reaction (PCR) with a primer that is hybridizable to a complement of a sequence of the adaptor.

22. The method of claim 18, wherein the nucleic acid template strand originates from a single cell.

23. A method of depleting or reducing a non-desired nucleic acid sequence from a nucleic acid library comprising the non-desired nucleic acid sequence in a non-desired DNA fragment having an adaptor at each end and a desired nucleic acid sequence in a desired DNA fragment having an adaptor at each end, the method comprising:
a) annealing a sequence-specific oligonucleotide probe to the non-desired nucleic acid sequence in the non-desired DNA fragment having an adaptor at each end, wherein a 3' end of the sequence-specific oligonucleotide probe comprises perfect complementarity to a portion of the non-desired nucleic acid sequence, thereby producing a DNA fragment with a partial duplex;
b) treating the DNA fragment with the partial duplex with a nuclease that cleaves at a double-stranded site in the partial duplex; and
c) amplifying the desired nucleic acid sequence in the desired DNA fragment having an adaptor at each end by performing polymerase chain reaction (PCR) with a set of primers that anneal to the adaptor at each end of the desired DNA fragment, thereby generating amplified desired DNA fragments.

24. The method of claim 23, wherein the nuclease comprises an endonuclease.

25. The method of claim 23, wherein the nuclease comprises a restriction endonuclease.

26. The method of claim 23, wherein the nuclease induces breaks in double-stranded DNA.

27. The method of claim 23, further comprising constructing the nucleic acid library.

28. The method of claim 27, wherein the nucleic acid library is constructed from a sample of interest while retaining an unbiased nucleic acid template population.

29. The method of claim 27, wherein the non-desired DNA fragment and the desired DNA fragment is each a cDNA fragment.

30. The method of claim 29, wherein the constructing the nucleic acid library comprises reverse transcribing RNA in an RNA sample to form a first cDNA strand of the cDNA fragment.

31. The method of claim 30, wherein the RNA sample comprises total RNA from a biological source.

32. The method of claim 31, wherein the biological source is a human.

33. The method of claim 30, further comprising purifying the RNA sample.

34. The method of claim 30, wherein the RNA sample comprises less than 20 ng of nucleic acid.

35. The method of claim 30, wherein the RNA comprises ribosomal RNA (rRNA).

36. The method of claim 30, wherein the reverse transcribing RNA comprises annealing a random primer to the RNA.

37. The method of claim 36, wherein the random primer comprises a random hexamer.

38. The method of claim 30, further comprising extending a 3' end of the first cDNA strand with a terminal transferase.

39. The method of claim 30, further comprising performing second strand cDNA synthesis to form a second strand of the cDNA fragment.

40. The method of claim 23, wherein the non-desired nucleic acid sequence is an rRNA sequence.

41. The method of claim 23, wherein the non-desired nucleic acid sequence is a mitochondrial sequence.

42. The method of claim 41, wherein the mitochondrial sequence is a mitochondrial RNA sequence.

43. The method of claim 42, wherein the mitochondrial RNA sequence is a mitochondrial rRNA sequence.

44. The method of claim 23, wherein the sequence-specific oligonucleotide probe is designed to be complementary to the non-desired nucleic acid sequence.

45. The method of claim 23, wherein at least one of the adaptor at each end of the desired DNA fragment comprises a barcode.

46. The method of claim 23, further comprising sequencing the amplified desired DNA fragments.

47. The method of claim 46, wherein the sequencing comprises massively parallel sequencing.

48. The method of claim 47, wherein the massively parallel sequencing comprises paired-end sequencing.

49. The method of claim 23, wherein the set of primers comprise a barcode.

50. The method of claim 23, wherein the nucleic acid library is a directional cDNA library.

51. The method of claim 23, further comprising purifying the desired DNA fragment and non-desired DNA fragment in the nucleic acid library before step a).

52. The method of claim 23, further comprising purifying the amplified desired DNA fragments of step c).

* * * * *